US012588961B2

(12) United States Patent
Lin et al.

(10) Patent No.: US 12,588,961 B2
(45) Date of Patent: Mar. 31, 2026

(54) ENGAGEMENT CONTROL OF INSTRUMENT FEEDER DEVICES

(71) Applicant: Auris Health, Inc., Santa Clara, CA (US)

(72) Inventors: Jiayi Lin, San Mateo, CA (US); Casey Teal Landey, San Francisco, CA (US); Chauncey F. Graetzel, Palo Alto, CA (US)

(73) Assignee: Auris Health, Inc., Santa Clara, CA (US)

( * ) Notice: Subject to any disclaimer, the term of this patent is extended or adjusted under 35 U.S.C. 154(b) by 149 days.

(21) Appl. No.: 18/363,646

(22) Filed: Aug. 1, 2023

(65) Prior Publication Data

US 2024/0001541 A1     Jan. 4, 2024

Related U.S. Application Data

(63) Continuation of application No. PCT/IB2022/051395, filed on Feb. 16, 2022.
(Continued)

(51) Int. Cl.
*A61B 34/30*          (2016.01)
*A61B 34/32*          (2016.01)
(Continued)

(52) U.S. Cl.
CPC ............. *A61B 34/32* (2016.02); *B25J 9/1628* (2013.01); *B25J 13/085* (2013.01); *B25J 13/088* (2013.01);
(Continued)

(58) Field of Classification Search
CPC ............ A61B 34/32; A61B 2034/2061; A61B 2034/301; A61B 2034/303;
(Continued)

(56) References Cited

U.S. PATENT DOCUMENTS

| | | | |
|---|---|---|---|
| 8,231,610 | B2 | 7/2012 | Jo et al. |
| 8,317,744 | B2 | 11/2012 | Kirschenman |

(Continued)

FOREIGN PATENT DOCUMENTS

| | | |
|---|---|---|
| CN | 107427327 A | 12/2017 |
| CN | 109821138 A | 5/2019 |

(Continued)

OTHER PUBLICATIONS

Office Action from U.S. Appl. No. 18/363,665, dated May 9, 2025, 9 pages.
(Continued)

*Primary Examiner* — Adam R Mott
*Assistant Examiner* — Sagar Kc
(74) *Attorney, Agent, or Firm* — Paradice & Li LLP

(57) ABSTRACT

Systems, devices, and methods for controlling an instrument feeder device to engage with and/or control a medical instrument are discussed herein. For example, an instrument feeder device can be configured to couple to a drive output of a robotic arm and/or engage with an elongate shaft of a medical instrument. The drive output can be configured to control the engagement assembly to selectively engage with and/or retain the elongate shaft. A state of the engagement assembly can be determined based on an amount of force applied by the drive output, a position of the drive output, and/or other information.

20 Claims, 27 Drawing Sheets

Related U.S. Application Data

(60) Provisional application No. 63/150,533, filed on Feb. 17, 2021, provisional application No. 63/150,527, filed on Feb. 17, 2021.

(51) Int. Cl.
| | |
|---|---|
| *B25J 9/16* | (2006.01) |
| *B25J 13/08* | (2006.01) |
| *A61B 34/20* | (2016.01) |
| *A61B 90/00* | (2016.01) |

(52) U.S. Cl.
CPC . *A61B 2034/2061* (2016.02); *A61B 2034/301* (2016.02); *A61B 2034/303* (2016.02); *A61B 2090/064* (2016.02)

(58) Field of Classification Search
CPC ... A61B 2090/064; A61B 34/37; A61B 34/70; A61B 1/307; A61B 2034/105; A61B 2034/2048; A61B 2034/2051; A61B 2034/2072; A61B 2090/306; A61B 2090/309; A61B 2090/3614; A61B 2090/376; A61B 2090/3762; A61B 34/30; A61B 34/20; B25J 9/0084
See application file for complete search history.

(56) References Cited

U.S. PATENT DOCUMENTS

| | | | |
|---|---|---|---|
| 8,672,837 B2 | 3/2014 | Roelle et al. | |
| 10,556,092 B2 | 2/2020 | Yu et al. | |
| 10,569,052 B2 | 2/2020 | Kokish et al. | |
| 10,687,903 B2 | 6/2020 | Lewis et al. | |
| 11,076,924 B2 | 8/2021 | Kim et al. | |
| 2005/0119641 A1 | 6/2005 | Jaspers | |
| 2007/0010801 A1 | 1/2007 | Chen et al. | |
| 2008/0146875 A1 | 6/2008 | Noguchi et al. | |
| 2009/0247942 A1 | 10/2009 | Kirschenman | |
| 2011/0015483 A1* | 1/2011 | Barbagli | A61B 1/307 600/108 |
| 2012/0041450 A1 | 2/2012 | Awtar et al. | |
| 2012/0071822 A1 | 3/2012 | Romo et al. | |
| 2013/0144275 A1 | 6/2013 | Umemoto | |
| 2014/0005705 A1 | 1/2014 | Weir et al. | |
| 2014/0276233 A1 | 9/2014 | Murphy | |
| 2014/0276936 A1* | 9/2014 | Kokish | A61B 34/70 606/130 |
| 2014/0277333 A1 | 9/2014 | Lewis et al. | |
| 2014/0277334 A1 | 9/2014 | Yu et al. | |
| 2015/0297864 A1* | 10/2015 | Kokish | A61B 34/37 604/95.04 |
| 2015/0352715 A1 | 12/2015 | Yanagihara et al. | |
| 2016/0135662 A1 | 5/2016 | Hatakeyama et al. | |
| 2016/0135911 A1 | 5/2016 | Yanagihara et al. | |
| 2016/0256232 A1 | 9/2016 | Awtar et al. | |
| 2016/0354582 A1 | 12/2016 | Yu et al. | |
| 2016/0360950 A1 | 12/2016 | Takahashi et al. | |
| 2016/0360952 A1 | 12/2016 | Yamanaka et al. | |
| 2017/0189128 A1 | 7/2017 | Auld | |
| 2017/0332882 A1* | 11/2017 | Yamamoto | A61B 1/0016 |
| 2017/0340396 A1 | 11/2017 | Romo et al. | |
| 2018/0177383 A1* | 6/2018 | Noonan | A61B 1/0051 |
| 2018/0177556 A1 | 6/2018 | Noonan | |
| 2018/0214220 A1 | 8/2018 | Kan | |
| 2018/0353250 A1* | 12/2018 | Fournier | A61B 34/30 |
| 2019/0000568 A1 | 1/2019 | Connolly et al. | |
| 2019/0117247 A1 | 4/2019 | Kim et al. | |
| 2019/0125381 A1* | 5/2019 | Scheib | A61B 17/29 |
| 2019/0125387 A1* | 5/2019 | Parihar | A61B 17/282 |
| 2019/0125432 A1* | 5/2019 | Shelton, IV | A61B 17/1285 |
| 2019/0314098 A1 | 10/2019 | Park et al. | |
| 2021/0045823 A1 | 2/2021 | Landey et al. | |
| 2021/0045824 A1 | 2/2021 | Landey et al. | |
| 2021/0196251 A1 | 7/2021 | Dull et al. | |
| 2021/0290261 A1 | 9/2021 | Cohen et al. | |
| 2022/0226054 A1* | 7/2022 | Beckman | A61B 17/07207 |
| 2022/0226057 A1* | 7/2022 | Beckman | A61B 17/07207 |
| 2022/0401171 A1 | 12/2022 | Comenencia Ortiz et al. | |
| 2023/0104573 A1 | 4/2023 | Sholev | |

FOREIGN PATENT DOCUMENTS

| | | |
|---|---|---|
| CN | 111544117 A | 8/2020 |
| EP | 3431025 B1 | 6/2023 |
| JP | 2007014609 A | 1/2007 |
| JP | 2018533450 A | 11/2018 |
| JP | 2020513904 A | 5/2020 |
| JP | 2020526254 A | 8/2020 |
| KR | 1020190101860 A | 9/2019 |
| KR | 1020200000441 A | 1/2020 |
| KR | 1020200071744 A | 6/2020 |
| WO | 2016043845 A1 | 3/2016 |
| WO | 2016054256 A1 | 4/2016 |
| WO | 2018125917 A1 | 7/2018 |
| WO | 2019074669 A1 | 4/2019 |
| WO | 2019133438 A1 | 7/2019 |
| WO | 2021011551 A1 | 1/2021 |
| WO | 2022136901 A1 | 6/2022 |
| WO | 2022175850 A1 | 8/2022 |
| WO | 2022175851 A1 | 8/2022 |

OTHER PUBLICATIONS

Office Action from Korean Patent Application No. 10-2023-7031604, dated Mar. 13, 2025, 15 pages.
Office Action from Japan Patent Application No. 2023-549633, dated Apr. 22, 2025, 17 pages.
European Communication with Extended Search Report, dated Jan. 15, 2025, from European Patent Application No. 22755667.7, pp. 1-9.
CN Office Action for Appl. No. 202280015575.3, dated Jan. 31, 2024.
European Communication with Extended Search Report, dated Nov. 26, 2024, from European Patent Application No. 22755668.5, pp. 1-8.
International Preliminary Report on Patentability for Appl. No. PCT/IB2022/051395, dated Aug. 22, 2023, 5 pages.
International Preliminary Report on Patentability for Appl. No. PCT/IB2022/051396, dated Aug. 22, 2023, 5 pages.
International Search Report for Appl. No. PCT/IB2022/051395, dated May 31, 2022, 4 pages.
International Search Report for Appl. No. PCT/IB2022/051396, dated May 25, 2022, 3 pages.
Written Opinion for Appl. No. PCT/IB2022/051395, dated May 31, 2022, 4 pages.
Written Opinion for Appl. No. PCT/IB2022/051396, dated May 25, 2022, 4 pages.
Office Action from Korean Patent Application No. 10-2023-7031434, dated Feb. 17, 2025, 21 pages.
Notice of Allowance from U.S. Appl. No. 18/363,665, dated Nov. 13, 2025, 7 pages.
Office Action from Japan Patent Application No. 2023-549626, dated May 7, 2025, 15 pages.
Office Action from Japan Patent Application No. 2023-549633, dated Sep. 22, 2025, 13 pages.

* cited by examiner

FIG. 4
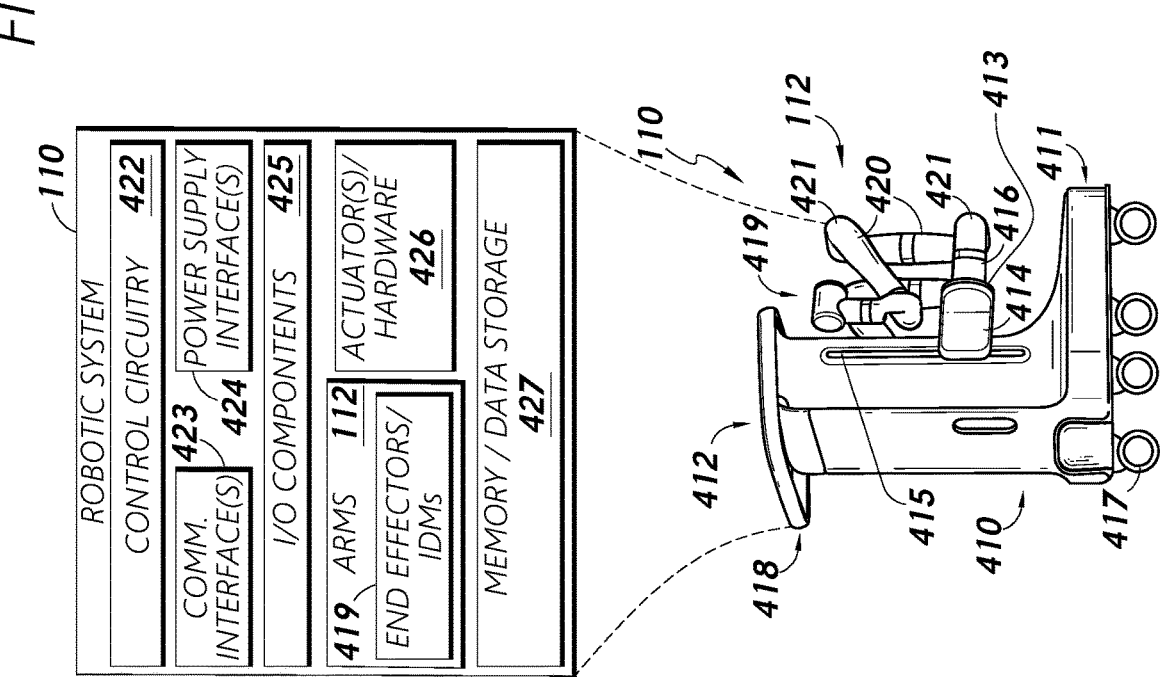
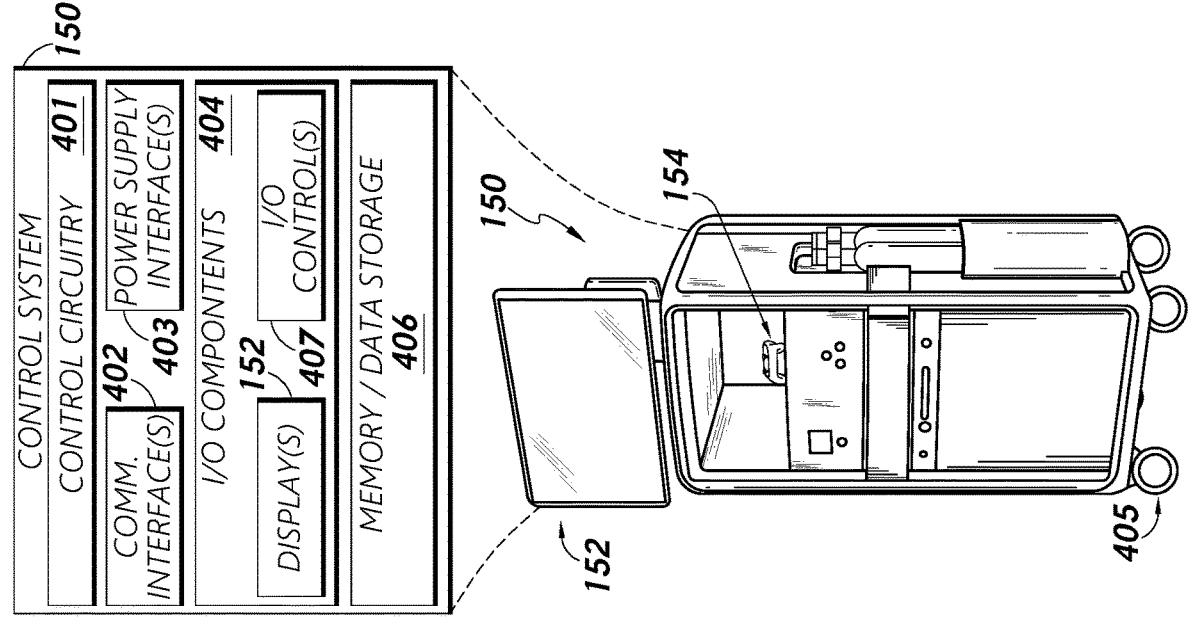

*1400*

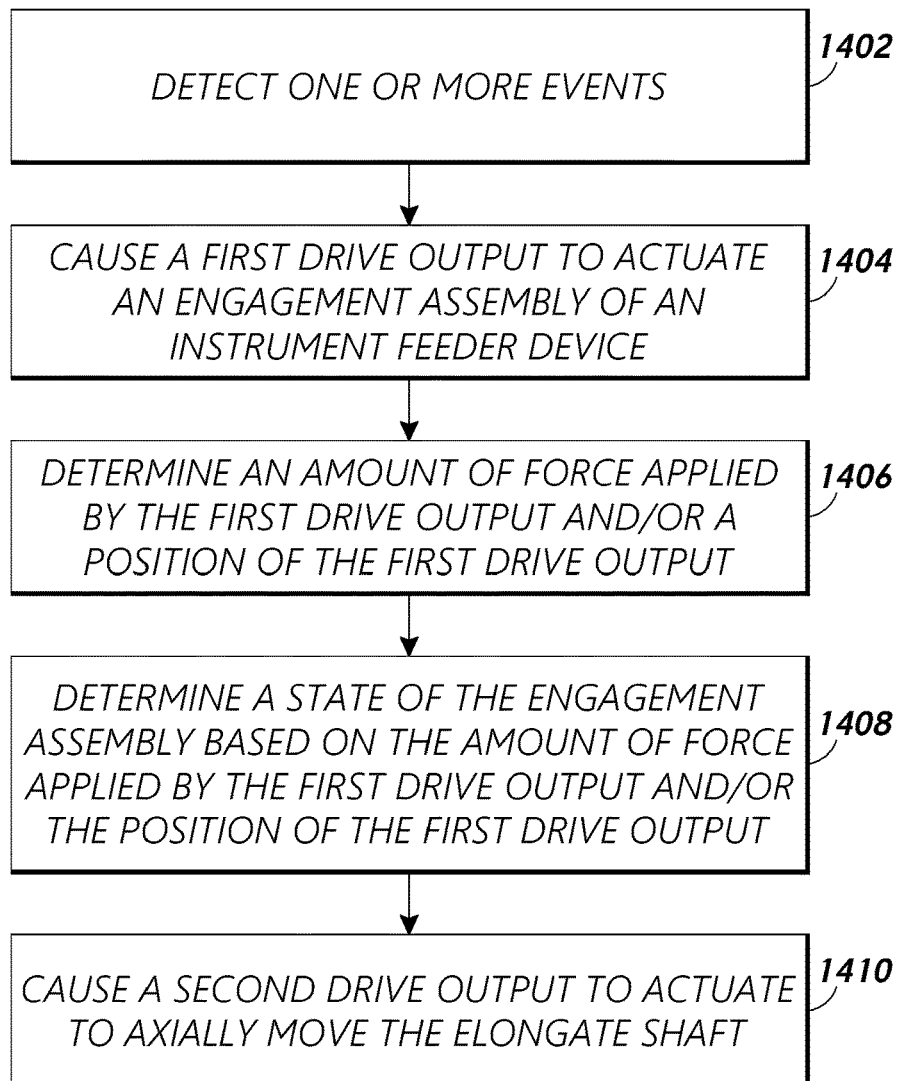

```
┌────────────────────────────────────────┐
│                                        │ 1402
│        DETECT ONE OR MORE EVENTS       │
│                                        │
└────────────────────────────────────────┘
                     │
                     ▼
┌────────────────────────────────────────┐
│   CAUSE A FIRST DRIVE OUTPUT TO ACTUATE │ 1404
│       AN ENGAGEMENT ASSEMBLY OF AN      │
│          INSTRUMENT FEEDER DEVICE       │
└────────────────────────────────────────┘
                     │
                     ▼
┌────────────────────────────────────────┐
│  DETERMINE AN AMOUNT OF FORCE APPLIED   │ 1406
│   BY THE FIRST DRIVE OUTPUT AND/OR A    │
│     POSITION OF THE FIRST DRIVE OUTPUT  │
└────────────────────────────────────────┘
                     │
                     ▼
┌────────────────────────────────────────┐
│    DETERMINE A STATE OF THE ENGAGEMENT  │
│  ASSEMBLY BASED ON THE AMOUNT OF FORCE  │ 1408
│ APPLIED BY THE FIRST DRIVE OUTPUT AND/OR│
│    THE POSITION OF THE FIRST DRIVE OUTPUT│
└────────────────────────────────────────┘
                     │
                     ▼
┌────────────────────────────────────────┐
│ CAUSE A SECOND DRIVE OUTPUT TO ACTUATE  │ 1410
│    TO AXIALLY MOVE THE ELONGATE SHAFT   │
└────────────────────────────────────────┘
```

CAUSE A DRIVE
OUTPUT OF A FIRST
ROBOTIC ARM
AND/OR A SECOND
ROBOTIC
ARM TO ACTUATE

1608

DETERMINE A FIRST FORCE
APPLIED BY THE DRIVE
OUTPUT, A SECOND FORCE
APPLIED BY THE SECOND
ROBOTIC ARM, A SHAPE OF
THE ELONGATE SHAFT,
AND/OR A POSITION OF AT
LEAST A PORTION OF THE
ELONGATE SHAFT

1600

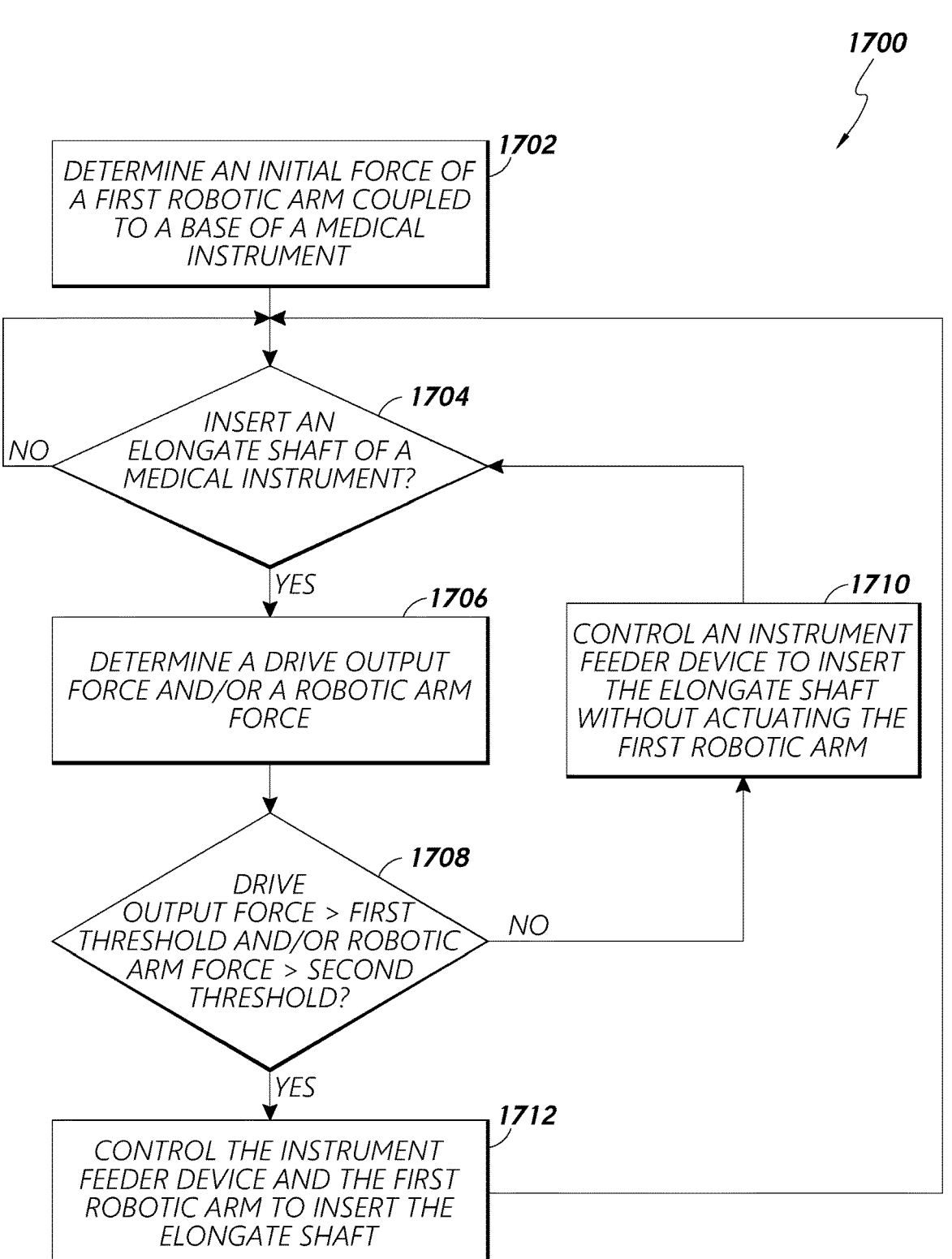

*1700*

*1702*
DETERMINE AN INITIAL FORCE OF A FIRST ROBOTIC ARM COUPLED TO A BASE OF A MEDICAL INSTRUMENT

*1704*
INSERT AN ELONGATE SHAFT OF A MEDICAL INSTRUMENT?

NO

YES

*1706*
DETERMINE A DRIVE OUTPUT FORCE AND/OR A ROBOTIC ARM FORCE

*1710*
CONTROL AN INSTRUMENT FEEDER DEVICE TO INSERT THE ELONGATE SHAFT WITHOUT ACTUATING THE FIRST ROBOTIC ARM

*1708*
DRIVE OUTPUT FORCE > FIRST THRESHOLD AND/OR ROBOTIC ARM FORCE > SECOND THRESHOLD?

NO

YES

*1712*
CONTROL THE INSTRUMENT FEEDER DEVICE AND THE FIRST ROBOTIC ARM TO INSERT THE ELONGATE SHAFT

*FIG. 17*

*1800*
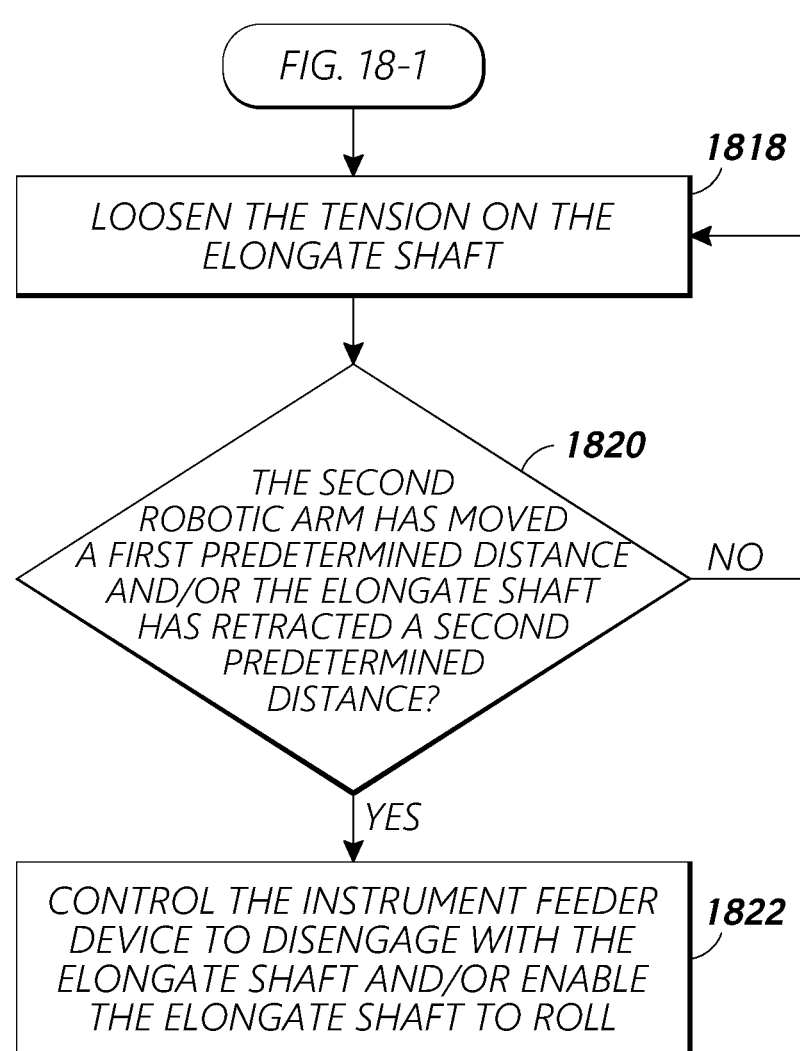
FIG. 18-1
LOOSEN THE TENSION ON THE
ELONGATE SHAFT
*1818*
THE SECOND
ROBOTIC ARM HAS MOVED
A FIRST PREDETERMINED DISTANCE
AND/OR THE ELONGATE SHAFT
HAS RETRACTED A SECOND
PREDETERMINED
DISTANCE?
*1820*
NO
YES
CONTROL THE INSTRUMENT FEEDER
DEVICE TO DISENGAGE WITH THE
ELONGATE SHAFT AND/OR ENABLE
THE ELONGATE SHAFT TO ROLL
*1822*
FIG. 18-2

ENGAGEMENT CONTROL OF INSTRUMENT FEEDER DEVICES

RELATED APPLICATION(S)

This application is a continuation of International Application No. PCT/IB2022/051395, filed Feb. 16, 2022, and entitled ENGAGEMENT CONTROL OF INSTRUMENT FEEDER DEVICES, which claims priority to U.S. Provisional Application No. 63/150,527, filed Feb. 17, 2021, and entitled ENGAGEMENT CONTROL OF INSTRUMENT FEEDER DEVICES, and U.S. Provisional Application No. 63/150,533, filed Feb. 17, 2021, and entitled INSTRUMENT SHAFT TENSIONING SYSTEM AND METHOD, the disclosures of which are hereby incorporated by reference in their entirety.

BACKGROUND

Field

The present disclosure relates to the field of medical procedures and devices.

Description of Related Art

Various medical procedures involve the use of one or more medical devices for accessing a target anatomical site in a patient. In some instances, the improper use of certain devices when accessing the site in connection with a procedure can adversely affect the health of the patient, the integrity of the medical device(s), and/or the efficacy of the procedure.

SUMMARY

In some implementations, the present disclosure relates to a system comprising an instrument feeder device and control circuitry. The instrument feeder device is configured to couple to a drive output and includes an engagement assembly configured to engage with an elongate shaft of a medical instrument. The control circuitry is configured to cause the drive output to actuate the engagement assembly and determine a state of the engagement assembly based on at least one of an amount of force applied by the drive output or a position of the drive output.

In some embodiments, the control circuitry is configured to determine the state of the engagement assembly based on at least one of a comparison of the amount of force applied by the drive output to one or more thresholds or a comparison of the position of the drive output to one or more reference positions.

In some embodiments, the engagement assembly includes an actuator configured to axially move the elongate shaft and a channel configured to receive the elongate shaft. In examples, the state of the engagement assembly indicates whether or not the actuator is engaged with the elongate shaft. In examples, the state of the engagement assembly indicates whether or not the elongate shaft is properly positioned within the channel.

In some embodiments, the control circuitry is configured to cause the drive output to actuate the engagement assembly from an engaged state in which the actuator is engaged to a disengaged state in which the actuator is disengaged, and determine a first position of the drive output that is associated with a first change in force applied by the drive output that occurred while moving the engagement assembly from the engaged state to the disengaged state. The first change in force can be greater than a first threshold.

In some embodiments, the control circuitry is configured to cause the drive output to actuate the engagement assembly from the disengaged state towards the engaged state, and determine a second position of the drive output that is associated with a second change in force applied by the drive output. The second change in force can be greater than the first threshold or a second threshold.

In some embodiments, the control circuitry is configured to identify a third position of the drive output that is associated with an intermediate state in which the actuator is disengaged from the elongate shaft, and based at least in part on the second position relative to the first position and the third position, determine whether or not the elongate shaft is properly received in the channel. Further, the control circuitry can be configured to, based at least in part on the determination of whether or not the elongate shaft is properly received in the channel, control the instrument feeder device.

In some embodiments, the control circuitry is configured to detect that at least one of (i) the instrument feeder device was coupled to a robotic system associated with the drive output, (ii) the medical instrument was coupled to the robotic system, (iii) a roll of the elongate shaft is instructed, or (iv) manual movement of a robotic arm of the robotic system is enabled. Further, the control circuitry can be configured to, based at least in part on the detection, cause the drive output to actuate the engagement assembly.

In some implementations, the present disclosure relates to a system comprising a medical instrument including an elongate shaft, an instrument feeder including an engagement assembly configured to receive the elongate shaft and to axially move the elongate shaft, and control circuitry. The instrument feeder is configured to couple to a robotic arm that includes a drive output. The control circuitry is configured to cause the drive output to actuate to move the engagement assembly and determine a state of the engagement assembly based on at least one of an amount of force applied by the drive output or a position of the drive output.

In some embodiments, the engagement assembly includes an actuator configured to axially move the elongate shaft and a channel configured to receive the elongate shaft. In examples, the instrument feeder device is configured to bias the actuator to an engaged state or a disengaged state. In examples, the state of the engagement assembly indicates whether the actuator is engaged with the elongate shaft. Further, in examples, the state of the engagement assembly indicates whether the elongate shaft is properly positioned within the channel.

In some embodiments, the control circuitry is configured to cause the drive output to actuate the engagement assembly from an engaged state in which the actuator is engaged to a disengaged state in which the actuator is disengaged, and determine a first position of the drive output that is associated with a first change in force applied by the drive output that occurred while moving the engagement assembly from the engaged state to the disengaged state.

In some embodiments, the control circuitry is configured to cause the drive output to actuate the engagement assembly from the disengaged state towards the engaged state and determine a second position of the drive output that is associated with a second change in force.

In some embodiments, the control circuitry is configured to, based at least in part on the second position relative to the first position, determine whether or not the elongate shaft is properly received in the channel, and based at least in part on the determination of whether or not the elongate shaft is properly received in the channel, control the instrument feeder device.

In some embodiments, the control circuitry is configured to, based at least in part on the second position relative to the first position, determine that the elongate shaft is at least one of not received in the engagement assembly or not properly received in the engagement assembly, and based at least in part on the determination that the elongate shaft is at least one of not received in the engagement assembly or not properly received in the engagement assembly, cause the drive output to actuate the engagement assembly to the disengaged state.

In some embodiments, the engagement assembly further includes a retention feature configured to selectively open or close the channel. The control circuitry can be configured to identify a third position of the drive output that is associated with an intermediate state in which the retention feature is closed and the actuator is disengaged from the elongate shaft, and based at least in part on the second position relative to the first position and the third position, determine that the elongate shaft is at least one of not received in the engagement assembly or not properly received in the engagement assembly. Further, the control circuitry can be configured to, based at least in part on the determination that the elongate shaft is at least one of not received in the engagement assembly or not properly received in the engagement assembly, cause the drive output to actuate the engagement assembly to the disengaged state.

In some implementations, the present disclosure relates to a method comprising controlling a drive output to cause actuation of an instrument feeder device that is configured to couple to a medical instrument, determining at least one of an amount of force applied by the drive output or a position of the drive output, and determining an engagement state of the instrument feeder device with the medical instrument based on at least one of the amount of force output by the drive output or the position of the drive output.

In some embodiments, the state of the instrument feeder device is determined based on at least one of a comparison of the amount of force applied by the drive output to one or more thresholds or a comparison of the position of the drive output to one or more reference positions.

In some embodiments, the engagement assembly includes an actuator configured to axially move the elongate shaft and a channel configured to receive the elongate shaft. In examples, the state of the instrument feeder device indicates at least one of whether or not the actuator is engaged with the elongate shaft or whether or not the elongate shaft is properly positioned within the channel.

In some embodiments, the method further comprises controlling the drive output to actuate the engagement assembly to a disengaged state in which the actuator is disengaged, determining a first position of the drive output that is associated with a first change in force applied by the drive output that occurred while moving the engagement assembly to the disengaged state, and controlling the drive output to actuate the engagement assembly from the disengaged state towards an engaged state in which the actuator is engaged. Further, the method can further comprise determining a second position of the drive output that is associated with a second change in force, and based at least in part on the second position relative to the first position, determining whether or not the elongate shaft is properly received in the channel.

In some embodiments, the method further comprises identifying a third position of the drive output that is associated with a state in which the actuator is disengaged from the elongate shaft and a retention feature of the engagement assembly is closed. The determination of whether or not the elongate shaft is received in the channel can be based at least in part on the second position relative to the first position and the third position.

In some implementations, the present disclosure relates to a robotic system comprising a robotic arm, an end effector associated with a distal end of the robotic arm, and control circuitry communicatively coupled to the robotic arm. The end effector includes a first drive output configured to actuate a first drive input of an instrument feeder to control engagement of the instrument feeder with an elongate shaft of an instrument. The control circuitry is configured to determine a state of the instrument feeder device based on at least one of an amount of force applied by the first drive output or a position of the first drive output.

In some embodiments, the end effector further includes a second drive output configured to actuate a second drive input of the instrument feeder to cause axial motion of the elongate shaft.

In some embodiments, the instrument feeder includes an actuator configured to axially move the elongate shaft, a channel configured to receive the elongate shaft, and a retention feature configured to selectively open or close the channel.

In some embodiments, the state of the instrument feeder device indicates at least one of whether or not the actuator is engaged with the elongate shaft, whether or not the retention feature is closed, or whether or not the elongate shaft is properly positioned within the channel.

In some embodiments, the control circuitry is configured to cause the instrument feeder to transition to a disengaged state in which the actuator is disengaged, cause the instrument feeder to move towards an engaged state, and determine a first position of the drive output that is associated with a first change in force applied by the first drive output that occurred while moving the instrument feeder towards the engaged state. Further, the control circuitry can be configured to identify a second position of the drive output that is associated with at least one of (i) a second change in force applied by the first drive output, or (ii) a state in which the actuator is disengaged from the elongate shaft and the retention feature is closed, and based at least in part on the first position relative to the second position, determine whether or not the elongate shaft is properly received in the channel.

For purposes of summarizing the disclosure, certain aspects, advantages and features are described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIG. 4 illustrates medical system components that may be implemented in any of the medical systems discussed herein in accordance with one or more embodiments.

FIGS. 8-1 and 8-2 illustrate a state in which rollers of an instrument feeder device are engaged and a cover is closed in accordance with one or more embodiments.

FIGS. 9-1 and 9-2 illustrate a state in which rollers of an instrument feeder device are engaged with an instrument shaft and a cover is closed in accordance with one or more embodiments.

FIGS. 10-1 and 10-2 illustrate a state in which rollers of an instrument feeder device are disengaged and a cover is closed in accordance with one or more embodiments.

FIGS. 11-1 and 11-2 illustrate a state in which rollers of an instrument feeder device are disengaged and a cover is open in accordance with one or more embodiments.

FIG. 14 illustrates an example process to determine a state of an engagement assembly of an instrument feeder device in accordance with one or more embodiments.

FIGS. 16-1 through 16-3 illustrate an example process to determine and/or remove slack in an elongate shaft of a medical instrument in accordance with one or more embodiments.

FIG. 17 illustrates an example process to determine and/or remove slack in an elongate shaft of a medical instrument in the context of inserting the elongate shaft in accordance with one or more embodiments.

FIGS. 18-1 and 18-2 illustrate an example process to determine and/or remove slack in an elongate shaft of a medical instrument in the context of enabling an admittance control mode and/or rolling the elongate shaft in accordance with one or more embodiments.

DETAILED DESCRIPTION

Figure 1:
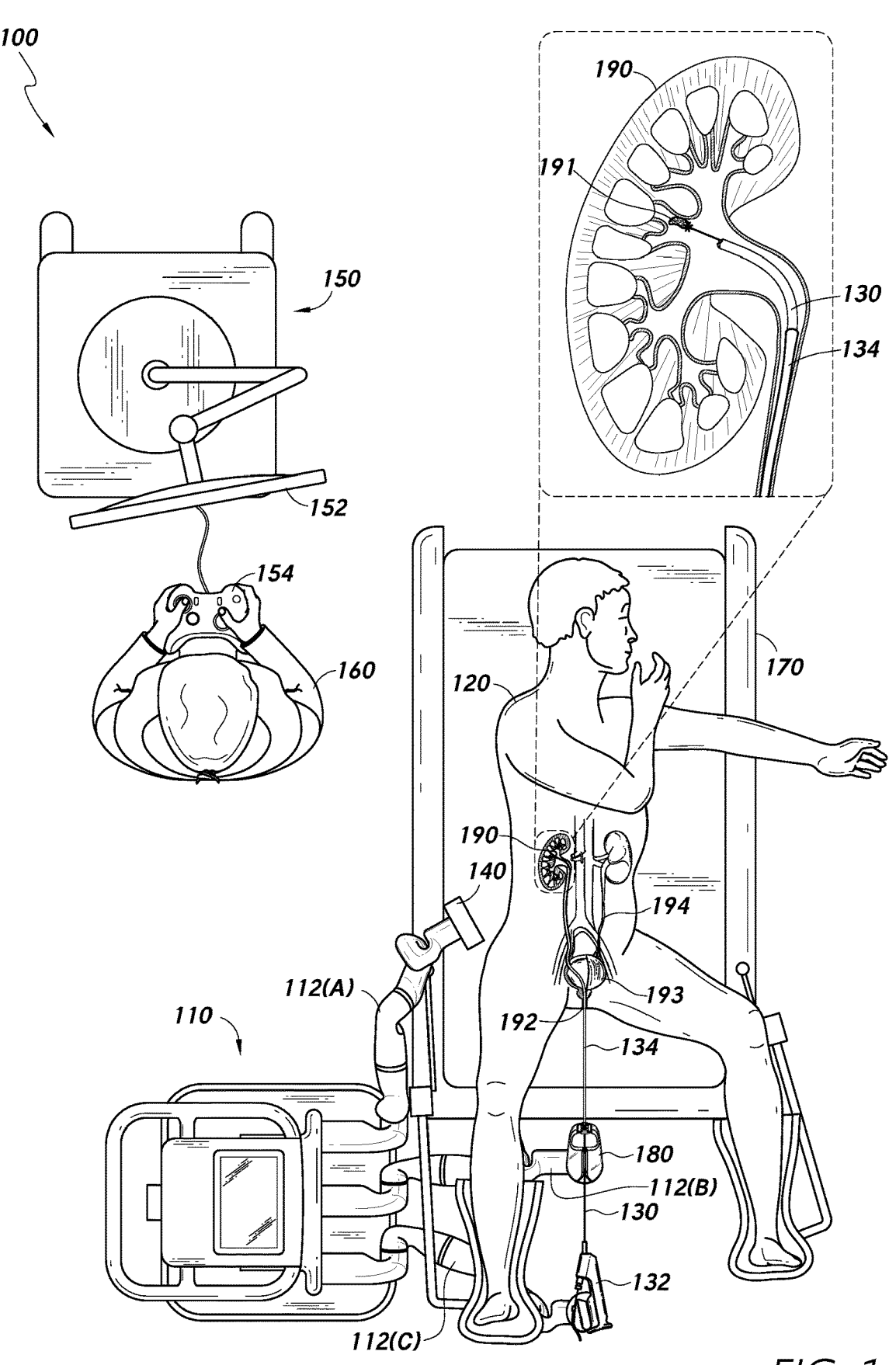
FIG. 1 illustrates an example robotic medical system arranged for a diagnostic and/or therapeutic ureteroscopy procedure in accordance with one or more embodiments.

Although certain embodiments and examples are disclosed below, the subject matter extends beyond the specifically disclosed embodiments to other alternative embodiments and/or uses and to modifications and equivalents thereof. Thus, the scope of the disclosure is not limited by any of the particular examples described below. For instance, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa. It should be understood that spatially relative terms, including those listed above, may be understood relative to a respective illustrated orientation of a referenced figure.

Certain reference numbers are re-used across different figures of the figure set of the present disclosure as a matter of convenience for devices, components, systems, features, and/or modules having features that are similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

Although certain aspects of the present disclosure are described in detail herein in the context of renal, urological, and/or nephrological procedures, such as kidney stone removal/treatment procedures, it should be understood that such context is provided for convenience, and the concepts disclosed herein are applicable to any suitable medical procedures, such as a bronchoscopy. However, description of the renal/urinary anatomy and associated medical issues and procedures is presented below to aid in the description of the concepts disclosed herein.

Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, uric acid, cystine, and/or other compounds or combinations thereof.

Several methods can be used for treating patients with kidney stones, including observation, medical treatments (such as expulsion therapy), non-invasive treatments (such as extracorporeal shock wave lithotripsy (ESWL)), minimally-invasive or surgical treatments (such as ureteroscopy and percutaneous nephrolithotomy ("PCNL")), etc. In some approaches (e.g., ureteroscopy and PCNL), the physician gains access to the stone, the stone is broken into smaller pieces or fragments, and the relatively small stone fragments/particulates are extracted from the kidney using a basketing device and/or aspiration.

In ureteroscopy procedures, a physician may insert a ureteroscope into the urinary tract through the urethra to remove urinary stones from the bladder and ureter. Typically, a ureteroscope includes an imaging device at its distal end configured to enable visualization of the urinary tract. The ureteroscope can also include a lithotripsy device to capture or break apart urinary stones. During a ureteroscopy procedure, one physician/technician may control the position of the ureteroscope, while another other physician/technician may control the lithotripsy device(s).

In PCNL procedures, which may be used to remove relatively large stones, a physician may insert a nephroscope through the skin (i.e., percutaneously) and intervening tissue to provide access to the treatment site for breaking-up and/or removing the stone(s). During PCNL procedures, fluidics can be applied to clear stone dust, small fragments, and/or thrombus from the treatment site and/or the visual field. In some instances, a relatively straight and/or rigid nephroscope is used, wherein the physician positions the tip of the nephroscope at the appropriate location within the kidney (e.g., calyx) by pushing/leveraging the device against the patient's body. This movement can be harmful to the patient (e.g., cause tissue damage).

In some procedures discussed herein, robotic tools can be implemented to enable a physician to obtain access to and/or treat a target anatomical site. For example, a medical system can be configured to engage with a medical instrument that includes an elongate shaft, such as a scope or another medical instrument. The medical system can be configured to control the medical instrument to perform a procedure, such as to remove a kidney stone from the patient and/or otherwise treat a target site. The medical system can include one or more robotic arms that are configured to couple to an instrument base/handle of the medical instrument and/or couple to the elongate shaft of the medical instrument.

In some instances, the medical system implements an instrument feeder device to assist in performing certain functions. The instrument feeder device can selectively engage with the elongate shaft of the medical instrument, control movement of the elongate shaft, and/or otherwise support the elongate shaft. For example, the instrument feeder device can facilitate axially motion of the elongate shaft (e.g., insert/retraction the shaft), retain the shaft during a roll of the shaft, retain the shaft during manual movement of a robotic arm, etc. To illustrate, the instrument feeder device can include one or more actuators configured to engage with the elongate shaft to axially move the elongate shaft during driving of the medical instrument. Further, the instrument feeder device can include a retention feature to retain the elongate shaft while still providing some freedom of movement of the elongate shaft, such as to roll the elongate shaft within the instrument feeder device, slide the elongate shaft through the instrument feeder device, etc. In many instances, the instrument feeder device can efficiently/quickly control movement of the elongate shaft, such as to insert or retract the elongate shaft, and/or provide anti-buckling support for the elongate shaft.

The instrument feeder device can generally be coupled to one robotic arm/component, while the instrument base of the medical instrument can generally be coupled to another robotic arm/component. In some examples, the instrument feeder device can be controlled in a correlated manner with movement of the instrument handle. For instance, to insert the shaft, the instrument feeder device can cause axial motion of the shaft in an insertion direction, while a robotic arm this is couped to the instrument handle moves closer to a robotic arm that is coupled to the instrument feeder device in a manner correlated to the speed of the axial motion. Similarly, to retract the shaft, the instrument feeder device can cause axial motion of the elongate shaft in a retraction direction, while a robotic arm that is couped to the instrument handle moves farther from the robotic arm that is coupled to the instrument feeder device in a manner correlated to the speed of the axial motion.

The present disclosure relates to, among other things, devices, systems, and methods for controlling an instrument feeder device to intelligently engage with and/or control a medical instrument. This can assist a physician in using the instrument feeder device and/or the medical instrument in different manners/scenarios. For example, a medical system be configured to control the instrument feeder device to implement various configurations/states to use the medical instrument, such as to load the medical instrument in the instrument feeder device, control movement of an elongate shaft of the medical instrument, enable a device/component of the medical system to be adjusted, etc. For instance, the medical system can cause the instrument feeder device to open/disengage at the appropriate time, so that a physician can load the elongate shaft into the instrument feeder device. Further, the medical system can cause the instrument feeder device to engage with the elongate shaft at the appropriate time, so that the medical system can drive/navigate the medical instrument, such as by inserting or retracting the elongate shaft. Moreover, the medical system can cause the instrument feeder device to disengage from and retain the elongate shaft at the appropriate time to facilitate certain actions, such as to roll the elongate shaft, freely move a robotic arm without experiencing resistance due to engagement of the elongate shaft with the instrument feeder device, etc.

Further, the present disclosure relates to devices, systems, and methods for determining a state of an instrument feeder device and/or a medical instrument with respect to the instrument feeder device. For example, a robotic arm can include a drive output configured to couple to and provide output to an instrument feeder device to control engagement with an elongate shaft of the medical instrument. A medical system can determine an engagement state of the instrument feeder device with the elongate shaft and/or a state of the medical instrument based on a force applied by the drive output, a position of the drive output, a sensor on the instrument feeder device, and/or in another manner. The state of the instrument feeder device/medical instrument can indicate if the medical instrument is loaded/properly loaded into the instrument feeder device, if the instrument feeder device is engaged with the medical instrument, if the instrument feeder device is configured to retain the medical instrument and allow freedom of movement of the medical instrument, etc. This can allow the medical system to confirm/determine that the instrument feeder device is implemented with the appropriate configuration/state and/or that the medical instrument is loaded/properly loaded at the appropriate time. For example, if it is determined that the medical instrument is properly loaded into the instrument feeder device, the medical system can proceed with driving/navigating the medical instrument. Further, if it is determined that the medical instrument is not loaded or not properly loaded (e.g., not placed within the appropriate position to facilitate driving of the shaft), the medical system can provide a notification/signal to notify a user/component of such state and/or wait to drive the medical instrument until the medical instrument is properly loaded.

As such, in examples, the medical systems discussed herein can be configured to control an instrument feeder device to intelligently engage with and/or control a medical instrument. For example, the medical system can place the instrument feeder device in the appropriate state at the appropriate time and/or confirm a state of the instrument feeder device/medical instrument. This can assist a physician in using the instrument feeder device and/or the medical instrument in different manners/scenarios, such as by enabling smooth workflow transitions to load/unload a medical instrument, to insert/retract the medical instrument, to adjust a position of a robotic arm or another component of a medical system, to roll the medical instrument, etc. In examples, the instrument feeder device can be controlled without receiving confirmation from a user regarding a state of the instrument feeder device/medical instrument. Further, by controlling and/or confirming a state of the instrument feeder device/medical instrument, the medical system can avoid/resolve issues associated with improperly loading the medical instrument (e.g., avoid a retention feature/cover from pinching the elongate shaft (which can damage the elongate shaft), avoid driving the elongate shaft with the elongate shaft improperly loaded (which can also damage the elongate shaft), etc.

Moreover, the present disclosure relates to devices, systems, and methods for evaluating and/or removing slack in an elongate shaft of the medical instrument. For example, as noted above, an instrument feeder device can be implemented to control the elongate shaft of the medical instrument. The instrument feeder device can generally be coupled to one robotic arm/component, while an instrument base of the medical instrument is generally coupled to another robotic arm/component. In some cases, the elongate shaft can include slack between the instrument base and the instrument feeder device, which may occur due to loading of the medical instrument, backlash/play in one or more components of the instrument feeder device/robotic arm/handle/ etc., a mismatch between actual backlash and software configured backlash, slippage of the instrument feeder device on the elongate shaft, etc. Such slack can cause undesirable issues. For example, if there is slack in the elongate shaft when the shaft is inserted, a curvature of the slack may increase as the instrument handle moves closer to the instrument feeder device, which can potentially damage the elongate shaft and/or cause other issues. Further, if there is slack in the elongate shaft when the instrument feeder device disengages from the elongate shaft (e.g., to initiate a roll of the elongate shaft, to enable manual movement of a robotic arm, and/or for other reasons), the elongate shaft may move in an insertion direction as the energy in the shaft is released. This can cause harm to a patient (e.g., due to a tip of the elongate shaft contacting tissue with a relatively high force). To prevent such issues, a medical system can determine if there is slack in the elongate shaft between the instrument handle and the instrument feeder device, and in some cases, remove/reduce the slack in the elongate shaft, if any.

A medical system can determine an amount of slack in the elongate shaft in a variety of manners. For example, the medical system can determine an amount of arm force applied by a robotic arm that is coupled to the instrument base of the medical instrument and/or determine an amount of drive output force applied by a drive output(s) of a robotic arm that is coupled to the instrument feeder device. The drive output(s) can be configured to control axially motion of the elongate shaft. The amount of arm force and/or drive output force can be used to determine if there is slack or tension in the elongate shaft. Additionally, or alternatively, the medical system can determine an amount of slack in the elongate shaft based on shape sensing data indicating a shape of the elongate shaft, position sensor data indicating a position of at least a portion of the elongate shaft, and/or other data.

In examples, the medical system can remove/reduce slack in the elongate shaft. For instance, the medical system can cause the robotic arm that is coupled to the instrument handle to move in a direction away from the robotic arm that is coupled to the instrument feeder device. This can occur without actively actuating the elongate shaft using the instrument feeder device. Alternatively, or additionally, the medical system can cause the instrument feeder device to move the elongate shaft in an insertion direction away from the instrument handle. This can occur without actively actuating the robotic arm that is coupled to the instrument handle. In some instances, the medical system can identify slack in the elongate shaft and/or remove such slack before and/or as part of performing certain functions, such as before disengaging the instrument feeder device from the elongate shaft, before rolling the elongate shaft, as part of inserting the elongate shaft, and/or in other situations.

As such, in examples, the medical systems discussed herein can be configured to intelligently evaluate slack in a medical instrument and/or remove such slack. This can prevent the elongate shaft from unintentionally moving in an insertion direction (e.g., when an instrument feeder device is disengaged from the shaft), which can cause harm to a patient. Further, evaluating and/or removing slack in the elongate shaft can avoid damaging the medical instrument (e.g., due to over bending the elongate shaft when too much slack is introduced between the instrument handle and the instrument feeder device). Moreover, interruptions in performing a procedure can be avoided (e.g., avoid a user from having to check for slack in the medical instrument, reload the medical instrument, etc.). For example, the medical system can evaluate and/or remove slack in the elongate shaft automatically at certain times before, during, or after a procedure. In some cases, the techniques can account for unknown sources that introduce slack into the elongate shaft.

Although various techniques are discussed in the context of implementing two robotic arms to couple to a medical instrument, the techniques can be implemented with multiple components that are included on a single robotic arm. For example, a robotic arm can include a first coupling element/robotic component to couple to an instrument feeder device and a second coupling element/robotic component to couple to an instrument handle, wherein the feeder device and the handle can be moved relative to each other, such as along a rail or other feature.

Further, although some techniques are discussed in the context of robotic-assisted medical procedures, the techniques may be applicable to other types of medical procedures, such as procedures that do not implement robotic tools or implement robotic tools for relatively few operations (e.g., less than a threshold number). For example, the techniques can be applicable to procedures in which a manually operated medical instrument is implemented, such as a manual catheter and/or scope controlled entirely by a physician.

Certain aspects of the present disclosure are described herein in the context of renal, urological, and/or nephrological procedures, such as kidney stone removal/treatment procedures. However, it should be understood that such context is provided for convenience, and the concepts disclosed herein are applicable to any suitable medical procedure. For example, the following description is also applicable to other surgical/medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, cataract removal, etc. However, as mentioned, description of the renal/urinary anatomy and associated medical issues and procedures is presented below to aid in the description of the concepts disclosed herein.

FIG. 1 illustrates an example robotic medical system 100 arranged for a diagnostic and/or therapeutic ureteroscopy procedure in accordance with one or more embodiments.

The medical system 100 includes a robotic system 110 configured to engage with and/or control one or more medical instruments/devices to perform a procedure on a patient 120. In the example of FIG. 1, the robotic system 110 couples to a scope 130 and an electromagnetic (EM) field generator 140. However, the robotic system 110 can couple to any type of device/instrument. The medical system 100 also includes a control system 150 configured to interface with the robotic system 110 and/or a physician 160, provide information regarding the procedure, and/or perform a variety of other operations. For example, the control system 150 can include a display(s) 152 configured to present certain information and/or an input/output (I/O) device 154 (a controller, in this example) configured to receive input from the physician 160, such as to control the robotic system 110. The medical system 100 can include a table 170 (e.g., bed) to hold the patient 120. Various acts are described herein as being performed by the physician 160. These acts can be performed directly by the physician 160, a user under the direction of the physician 160, another user (e.g., a technician), a combination thereof, and/or any other user. The devices/components of the medical system 100 can be arranged in a variety of ways depending on the type procedure, phase of the procedure, user preferences, etc.

The control system 150 can generally operate in cooperation with the robotic system 110 to perform the medical procedure. For example, the control system 150 can communicate with the robotic system 110 via a wireless or wired connection to control an instrument/device connected to the robotic system 110, receive an image(s) captured by a medical instrument, etc. For example, the control system 150 can receive image data from the scope 130 (e.g., an imaging device associated with the scope 130) and display the image data (and/or representations generated therefrom) via the display(s) 152 to assist the physician 160 in navigating the scope 130 and/or another instrument within the patient 120. The physician 160 can provide input via the I/O device 154 or another I/O device, and the control system 150 can send control signals to the robotic system 110 to control movement of the scope 130 connected to the robotic system 110. The scope 130 (and/or another medical instrument) can be configured to move in a variety of manners, such as to articulate, roll, etc.

In some embodiments, the control system 150 can provide power to the robotic system 110 via one or more electrical connections, provide optics to the robotic system 110 via one or more optical fibers or other components, etc. In examples, the control system 150 can communicate with a medical instrument to receive sensor data (via the robotic system 110 and/or directly from the medical instrument). Sensor data can indicate or be used to determine a position and/or orientation of the medical instrument. Further, in examples, the control system 150 can communicate with the table 170 to orient the table 170 or otherwise control the table 170. Moreover, in examples, the control system 150 can communicate with the EM field generator 140 to control generation of an EM field around the patient 120.

The robotic system 110 can include one or more robotic arms 112 configured to engage with and/or control a medical instrument(s)/device. Each robotic arm 112 can include multiple arm segments coupled to joints, which can provide multiple degrees of movement. A distal end of a robotic arm 112 (e.g., end effector) can be configured to couple to an instrument/device. In the example of FIG. 1, the robotic arm 112(A) is coupled to the EM field generator 140. The second robotic arm 112(B) is coupled to an instrument feeder device 180, which can facilitate robotic control/advancement of the scope 130. Further, the third robotic arm 112(C) is coupled to a handle 132 of the scope 130, which can be configured to facilitate advancement and/or operation of the scope 130 and/or a medical instrument that can be deployed through the scope 130, such as an instrument deployed through a working channel of the scope 130. In this example, the second robotic arm 112(B) and/or the third robotic arm 112(C) can control movement of the scope 130 (e.g., articulation, roll, etc.). Although three robotic arms are connected to particular instruments/devices in FIG. 1, the robotic system 110 can include any number of robotic arms that are configured to connect to any type of medical instrument/device.

The robotic system 110 can be communicatively coupled to any component of the medical system 100. For example, the robotic system 110 can be communicatively coupled to the control system 150 to receive a control signal from the control system 150 to perform an operation, such as to control a robotic arm 112 in a particular manner, manipulate an instrument/device, etc. Further, the robotic system 110 can be configured to receive an image (also referred to as image data) from the scope 130 depicting internal anatomy of the patient 120 and/or send the image to the control system 150, which can then be displayed on the display(s) 152. Moreover, the robotic system 110 can be coupled to a component of the medical system 100, such as the control system 150 and/or a fluid management system, in a manner as to allow for fluids, optics, power, or the like to be received therefrom.

A medical instrument can include a variety of types of instruments, such as a scope (sometimes referred to as an "endoscope"), a catheter, a needle, a guidewire, a lithotripter, a basket retrieval device, forceps, a vacuum, a needle, a scalpel, an imaging probe, an imaging device, jaws, scissors, graspers, needle holder, micro dissector, staple applier, tacker, suction/irrigation tool, clip applier, etc. A medical instrument can include a direct entry instrument, percutaneous entry instrument, and/or another type of instrument. In some embodiments, a medical instrument is a steerable device, while in other embodiments a medical instrument is a non-steerable device. In some embodiments, a surgical tool refers to a device that is configured to puncture or to be inserted through the human anatomy, such as a needle, a scalpel, a guidewire, etc. However, a surgical tool can refer to other types of medical instruments.

The term "scope" or "endoscope" can refer to any type of elongate medical instrument having image generating, viewing, and/or capturing functionality (or configured to provide such functionality with an imaging device deployed though a working channel) and configured to be introduced into any type of organ, cavity, lumen, chamber, and/or space of a body. For example, a scope or endoscope, such as the scope 130, can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, etc. A scope/endoscope, in some instances, may comprise a rigid or flexible tube and/or may be dimensioned to be passed within an outer sheath, catheter, introducer, or other lumen-type device, or may be used without such devices. In some embodiments, a scope includes one or more working channels through which additional tools/medical instruments, such as lithotripters, basketing devices, forceps, laser devices, imaging devices, etc., can be introduced into a treatment site.

The terms "direct entry" or "direct access" can refer to any entry of instrumentation through a natural or artificial opening in a patient's body. For example, the scope 130 may be referred to as a direct access instrument, since the scope 130 enters into the urinary tract of a patient via the urethra.

The terms "percutaneous entry" or "percutaneous access" can refer to entry, such as by puncture and/or minor incision, of instrumentation through the skin of a patient and any other body layers necessary to reach a target anatomical location associated with a procedure (e.g., the calyx network of the kidney). As such, a percutaneous access instrument may refer to a medical instrument, device, or assembly that is configured to puncture or to be inserted through skin and/or other tissue/anatomy, such as a needle, scalpel, guidewire, sheath, shaft, scope, catheter, and the like. However, it should be understood that a percutaneous access instrument can refer to other types of medical instruments in the context of the present disclosure. In some embodiments, a percutaneous access instrument refers to an instrument/device that is inserted or implemented with a device that facilitates a puncture and/or minor incision through the skin of a patient. For example, a catheter may be referred to as a percutaneous access instrument when the catheter is inserted through a sheath/shaft that is inserted into the skin of a patient.

In some embodiments, a medical instrument includes a sensor (also referred to as a "position sensor") that is configured to generate sensor data. In examples, sensor data can indicate a position and/or orientation of the medical instrument and/or can be used to determine a position and/or orientation of the medical instrument. For instance, sensor data can indicate a position and/or orientation of a scope, which can indicate a roll of a distal end of the scope. A position and orientation of a medical instrument can be referred to as a pose of the medical instrument. A sensor can be positioned on a distal end of a medical instrument and/or any other location. In some embodiments, a sensor can provide sensor data to the control system 150, the robotic system 110, and/or another system/device to perform one or more localization techniques to determine/track a position/orientation of a medical instrument.

In some implementations, a sensor can include an electromagnetic (EM) sensor with a coil of conductive material. Here, an EM field generator can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a sensor can include another type of sensor, such as a camera, a range sensor (e.g., depth sensor), a radar device, a shape sensing fiber, an accelerometer, a gyroscope, an accelerometer, a satellite-based positioning sensor (e.g., a global positioning system (GPS)), a radio-frequency transceiver, etc.

In some embodiments, the medical system 100 can also include an imaging device (not illustrated in FIG. 1) which can be integrated into a C-arm and/or configured to provide imaging during a procedure, such as for a fluoroscopy-type procedure. The imaging device can be configured to capture/generate one or more images of the patient 120 during a procedure, such as one or more x-ray or CT images. In examples, images from the imaging device can be provided in real-time to view anatomy and/or medical instruments within the patient 120 to assist the physician 160 in performing a procedure. The imaging device can be used to perform a fluoroscopy (e.g., with a contrast dye within the patient 120) or another type of imaging technique.

Further, in some embodiments, the medical system 100 can also include a fluid management system (sometimes referred to as "an aspiration system" or "an irrigation system") configured to control/provide aspiration and/or irrigation to a target site, such as via a catheter, the scope 130, an instrument/device associated with the catheter/scope (e.g., one or more access sheaths), and/or another instrument/device. The fluid management system can be configured to hold one or more fluid bags/containers and/or control fluid flow thereto/therefrom. In examples, the fluid management system includes certain electronic components, such as a display, flow control mechanics, and/or control circuitry. The fluid management system may comprise a stand-alone tower/cart. The fluid management system may include a pump with which aspiration fluid may be pulled into a collection container/cartridge via an aspiration channel/tube coupled to a catheter/scope.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), body area networks (BANs), cellular networks, the Internet, etc. Further, in some embodiments, the components of the medical system 100 are connected for data communication, fluid/gas exchange, power exchange, etc., via one or more support cables, tubes, or the like.

In some examples, the medical system 100 is implemented to perform a medical procedure relating to the renal anatomy, such as to treat kidney stones. For instance, robotic-assisted percutaneous procedures can be implemented, wherein robotic tools (e.g., one or more components of the medical system 100) can enable a physician/urologist to perform endoscopic (e.g., ureteroscopy) target access as well as percutaneous access/treatment. This disclosure, however, is not limited to kidney stone removal and/or robotic-assisted procedures. In some implementations, robotic medical solutions can provide relatively higher precision, superior control, and/or superior hand-eye coordination with respect to certain instruments compared to strictly manual procedures. For example, robotic-assisted percutaneous access to the kidney in accordance with some procedures can enable a urologist to perform both direct-entry endoscopic renal access and percutaneous renal access. Although some embodiments of the present disclosure are presented in the context of catheters, nephroscopes, ureteroscopes, and/or the human renal anatomy, it should be understood that the principles disclosed herein may be implemented in any type of endoscopic/percutaneous procedure or another type of procedure.

In one illustrative and non-limiting procedure, the medical system 100 can be used to investigate a kidney 190 and/or remove a kidney stone 191. During setup for the procedure, the physician 160 can position the robotic arms 112 of the robotic system 110 in the desired configuration and/or attach the appropriate medical instruments. For example, the physician 160 can position the first robotic arm 112(A) near a treatment site and attach the EM field generator 140, which can assist in tracking a location of the scope 130 and/or other instruments/devices during the procedure. Further, the physician 160 can position the second robotic arm 112(B) between the legs of the patient 120 and attach the instrument feeder device 180, which can facilitate robotic control/advancement of the scope 130. In some instances, the physician 160 can insert a sheath/access instrument 134 into the urethra 192 of the patient 120, through the bladder 193, and/or up the ureter 194. The physician 160 can connect the sheath/access instrument 134 to the instrument feeder device 180. The sheath/access instrument 134 can include a lumen-type device configured to receive the scope 130, thereby assisting in inserting the scope 130 into the anatomy of the patient 120. However, in some embodiments the sheath/access instrument 134 is not used (e.g., the scope 130 is inserted directly into the urethra 192). The physician 160 can then insert the scope 130 into the sheath/access 134 instrument manually, robotically, or a combination thereof. The physician 160 can attach the handle 132 of the scope 130 to the third robotic arm 112(C), which can be configured to facilitate movement of the handle 132, operation of a basketing device/laser device/ another medical instrument deployed through the scope 130, and/or facilitate other functions.

The physician 160 can interact with the control system 150 to cause the robotic system 110 to advance and/or navigate the scope 130 into the kidney 190. For example, the physician 160 can navigate the scope 130 using the controller 154 or another I/O device to locate the kidney stone 191. The control system 150 can provide information via the display(s) 152 regarding the scope 130 to assist the physician 160 in navigating the scope 130, such as to view an image representation (e.g., a real-time image(s) captured by the scope 130). In some embodiments, the control system 150 can use localization techniques to determine a position and/or an orientation of the scope 130, which can be viewed by the physician 160 through the display(s) 152. Further, other types of information can also be presented through the display(s) 152 to assist the physician 160 in controlling the scope 130, such as x-ray images or other images of the internal anatomy of the patient 120.

Once at the site of the kidney stone 191 (e.g., within the calyx of the kidney 190), the scope 130 can be used to designate/tag a target location for a catheter to access the kidney 190 percutaneously. To minimize damage to the kidney 190 and/or the surrounding anatomy, the physician 160 can designate a papilla as the target location for entering the kidney 190 percutaneously. However, other target locations can be designated or determined. In some embodiments of designating the papilla, the physician 160 can navigate the scope 130 to contact the papilla, the control system 150 can use localization techniques to determine a location of the scope 130 (e.g., a location of the distal end of the scope 130), and the control system 150 can associate the location of the scope 130 with the target location. Further, in some embodiments, the physician 160 can navigate the scope 130 to be within a particular distance to the papilla (e.g., park in front of the papilla) and provide input indicating that the target location is within a field-of-view of the scope 130. The control system 150 can perform image analysis and/or other localization techniques to determine a location of the target location. Moreover, in some embodiments, the scope 130 can deliver a fiduciary to mark the papilla as the target location.

When the target location is designated, a catheter or other instrument can be inserted through a percutaneous access path into the patient 120 to reach the target site (e.g., rendezvous with the scope 130). For example, the EM field generator 140 can be removed and a catheter (not shown) can be connected to the first robotic arm 112(A). The physician 160 can interact with the control system 150 to cause the robotic system 110 to advance and/or navigate the catheter. Alternatively, or additionally, the catheter can be manually inserted and/or controlled, such as when the catheter is implemented as a manually-controllable catheter. The control system 150 can provide information via the display (s) 152 regarding the catheter to assist the physician 160 in navigating the catheter. For example, the display(s) 152 can provide image data from the perspective of the scope 130, wherein the image data may depict the catheter (e.g., when within the field-of-view of an imaging device of the scope 130). In some embodiments, a needle or another medical instrument is inserted into the patient 120 to create a percutaneous access path for the catheter to enter. Further, in some embodiments, a percutaneous-access device/assembly (e.g., one or more sheaths and/or shafts) is inserted into a path created by a needle or another instrument to provide an access path for the catheter to reach the target location. Here, the catheter can be inserted into the percutaneous-access device. The percutaneous-access device can provide irrigation to the target anatomy, while the catheter can provide aspiration (e.g., via a lumen in the catheter).

With the scope 130 and/or the catheter located at the target location, the physician 160 can use the scope 130 to break up the kidney stone 191 and/or use the catheter to extract pieces of the kidney stone 191 from the patient 120. For example, the scope 130 can deploy a tool (e.g., a laser, a cutting instrument, etc.) through a working channel to fragment the kidney stone 191 into pieces and the catheter can suck out the pieces from the kidney 190 through the percutaneous access path. The catheter can provide aspiration to maintain/hold the kidney stone 191 at a distal end of the catheter and/or at a relatively fixed position, while the scope 130 fragments the kidney stone 191 using a tool (e.g., laser), as shown in FIG. 1. A fluid management system can provide irrigation to the target site via a percutaneous-access device/assembly associated with the catheter and/or provide aspiration to the target site via the catheter (e.g., a lumen in the catheter 140).

Although various examples are discussed in the context of providing irrigation/aspiration via the catheter and/or a percutaneous-access device/assembly, irrigation fluid and/or aspiration may be provided to the treatment site (e.g., kidney) through another device, such as the scope 130, in some cases. Furthermore, irrigation and aspiration may or may not be provided through the same instrument(s). Where one or more of instruments provides the irrigation and/or aspiration functionality, one or more others of the instruments may be used for other functionality, such as breaking-up the object to be removed.

Further, although various example procedures are discussed in the context of implementing a robotically controlled catheter, the procedure can be implemented with a manually controllable catheter. For example, a catheter can include a manually controllable handle that is configured to be held/manipulated by the physician 160. The physician 160 can navigate the catheter by moving the handle and/or manipulating a manual actuator, which can result in articulation of a distal portion of the catheter.

The medical system 100 (and/or other medical systems discussed herein) can provide a variety of benefits, such as providing guidance to assist a physician in performing a procedure (e.g., instrument tracking, instrument navigation, instrument calibration, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous aspiration/irrigation to remove an object more efficiently (e.g., to remove a kidney stone), etc. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 150 and the robotic system 110, which can be independently movable. Such distribution of functionality and/or mobility can enable the control system 150 and/or the robotic system 110 to be placed at locations that are optimal for a particular medical procedure, which can maximize working area around the patient and/or provide an optimized location for a physician to perform a procedure.

Although various techniques/systems are discussed as being implemented as robotically-assisted procedures (e.g., procedures that at least partly use the medical system 100), the techniques/systems can be implemented in other procedures, such as in fully-robotic medical procedures, human-only procedures (e.g., free of robotic systems), etc. For example, the medical system 100 can be used to perform a procedure without a physician holding/manipulating a medical instrument and without a physician controlling movement of a robotic system/arm (e.g., a fully-robotic procedure that relies on relatively little input to direct the procedure). That is, medical instruments that are used during a procedure can each be held/controlled by components of the medical system 100, such as the robotic arms 112 of the robotic system 110.

Figure 2:
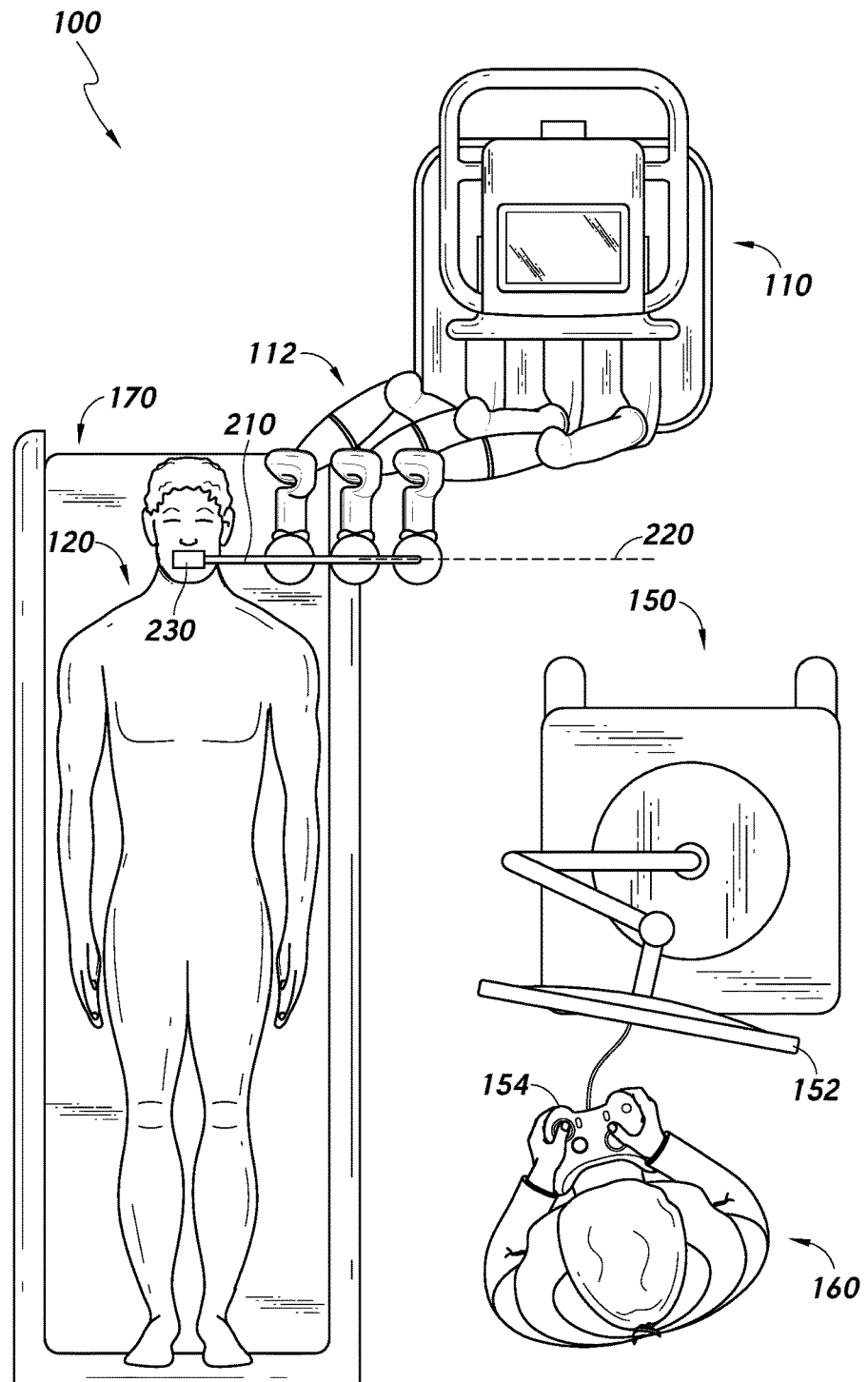
FIG. 2 illustrates the example robotic medical system of FIG. 1 arranged for a diagnostic and/or therapeutic bronchoscopy procedure in accordance with one or more embodiments.

FIG. 2 illustrates the example robotic medical system 100 arranged for a diagnostic and/or therapeutic bronchoscopy procedure in accordance with one or more embodiments. During a bronchoscopy, the arm(s) 112 of the robotic system 110 may be configured to deliver a medical instrument, such as a steerable endoscope 210 (also referred to as "the bronchoscope 210"), which may be a procedure-specific bronchoscope for bronchoscopy, to a natural orifice access point (i.e., the mouth of the patient 120 positioned on the table 170 in the present example) to deliver diagnostic and/or therapeutic tools. As shown, the robotic system 110 (e.g., cart) may be positioned proximate to the patient's upper torso in order to provide access to the access point. Similarly, the robotic arms 112 may be actuated to position the bronchoscope 210 relative to the access point. The arrangement in FIG. 2 may also be utilized when performing a gastro-intestinal (GI) procedure with a gastroscope, a specialized endoscope for GI procedures.

Once the robotic system 110 is properly positioned, the robotic arms 112 may insert the steerable endoscope 210 into the patient robotically, manually, or a combination thereof. The steerable endoscope 210 may comprise at least two telescoping parts, such as an inner leader portion and an outer sheath portion, with each portion coupled to a separate instrument driver from a set of instrument drivers and/or with each instrument driver coupled to the distal end of a respective robotic arm 112. This linear arrangement of the instrument drivers creates a "virtual rail" 220 that may be repositioned in space by manipulating the one or more robotic arms 112 into different angles and/or positions. The virtual rails/paths described herein are depicted in the figures using dashed lines that generally do not depict any physical structure of the system. Translation of one or more of the instrument drivers along the virtual rail 220 can advance or retract the endoscope 210 from the patient 120.

The endoscope 210 may be directed down the patient's trachea and lungs after insertion using precise commands from the robotic system 110 until reaching the target operative site. The use of separate instrument drivers can allow independent driving of separate portions of the endoscope/assembly 210. For example, the endoscope 210 may be directed to deliver a biopsy needle to a target, such as, for example, a lesion or nodule within the lungs of a patient. The needle may be deployed down a working channel that runs the length of the endoscope 210 to obtain a tissue sample to be analyzed by a pathologist. Depending on the pathology results, additional tools may be deployed down the working channel of the endoscope 210 for additional biopsies. For example, when a nodule is identified as being malignant, the endoscope 210 may endoscopically deliver tools to resect the potentially cancerous tissue. In some instances, diagnostic and therapeutic treatments can be delivered in separate procedures. In those circumstances, the endoscope 210 may also be used to deliver a fiducial to "mark" the location of the target nodule as well. In other instances, diagnostic and therapeutic treatments may be delivered during the same procedure.

In the arrangement of the system 100 in FIG. 2, a patient introducer 230 is attached to the patient 120 via a port (not shown; e.g., surgical tube). The patient introducer 230 may be secured to the table 170 (e.g., via a patient introducer holder configured to support the introducer 230 and secure the position of the patient introducer 230 with respect to the table 170 or other structure). In some embodiments, the patient introducer 230 may include a proximal end, a distal end, and an introducer tube therebetween. The proximal end of the patient introducer 230 can provide an opening/orifice which may be configured to receive the instrument 210 (e.g., bronchoscope), and the distal end of the patient introducer 230 can provide a second opening which may be configured to guide the instrument 210 into the patient-access port. A curved tube component of the introducer 230 can connect the proximal and distal ends thereof and guide the instrument 210 through the introducer 230.

The curvature of the introducer 230 may enable the robotic system 110 to manipulate the instrument 210 from a position that is not in direct axial alignment with the patient-access port, thereby allowing for greater flexibility in the placement of the robotic system 110 within the room. Further, the curvature of the introducer 230 may allow the robotic arms 112 of the robotic system 110 to be substantially horizontally aligned with the patient introducer 230, which may facilitate manual movement of the robotic arm(s) 112 if needed.

In some embodiments, one or more of the instrument feeder devices discussed herein can be implemented in a bronchoscopy procedure, such as that illustrated in FIG. 2. For example, an instrument feeder device can be implemented in cooperation with the endoscope 210 to control, at least in part, movement of the endoscope 210.

Figure 3:
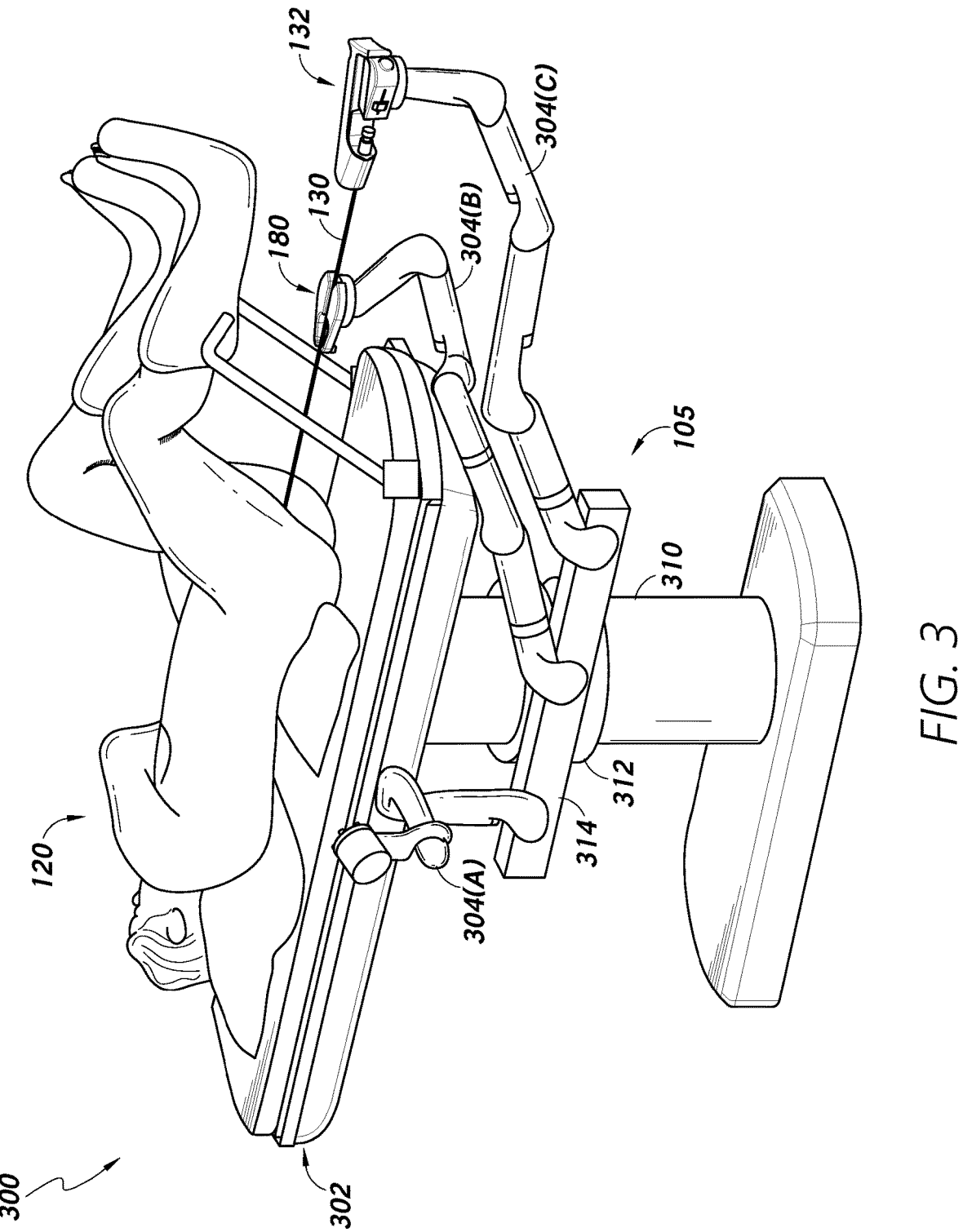
FIG. 3 illustrates a table-based robotic system configured to perform a medical procedure in accordance with one or more embodiments.

FIG. 3 illustrates a table-based robotic system 300 configured to perform a medical procedure in accordance with one or more embodiments. Here, one or more of the robotic components of the robotic medical system 100 can be incorporated into a table 302, which can reduce the amount of capital equipment within an operating room and/or allow greater access to the patient 120, in comparison to cart-based robotic systems. For example, the system 300 can include one or more components of the control system 150 and/or the robotic system 110.

As shown, the table 302 can include/incorporate one or more robotic arms 304 configured to engage with and/or control a medical instrument(s)/device. Each robotic arm 304 can include multiple arm segments coupled to joints, which can provide multiple degrees of movement. A distal end of a robotic arm 304 (i.e., end effector) can be configured to couple to an instrument/device, which can include any of the medical instruments/devices discussed herein, such as a catheter, needle, scope, etc. For example, the robotic arm 304(B) can be coupled to the instrument feeder device 180 and/or the robotic arm 304(C) can be coupled to the handle 132 of the scope 130, as shown in FIG. 3. Each robotic arm 304 can be similar to or different than the robotic arms 112 of the system 100 of FIGS. 1 and 2. Further, each end effector can be similar to or different than an end effector of the robotic system 110.

As shown, the robotic-enabled table system 300 can include a column 310 coupled to one or more carriages 312 (e.g., ring-shaped movable structures), from which the one or more robotic arms 304 may emanate. The carriage(s) 312 may translate along a vertical column interface that runs at least a portion of the length of the column 310 to provide different vantage points from which the robotic arms 304 may be positioned to reach the patient 120. The carriage(s) 312 may rotate around the column 310 in some embodiments using a mechanical motor positioned within the column 310 to allow the robotic arms 304 to have access to multiples sides of the table 302. Rotation and/or translation of the carriage(s) 312 can allow the system 300 to align the medical instruments, such as endoscopes and/or catheters, into different access points on the patient 120. By providing vertical adjustment, the robotic arms 304 can be configured to be stowed compactly beneath the platform of the table system 300 and subsequently raised during a procedure. The robotic arms 304 may be mounted on the carriage(s) 312 through one or more arm mounts 314, which may comprise a series of joints that may individually rotate and/or telescopically extend to provide additional configurability to the robotic arms 304. The column 310 structurally provides support for the table platform and a path for vertical translation of the carriage(s) 312. The column 310 may also convey power and control signals to the carriage(s) 312 and/or the robotic arms 304 mounted thereon.

In some embodiments, the table-based robotic system 300 can include or be associated with a control system, similar to the control system 150, to interface with a physician and/or provide information regarding a medical procedure. For example, a control system can include an input component(s) to enable a physician to control the one or more robotic arms 304 and/or medical instruments attached to the one or more robotic arms 304. In some implementations, the input component(s) enables the physician to provide input to control a medical instrument in a similar manner as if the physician were physically holding/manipulating the medical instrument.

FIG. 4 illustrates medical system components that may be implemented in any of the medical systems of FIGS. 1-3 in accordance with one or more embodiments of the present disclosure. Although certain components in FIG. 4, it should be understood that additional components not shown can be included in embodiments in accordance with the present disclosure. Furthermore, any of the illustrated components can be omitted, interchanged, and/or integrated into other devices/systems, such as the table 170, a medical instrument, etc.

The control system 150 can include one or more of the following components, devices, modules, and/or units (referred to herein as "components"), either separately/individually and/or in combination/collectively: control circuitry 401, one or more communication interfaces 402, one or more power supply units 403, one or more I/O components 404, one or more mobilization components 405 (e.g., casters or other types of wheels), and/or memory/data storage 406. In some embodiments, the control system 150 can comprise a housing/enclosure configured and/or dimensioned to house or contain at least part of one or more of the components of the control system 150. In this example, the control system 150 is illustrated as a cart-based system that is movable with the one or more mobilization components 405. In some cases, after reaching the appropriate position, the one or more mobilization components 405 can be immobilized using wheel locks to hold the control system 150 in place. However, the control system 150 can be implemented as a stationary system, integrated into another system/device, etc.

The various components of the control system 150 can be electrically and/or communicatively coupled using certain connectivity circuitry/devices/features, which may or may not be part of control circuitry. For example, the connectivity feature(s) can include one or more printed circuit boards configured to facilitate mounting and/or interconnectivity of at least some of the various components/circuitry of the control system 150. In some embodiments, two or more of the components of the control system 150 can be electrically and/or communicatively coupled to each other.

The one or more communication interfaces 402 can be configured to communicate with one or more devices/sensors/systems. For example, the one or more communication interfaces 402 can send/receive data in a wireless and/or wired manner over a network. In some embodiments, the one or more communication interfaces 402 can implement a wireless technology, such as Bluetooth, Wi-Fi, near field communication (NFC), or the like.

The one or more power supply units 403 can be configured to manage and/or provide power for the control system 150 (and/or the robotic system 110, in some cases). In some embodiments, the one or more power supply units 403 include one or more batteries, such as a lithium-based battery, a lead-acid battery, an alkaline battery, and/or another type of battery. That is, the one or more power supply units 403 can comprise one or more devices and/or circuitry configured to provide a source of power and/or provide power management functionality. Moreover, in some embodiments the one or more power supply units 403 include a mains power connector that is configured to couple to an alternating current (AC) or direct current (DC) mains power source.

The one or more I/O components/devices 404 can include a variety of components to receive input and/or provide output, such as to interface with a user to assist in performing a medical procedure. The one or more I/O components 404 can be configured to receive touch, speech, gesture, or any other type of input. In examples, the one or more I/O components 404 can be used to provide input regarding control of a device/system, such as to control the robotic system 110, navigate a scope/catheter or other medical instrument attached to the robotic system 110 and/or deployed through the scope, control the table 170, control a fluoroscopy device, etc. For example, a physician (not illustrated) can provide input via the I/O component(s) 404 and, in response, the control system 150 can send control signals to the robotic system 110 to manipulate a medical instrument. In examples, the physician can use the same I/O device to control multiple medical instruments (e.g., switch control between the instruments).

As shown, the one or more I/O components 404 can include the one or more displays 152 (sometimes referred to as "the one or more display devices 152") configured to display data. The one or more displays 152 can include one or more liquid-crystal displays (LCD), light-emitting diode (LED) displays, organic LED displays, plasma displays, electronic paper displays, and/or any other type(s) of technology. In some embodiments, the one or more displays 152 include one or more touchscreens configured to receive input and/or display data. Further, the one or more I/O components 404 can include one or more I/O devices/controls 407, which can include the controller 154 (e.g., hand-held controller, video-game-type controller, finger-based controls that enable finger-like movement, etc.), touch pad, mouse, keyboard, wearable device (e.g., optical head-mounted display), virtual or augmented reality device (e.g., head-mounted display), foot panel (e.g., buttons at the user's feet), etc. Additionally, the one or more I/O components 404 can include one or more speakers configured to output sounds based on audio signals and/or one or more microphones configured to receive sounds and generate audio signals. In some embodiments, the one or more I/O components 404 include or are implemented as a console.

In some embodiments, the one or more I/O components 404 can output information related to a procedure. For example, the control system 150 can receive real-time images that are captured by a scope and display the real-time images and/or visual/image representations of the real-time images via the display(s) 152. The display(s) 152 can present an interface(s), which can include image data from the scope and/or another medical instrument. Additionally, or alternatively, the control system 150 can receive signals (e.g., analog, digital, electrical, acoustic/sonic, pneumatic, tactile, hydraulic, etc.) from a medical monitor and/or a sensor associated with a patient, and the display(s) 152 can present information regarding the health or environment of the patient. Such information can include information that is displayed via a medical monitor including, for example, a heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, etc.

In some embodiments, the control system 150 can be coupled to the robotic system 110, a table 170 or another table, and/or a medical instrument, through one or more cables or connections (not shown). In some implementations, support functionality from the control system 150 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The robotic system 110 generally includes an elongate support structure 410 (also referred to as a "column"), a robotic system base 411, and a console 412 at the top of the column 410. The column 410 can include one or more carriages 413 (also referred to as "the arm support 413") for supporting the deployment of one or more the robotic arms 112. The carriage 413 can include individually configurable arm mounts that rotate along a perpendicular axis to adjust the base of the robotic arms 112 for positioning relative to a patient. The carriage 413 also includes a carriage interface 414 that allows the carriage 413 to vertically translate along the column 410. The carriage interface 414 can be connected to the column 410 through slots, such as slot 415, that are positioned on opposite sides of the column 410 to guide the vertical translation of the carriage 413. The slot 415 can include a vertical translation interface to position and/or hold the carriage 413 at various vertical heights relative to the base 411. Vertical translation of the carriage 413 allows the robotic system 110 to adjust the reach of the robotic arms 112 to meet a variety of table heights, patient sizes, physician preferences. etc. Similarly, the individually configurable arm mounts on the carriage 413 allow a robotic arm base 416 of the robotic arms 112 to be angled in a variety of configurations. The column 410 can internally comprise mechanisms, such as gears and/or motors, that are designed to use a vertically aligned lead screw to translate the carriage 413 in a mechanized fashion in response to control signals generated in response to user inputs, such as inputs from an I/O device(s).

The base 411 can balance the weight of the column 410, the carriage 413, and/or robotic arms 112 over a surface, such as the floor. Accordingly, the base 411 can house heavier components, such as one or more electronics, motors, power supply, etc., as well as components that enable movement and/or immobilize the robotic system 110. For example, the base 411 can include rollable wheels 417 (also referred to as "the casters 417" or "the mobilization components 417") that allow for the robotic system 110 to move around the room for a procedure. After reaching an appropriate position, the casters 417 can be immobilized using wheel locks to hold the robotic system 110 in place during the procedure. As shown, the robotic system 110 also includes a handle 418 to assist with maneuvering and/or stabilizing the robotic system 110. In this example, the robotic system 110 is illustrated as a cart-based system that is movable. However, the robotic system 110 can be implemented as a stationary system, integrated into a table, etc.

The robotic arms 112 can generally comprise robotic arm bases 416 and end effectors 419, separated by a series of linkages 420 (also referred to as "arm segments 420") that are connected by a series of joints 421. Each joint 421 can comprise an independent actuator and each actuator can comprise an independently controllable motor. Each independently controllable joint 421 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 419 at a specific position, orientation, and/or trajectory in space using different linkage positions and/or joint angles. In some embodiments, the end effectors 419 can be configured to engage with and/or control a medical instrument, a device, an object, etc. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

The end effector 419 of each of the robotic arms 112 can include an instrument device manipulator (IDM). In some embodiments, the IDM can be removed and replaced with a different type of IDM. For example, a first type of IDM can manipulate an endoscope, a second type of IDM can manipulate a catheter, a third type of IDM can hold an EM field generator, etc. However, the same IDM can be used. In some instances, an IDM can include connectors to transfer pneumatic pressure, electrical power, electrical signals, and/or optical signals to/from the robotic arm 112. The IDMs may be configured to manipulate medical instruments using techniques including, for example, direct drives, harmonic drives, geared drives, belts/pulleys, magnetic drives, and the like. In some embodiments, the IDMs can be attached to respective ones of the robotic arms 112, wherein the robotic arms 112 are configured to insert or retract the respective coupled medical instruments into or out of the treatment site.

In some embodiments, the robotic arms 112 can be configured to control a position, orientation, and/or articulation of a medical instrument attached thereto. For example, the robotic arms 112 can be configured/configurable to manipulate a scope/catheter using elongate movement members. The elongate movement members can include one or more pull wires, cables, fibers, and/or flexible shafts. To illustrate, the robotic arms 112 can be configured to actuate multiple pull wires of the scope/catheter to deflect the tip of the scope/catheter. Pull wires can include any suitable or desirable materials, such as metallic and/or non-metallic materials such as stainless steel, Kevlar, tungsten, carbon fiber, and the like. In some embodiments, the scope/catheter is configured to exhibit nonlinear behavior in response to forces applied by the elongate movement members. The nonlinear behavior can be based on stiffness and/or compressibility of the scope/catheter, as well as variability in slack or stiffness between different elongate movement members.

As shown, the console 412 is positioned at the upper end of column 410 of the robotic system 110. The console 412 can include a display(s) to provide a user interface for receiving user input and/or providing output (e.g., a dual-purpose device, such as a touchscreen), such as to provide a physician/user with pre-operative data, intra-operative data, information to configure the robotic system 110, etc. Potential pre-operative data can include pre-operative plans, navigation and mapping data derived from pre-operative computerized tomography (CT) scans, and/or notes from pre-operative patient interviews. Intra-operative data can include optical information provided from a tool, sensor and/or coordinate information from sensors, as well as vital patient statistics, such as respiration, heart rate, and/or pulse. The console 412 can be positioned and tilted to allow a physician to access the console 412 from the side of the column 410 opposite arm base 416. From this position, the physician may view the console 412, robotic arms 112, and patient while operating the console 412 from behind the robotic system 110.

The robotic system 110 can also include control circuitry 422, one or more communication interfaces 423, one or more power supply units 424, one or more input/output components 425, one or more actuators/hardware 426, and/or memory/data storage 427. The one or more communication interfaces 423 can be configured to communicate with one or more device/sensors/systems. For example, the one or more communication interfaces 423 can send/receive data in a wireless and/or wired manner over a network.

The one or more power supply units 424 can be configured to manage and/or provide power for the robotic system 110. In some embodiments, the one or more power supply units 424 include one or more batteries, such as a lithium-based battery, a lead-acid battery, an alkaline battery, and/or another type of battery. That is, the one or more power supply units 424 can comprise one or more devices and/or circuitry configured to provide a source of power and/or provide power management functionality. Moreover, in some embodiments the one or more power supply units 424 include a mains power connector that is configured to couple to an alternating current (AC) or direct current (DC) mains power source. Further, in some embodiments, the one or more power supply units 424 include a connector that is configured to couple to the control system 150 to receive power from the control system 150.

The one or more I/O components/devices 425 can be configured to receive input and/or provide output, such as to interface with a user. The one or more I/O components 425 can be configured to receive touch, speech, gesture, or any other type of input. In examples, the one or more I/O components 425 can be used to provide input regarding control of a device/system, such as to control/configure the robotic system 110. The one or more I/O components 425 can include the one or more displays configured to display data. The one or more displays can include one or more liquid-crystal displays (LCD), light-emitting diode (LED) displays, organic LED displays, plasma displays, electronic paper displays, and/or any other type(s) of technology. In some embodiments, the one or more displays include one or more touchscreens configured to receive input and/or display data. Further, the one or more I/O components 425 can include a touch pad, controller, mouse, keyboard, wearable device (e.g., optical head-mounted display), virtual or augmented reality device (e.g., head-mounted display), etc. Additionally, the one or more I/O components 425 can include one or more speakers configured to output sounds based on audio signals and/or one or more microphones configured to receive sounds and generate audio signals. In some embodiments, the one or more I/O components 425 include or are implemented as the console 412. Further, the one or more I/O components 425 can include one or more buttons that can be physically pressed, such as a button on a distal end of a robotic arm 112 (which can enable/disable an admittance control mode of the robotic arm 112 for manual manipulation/movement of the robotic arm 112).

The one or more actuators/hardware 426 can be configured to facilitate movement of the robotic arms 112. Each actuator 426 can comprise a motor, which can be implemented in a joint or elsewhere within a robotic arm 112 to facilitate movement of the joint and/or a connected arm segment/linkage. In some embodiments, a user can manually manipulate a robotic arm 112 without using electronic user controls. For example, during setup in a surgical operating room or at any point during a procedure, a user may select a button on a distal end of a robotic arm 112 to enable an admittance control mode and then manually move the robotic arm 112 to a particular orientation/position.

The various components of the robotic system 110 can be electrically and/or communicatively coupled using certain connectivity circuitry/devices/features, which may or may not be part of the control circuitry 422. For example, the connectivity feature(s) can include one or more printed circuit boards configured to facilitate mounting and/or inter-connectivity of at least some of the various components/ circuitry of the robotic system 110. In some embodiments, two or more of the components of the robotic system 110 can be electrically and/or communicatively coupled to each other.

As referenced above, the systems 150 and 110 can include the control circuitry 401 and 422, respectively, configured to perform certain functionality described herein. The term "control circuitry" can refer to any collection of one or more processors, processing circuitry, processing modules/units, chips, dies (e.g., semiconductor dies including one or more active and/or passive devices and/or connectivity circuitry), microprocessors, micro-controllers, digital signal processors, microcomputers, central processing units, graphics processing units, field programmable gate arrays, application specific integrated circuits, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

Although control circuitry is illustrated as a separate component from other components of the control system 150/robotic system 110, any or all of the other components of the control system 150/robotic system 110 can be embodied at least in part in the control circuitry. For instance, control circuitry can include various devices (active and/or passive), semiconductor materials and/or areas, layers, regions, and/or portions thereof, conductors, leads, vias, connections, and/or the like, wherein one or more of the other components of the control system 150/robotic system 110 and/or portion(s) thereof can be formed and/or embodied at least in part in/by such circuitry components/devices.

Further, the memory/data storage 406/427 can be configured to store data/instructions. For example, data storage/memory 406/427 can store instructions that are executable by control circuitry to perform certain functionality/operations. The term "memory" can refer to any suitable or desirable type of computer-readable media. For example, one or more computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data. One or more computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, one or more computer-readable media may not generally include communication media, such as modulated data signals and carrier waves. As such, one or more computer-readable media should generally be understood to refer to non-transitory media.

In some instances, the control system 150 and/or the robotic system 110 is configured to implement one or more localization techniques to determine/track an orientation/ position of an object/medical instrument. For example, the one or more localization techniques can process input data to generate position/orientation data for a medical instrument. Position/orientation data of an object/medical instrument can indicate a position/orientation of the object/medical instrument relative to a frame of reference. The frame of reference can be a frame of reference relative to anatomy of a patient, a known object (e.g., an EM field generator, system, etc.), a coordinate system/space, etc. In some implementations, position/orientation data can indicate a position/ orientation of a distal end of a medical instrument (and/or proximal end, in some cases). For example, position/orientation data for a scope can indicate a position and orientation of a distal end of the scope, including an amount of roll of the distal end of the scope. A position and orientation of an object can be referred to as a pose of the object.

Example input data that can be used to generate position/ orientation data for an object/medical instrument can include: sensor data from a sensor associated with a medical instrument (e.g., EM field sensor data, vision/image data captured by an imaging device/depth sensor/radar device on the medical instrument, accelerometer data from an accelerometer on the medical instrument, gyroscope data from a gyroscope on the medical instrument, satellite-based positioning data from a satellite-based sensor (a global positioning system (GPS), for example), etc.); feedback data from a robotic arm/component (also referred to as "kinematics data") (e.g., data indicating how a robotic arm/component moved/actuated); robotic command data for a robotic arm/ component (e.g., a control signal sent to the robotic system 110/robotic arm 112 to control movement of the robotic arm 112/medical instrument); shape sensing data from a shape sensing fiber (which can provide information regarding a location/shape of a medical instrument); model data regarding anatomy of a patient (e.g., a model of an interior/exterior portion of anatomy of the patient); position data of a patient (e.g., data indicating how the patient is positioned on a table); pre-operative data; etc.

Figure 5:
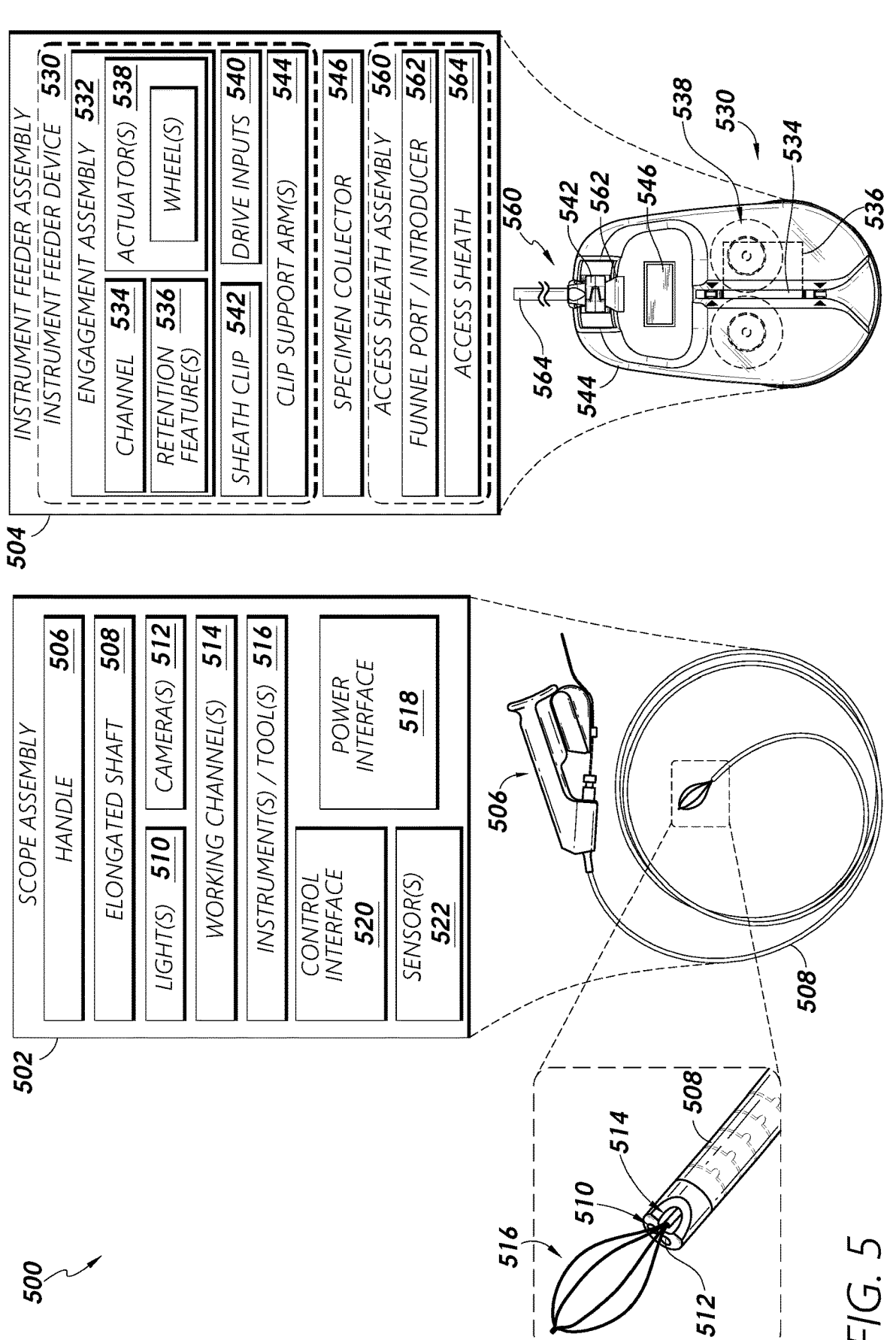
FIG. 5 illustrates medical system components, including a scope assembly/system and an instrument feeder assembly, that may be implemented in any of the medical systems discussed herein in accordance with one or more embodiments.

FIG. 5 illustrates medical system components, including a scope assembly/system 502 and an instrument feeder assembly 504, that may be implemented in any of the medical systems discussed herein in accordance with one or more embodiments. The scope system 502 and/or the feeder assembly 504 can include various hardware and control components. In examples, the scope system 502 can be representative of/include the scope 130 and/or other scopes discussed herein. Further, the instrument feeder assembly 504 can include the instrument feeder device 180 and/or any other instrument feeder device discussed herein.

As shown in FIG. 5, the scope system 502 includes a handle/instrument base 506 coupled to an elongate shaft 508. The handle 506 can be configured to couple to a robotic arm to be manipulated robotically and/or can be configured to be held by a user and manipulated manually (in some instances). For example, the handle 506 can be configured to control actuation of the elongate shaft 508. The elongate shaft 508 can include a rigid or flexible tube or another element. In some instances, the elongate shaft 508 and/or other components of the scope system 502 are dimensioned to be passed within an outer sheath, catheter, introducer, or other lumen-type device.

As shown, the scope system 502 can include one or more lights 510 disposed at least partially at a distal end of the elongate shaft 508 to provide light at the distal end. In examples, the scope system 502 can be configured to accommodate optical fibers to carry light from proximately located light sources, such as light-emitting diodes, to the distal end of the elongate shaft 508. The distal end of the elongate shaft 508 can include ports for light sources to illuminate an anatomical space, which may be useful when using an imaging device(s)/camera(s) 512. The scope system 502 can be implemented with any number of light sources.

The scope system 502 can also include the camera/ imaging device(s) 512 configured to capture image data, such as image data representing the internal anatomy of a patient. In examples, the imaging device 512 can include an optical fiber, fiber array, and/or lens. One or more optical components of the imaging device 512 can move along with the tip of the scope system 502 such that movement of the tip results in changes to the images captured by the imaging device 512. As such, the imaging device 512 can capture data from a distal end of the elongate shaft 508. In some embodiments, the scope system 502 can accommodate wires and/or optical fibers to transfer signals to/from an optical assembly and the distal end of the scope system 502.

The scope system 502 can also include a working channel (s) 514 for deploying an instrument(s)/tool(s) 516 and/or for other functions. Example instruments 516 include a laser device configured to provide a laser, a basketing device configured to capture/retrieve an object (e.g., a fragment of a kidney stone), forceps configured to grasp/hold an object, a scalpel configured to cut an object, lithotripters, an irrigation/aspiration device configured to provide irrigation/ aspiration to a target site, etc. In the example of FIG. 5, a basketing device is deployed through the working channel(s) 514. The working channel(s) 514 can extend longitudinally through the scope system 502 from a proximal end to the distal end. In examples, the working channel(s) 514 is offset to one side of the elongate shaft 508 (e.g., offset from a longitudinal axis), such as that illustrated in FIG. 5. In other examples, the working channel(s) 514 is positioned in the center of the scope system 502 or at another location. Although the imaging device(s) 512 is shown as being attached to the distal end of the scope system 502 (e.g., integral with the scope system 502), in some cases the imaging device(s) 512 is a separate device that is deployed through the working channel(s) 514. Further, although a single working channel 514 is shown, any number of working channels may be implemented.

In some instances, the scope system 502 can be powered through a power interface 518 and/or controlled through a control interface 520, each or both of which may interface with a robotic arm/component of the robotic system 110.

In some embodiments, the scope system 502 includes a sensor(s) 522 (sometimes referred to as a "position sensor") that is configured to generate and/or send sensor data to another device. The sensor data can indicate a position and/or orientation of the scope system 502 (e.g., the distal end thereof) and/or can be used to determine/infer a position/orientation of the scope system 502. For example, the sensor 522 can provide sensor data to a control system, which is then used to determine a position and/or an orientation of the scope system 502. The sensor 522 can be positioned on the distal end of the scope system 502 and/or another location. In some embodiments, the sensor 522 can include an electromagnetic (EM) sensor with a coil of conductive material, or another form/embodiment of an antenna. However, the scope system 502 can include other types of sensors, such as a shape sensing fiber, accelerometer (s), gyroscope(s), satellite-based positioning sensor(s) (e.g., global positioning system (GPS) sensors), radio-frequency transceiver(s), etc.

The scope system 502 can be articulable, such as with respect to at least a distal portion of the scope, so that the scope system 502 can be steered within the human anatomy. In some embodiments, the scope system 502 is configured to be articulated with, for example, five degrees of freedom (DOF), including XYZ coordinate movement, as well as pitch and yaw. Further, in some embodiments, the scope system 502 is articulatable with six DOF, including XYZ coordinate movement, as well as pitch, yaw, and roll. In other embodiments, the scope system 502 is articulable with other DOF. In embodiments where the scope system 502 is equipped with a position sensor, the position sensor can provide position information, such as 5-DOF position information (e.g., x, y, and z coordinates and pitch and yaw angles), 6-DOF position information (e.g., x, y, and z coordinate and pitch, yaw, and roll angles), etc. In some embodiments, the scope system 502 can include telescoping parts, such as an inner leader portion and an outer sheath portion, which can be manipulated to telescopically extend the scope system 502.

The scope system 502 can include one or more elongate movement members (not illustrated) that are configured to control movement of the elongate shaft 508, such as the distal end of the scope system 502. The elongate movement members may include one or more wires (e.g., pull or push wires), cables, fibers, and/or flexible shafts. Pull wires may include any suitable or desirable materials, such as metallic and non-metallic materials such as stainless steel, Kevlar, tungsten, carbon fiber, and the like. In some embodiments, the scope system 502 is configured to exhibit nonlinear behavior in response to forces applied by the elongate movement members. The nonlinear behavior may be based on stiffness and/or compressibility of the scope system 502, as well as variability in slack or stiffness between different elongate movement members. For robotic implementations, a robotic arm may be configured to actuate one or more pull wires coupled to the scope system 502 to deflect a tip of the elongate shaft 508. Alternatively, for user hand-held implementations, a user can provide manual input via an actuator to actuate one or more pull wires of the scope system 502 to deflect the tip of the elongate shaft 508.

FIG. 5 further illustrates the instrument feeder assembly 504 including an instrument feeder device 530 (sometimes referred to as "the instrument feeder 530") and an access sheath assembly 560, which may be physically coupled to the instrument feeder device 530.

The instrument feeder device 530 can include an engagement assembly 532 configured to engage with and/or control at least a portion of a shaft-type instrument, such as the scope 130 or the like. The engagement assembly 532 can include a channel 534 dimensioned and/or configured for placement therein of at least a portion of a shaft-type instrument. For example, when placing a scope or the like to allow for the instrument feeder device 530 to axially drive such instrument, the instrument may be nested at least partially within the channel 534. The engagement assembly 532 can also include a retention feature(s) 536 to maintain an instrument within the channel 534. For example, the retention feature(s) 536 can include a robotically-actuated cover that allows the channel 534 to be selectively opened or closed. Further, the engagement assembly 532 can include an actuator means/mechanism(s) 538 to axially move a shaft/instrument, such as when loaded with the channel 534. Although various components are illustrated as included within the engagement assembly 532, the engagement assembly 532 can include less or more components. In some instances, the instrument feeder device 530 is free of a sensor(s), such as a sensor to detect a state of the instrument feeder device 530, while in other instances the instrument feeder device 530 includes such sensor(s).

The actuator 538 can be configured to cause a shaft-type instrument placed in engagement therewith to be moved with respect to an axis of the instrument. In examples, the actuator(s) 538 includes one or more shaft-engagement wheels/rollers, conveyor belts, gears, tracks, finger-like/needle features, or other actuator(s). The actuator(s) 538 can be controlled through engagement with one or more drive inputs 540, which may allow for physical engagement with mechanical components of the instrument feeder device 530 that actuate the actuator means/mechanism 538 and/or may directly actuate the actuator means/mechanism 538. In one illustration, the actuator(s) 538 includes one or more feed rollers. As used herein, the term "feed roller" may include any number of roller(s)/wheel(s) configured to effect axial movement of a shaft engaged therewith. "Feed roller" may further include input or output drives associated with the instrument feeder device 530 that cause, directly or indirectly, movement of the roller(s)/wheel(s). In some embodiments, the rollers 538 can comprise or include a deformable material that provides grip, friction, traction, and/or pressure between the rollers 538 and the elongate shaft 508. The deformable material can include silicone rubber or another material.

The instrument feeder device 530 further includes a sheath coupling member/clip 542, which may be configured to secure or hold in place at least a portion of the access sheath assembly 560. For example, the sheath clip 542 may be configured to clamp on or over at least a portion of a funnel port structure 562 of the access sheath assembly 560, as shown. The clip 542 may be supported by one or more clip support arms 544. The sheath clip 542 can be positioned at a distal end of the instrument feeder device 530.

In some embodiments, the instrument feeder assembly 504 includes or is associated with a specimen collector structure 546, which may be secured at least in part to one or more components of the instrument feeder assembly 504. The specimen collector 546 may comprise a cup-like or other structure configured to allow for placement or dropping therein of a kidney stone or other specimen or debris retracted through the access sheath assembly 560, such as by using a basketing tool deployed through an instrument shaft. In some embodiments, the specimen collector 546 is disposed between the distal opening of the channel 534 and the funnel port structure 562, wherein an instrument (e.g., basketing device) may be retracted to a position over the specimen collector such that the stone/specimen may be dropped or placed in the specimen collector 546.

As shown, the access sheath assembly 560 can include an access sheath tube or conduit 564, which may be physically coupled at a proximal end thereof to the funnel port structure 562. The funnel port structure 562 can provide an at least partially conical introducer opening into the access sheath 564, wherein a proximal opening of the port 562 has an area or diameter greater than the cross-sectional area or diameter of the access sheath 564. In some embodiments, the access sheath 564 is not docked to the instrument feeder device 530, but rather coupled to a robot arm, a stand, or other structure. The access sheath 564 may comprise a tube or other structure through which the elongate shaft 508 can be inserted. In some embodiments, the access sheath 564 may comprise an elongate and flexible access sheath configured to be inserted into an anatomical lumen. In some embodiments, no access sheath is used and the elongated shaft 508 of the scope assembly 502 can be inserted directly into the patient (for example, through a natural patient orifice or other surgical access port or incision). Although certain examples described herein refer to access sheath assemblies including port/introducer structure and sheath components, it should be understood that embodiments of the present disclosure may implement access sheaths that have integrated port and sheath components. Therefore, references herein to an "access sheath," or simply "sheath," may refer to a sheath portion, port portion, or both, of an access sheath/assembly. Furthermore, access sheath assemblies described herein may be a unitary device, form, or structure, rather than an assembly of separate components.

Figure 6A:
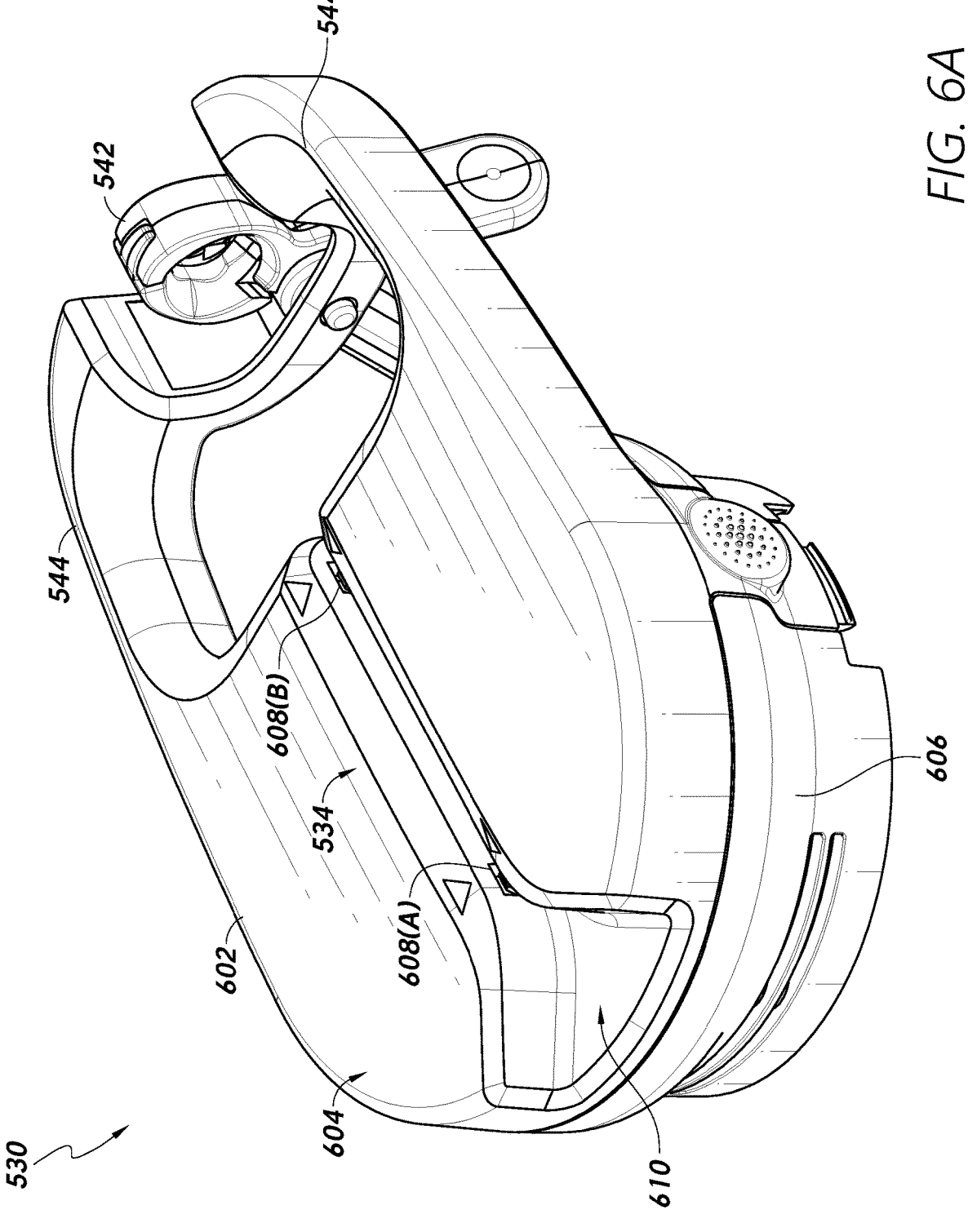
FIG. 6A illustrates a perspective view of an example instrument feeder device in accordance with one or more embodiments.
Figure 6B:
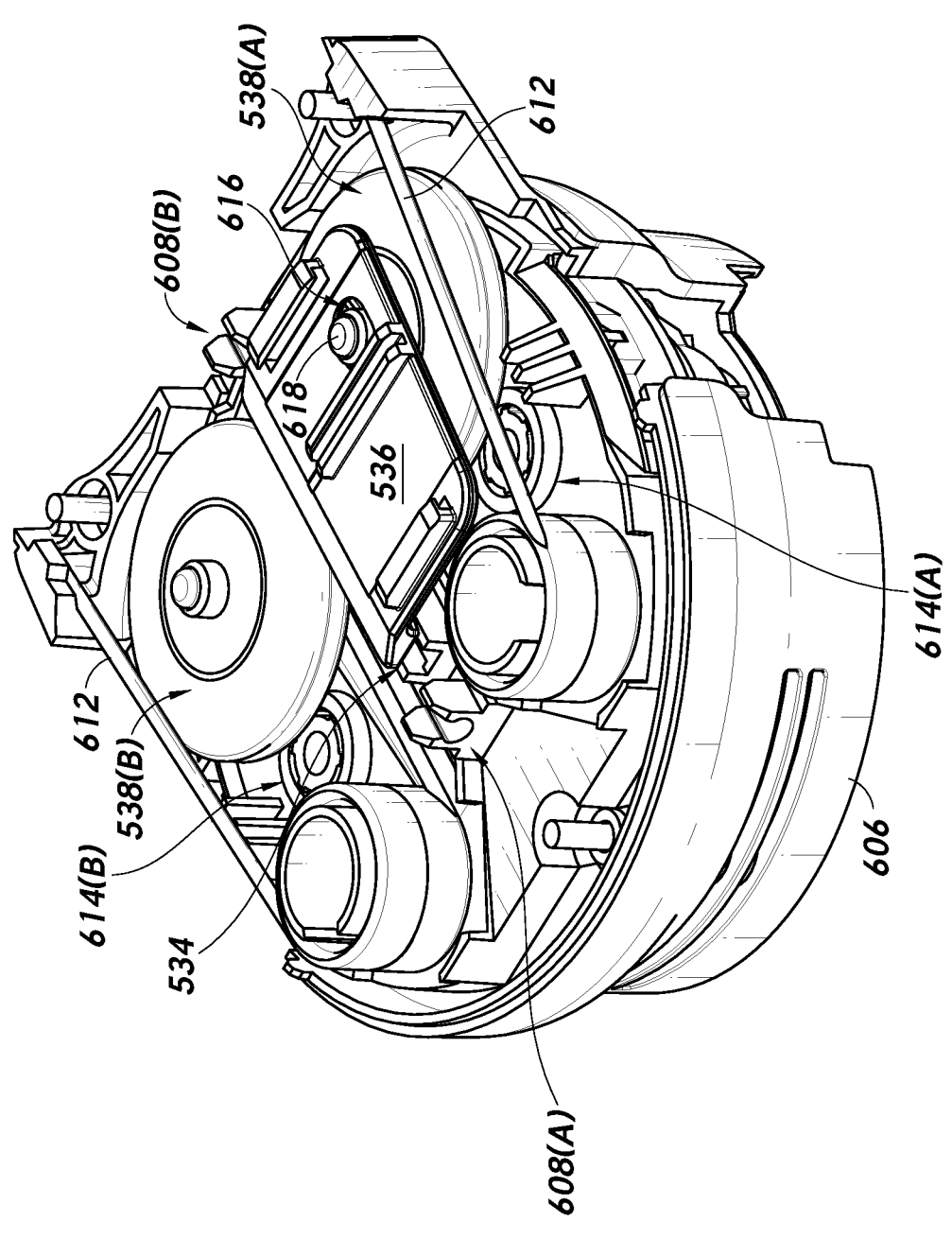
FIG. 6B illustrates the instrument feeder device with a portion of a housing removed to show various features of the instrument feeder device in accordance with one or more embodiments.
Figure 6C:
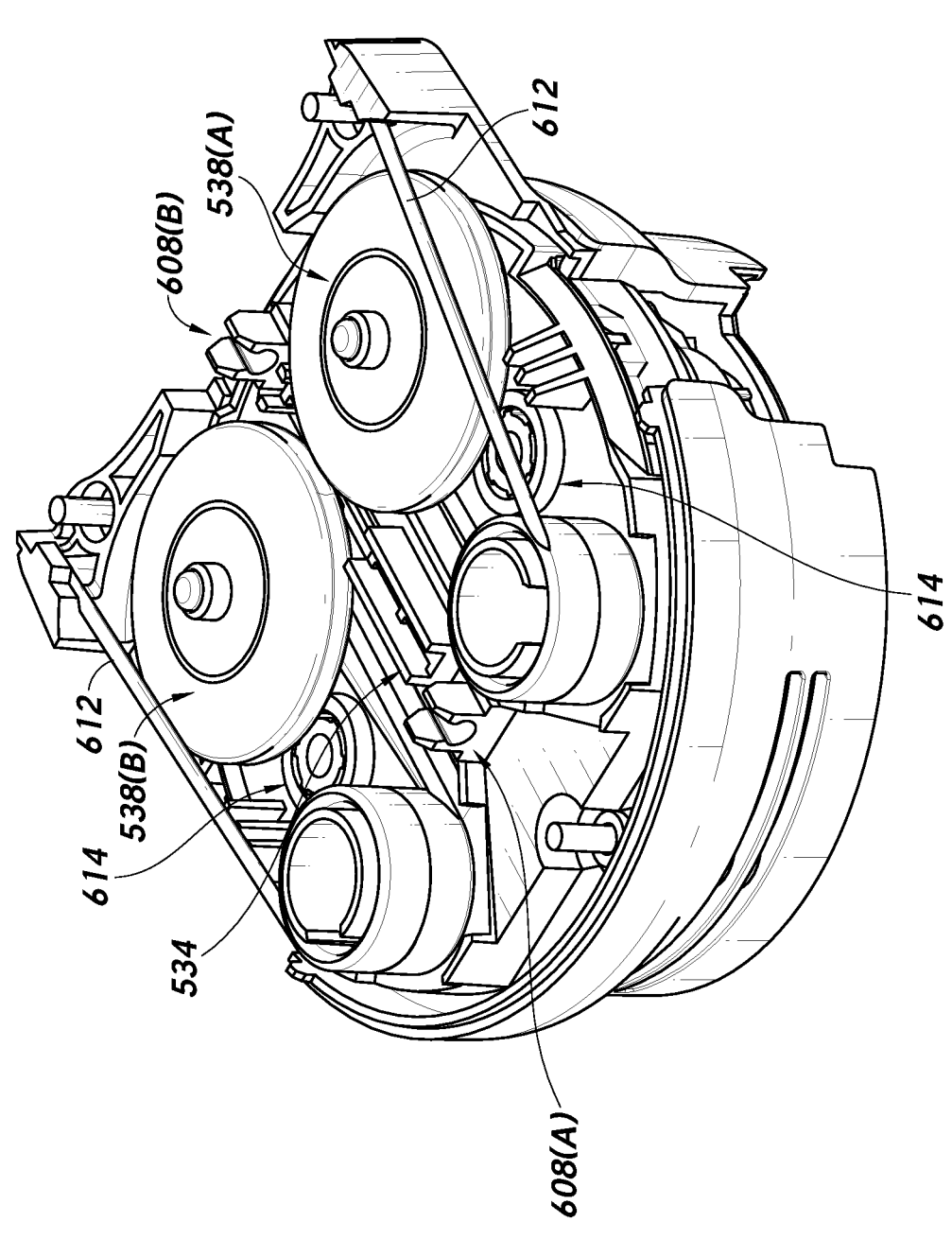
FIG. 6C illustrates the instrument feeder device with the portion of the housing and the retention feature(s) removed in accordance with one or more embodiments.

FIGS. 6A-6G illustrates example details of the instrument feeder device 530 in accordance with one or more embodiments. In particular, FIG. 6A illustrates a perspective view of the instrument feeder device 530, FIG. 6B illustrates the instrument feeder device 530 with a portion of a housing removed to show various features of the instrument feeder device 530, FIG. 6C illustrates the instrument feeder device 530 with the portion of the housing and the retention feature(s) 536 removed, and FIGS. 6D-6G illustrate example features/gears that can be implemented to facilitate movement of the rollers 538.

As shown in FIG. 6A, the instrument feeder device 530 can include a housing 602 configured to surround/enclose (either partially or fully) various internal components of the instrument feeder device 530. The housing 602 can include an upper portion 604 and a lower portion 606, wherein the lower portion 606 can be configured to attach to a robotic arm, sterile adapter, and/or other features/components. The upper portion 604 can include the channel 534 formed therein and configured to receive an instrument shaft. Such configuration can allow the instrument shaft to be loaded from the top and/or laterally into the instrument feeder device 530. The channel 534 can be dimensioned to receive the instrument shaft, such that the channel 534 generally has a larger width than an outer diameter of the instrument shaft. The C-shaped clip support arms 544 can be part of the housing 602 or separate components In some embodiments, the instrument feeder device 504 can include one or more clips/retention features 608 configured to secure an instrument shaft within the channel 534. For example, a first clip 608(A) can be positioned at a proximal end of the channel 534 and a second clip 608(B) can be positioned at a distal end of the channel 534. The clips can be configured to secure an instruments shaft without substantially restricting axial motion of the shaft through the channel 534. An inner diameter of a retaining portion of the clips 608 can generally be greater than an outside diameter of an instrument shaft. In some instances, the clips 608 can be configured to provide tactile feedback indicating to the user that an instrument shaft has been loaded properly into the channel 534, such as by snapping through an entry portion of the clips 608. In some instances, an instrument shaft can exhibit some amount of pivoting/tilting motion about the point at which the instrument shaft contacts the actuators, since the contact point can be relatively small. As such, the channel 534, clips 608, and/or other features of the instrument feeder device 504 can assist in maintaining the instrument shaft within the instrument feeder device 530 with the appropriate orientation. In some cases, the channel 534 can have a length that is sufficient to limit/prevent misalignment of the instrument shaft.

In the illustrated example, the channel 534 includes a flared or tapered portion 610, which can be positioned at the proximal end of the channel 534. In some instances, an instrument shaft (which can be relatively flexible) can form a service loop or other excessive slack between the instrument feeder device 530 and an additional robotic arm positioned coupled to an instrument base/handle associated with the instrument shaft. The tapered portion 610 can facilitate feeding of an instrument shaft into the instrument feeder device 530 at an angle and/or with a service loop, while avoiding a sharp bend in the instrument shaft. For example, the tapered portion 610 can provide a space for the elongate shaft to feed into the proximal end of the channel 534 at various angles, while sidewalls of the tapered portion 610 can provide an enlarged bend radius or smoothed out entry point for the instrument shaft at the region where the instrument shaft enters the instrument feeder device 530. The tapered portion 610 can also accommodate a degree of misalignment between the instrument feeder device 530 and the instrument base/handle associated with the instrument shaft. Further, the tapered portion 610 can facilitate feeding the shaft through the instrument feeder device 530 as the elongate shaft is driven axially.

As shown in FIGS. 6B and 6C, the instrument feeder device 530 can include the actuators 538, which are configured to drive axial motion of an instrument shaft. In this example, the actuators 538 are implemented as feed rollers; however, other types of actuators can be implemented. The rollers 538 can be positioned on opposing sides of the channel 534, such that the rollers 538 are positioned on opposing sides of the instrument shaft when the instrument shaft is loaded into the instrument feeder device 530. As such, the rollers 538 can be referred to as opposing rollers. The rollers can be configured to move between a first position generally associated with an engaged state, a second position generally associated with a disengaged state, and or other positions. For example, in the first position, the rollers 538 can press onto or otherwise engage with opposing/opposite sides of an instrument shaft and/or each other. In examples, when the rollers 538 are positioned in the first position, the rollers 538 can be rotated to drive insertion/retraction of the instrument shaft. Further, in examples, when the rollers 538 are positioned in the second position, the rollers 538 can be spaced apart from the instrument shaft and/or the channel 534. The second position can be associated with loading the instrument shaft, rolling the shaft, etc. Example states/positions of the rollers 538 and/or other features of the engagement assembly 532 are discussed in further detail below.

As shown in FIGS. 6B, the instrument feeder device 530 can include the retention feature(s) 536. In this example, the retention feature 536 is implemented as a cover; however, other retention features can be implemented. Here, the cover 536 is coupled/mechanically linked to one or more other features of the instrument feeder device, such as the roller 538(A). In examples, as the roller 538(A) moves between various positions/states (e.g., an engaged or disengaged state), the cover 536 can open or close automatically. As shown, the cover 536 can include a plate positioned over the roller 538(A). The cover 536 can include a slot 616 or other opening to receive/engage with a cam/shaft 618 which can extend from the roller 538(A). In this example, as the roller 538(A) moves, the cam 618 engages with the slot 616 to cause corresponding movement of the cover 536, such as opening/closing of the cover 536 along with movement of the roller 538(A). Although various examples are discussed in the context of the retention feature 536 being implemented as a cover, other features can be implemented. For example, the clips 608 can be configured to be selectively opened or closed in some instances to facilitate opening or closing of the channel 534. While the illustrated embodiments utilize a cam mechanism to open/close a sliding or translating cover, other mechanisms can be used to form an operative coupling between a drive input and the cover 536. Additionally, or alternatively, the cover 536 may be a pivoting cover or may be actuated open or closed with other movements.

In some embodiments, where the position of the cover 536 is mechanically linked to the position of the rollers 538 (as in the illustrated example), the cover 536 may be sufficiently long that it continues to close the channel 534 even as the rollers 538 first disengage from an instrument shaft. Then, as the rollers 538 continued to move away from the shaft, the cover 536 can continue to move, uncovering the channel 534. In other embodiments, the position of the cover 536 can be controlled by different methods. For example, the cover 536 need not be mechanically coupled to the roller 538(A). In some instances, the cover 536 is independently controlled and/or not mechanically linked to the roller 538(A), in which case fully opening, closing, or any other intermediate position of the cover 536 can be controlled by another drive input and/or in another manner. That is, in some instances the cover 536 is coupled to its own drive input.

The instrument feeder device 530 can further include one or more springs 612, which can be configured to apply forces to the rollers 538. In some examples, the springs 612 can bias the rollers 538 towards a particular position, such as a first position in which the rollers 538 are engaged (e.g., a closed/engaged state). Here, to move the rollers 538 to a second position in which the rollers 538 are disengaged, a drive output can provide/apply force to overcome the force of the springs 612. In examples, in addition to biasing the rollers 538 towards an engaged position, the springs 612 can also be configured to provide a pressure or friction force to cause the rollers 538 to engage with an instrument shaft. Thus, the spring force can be selected such that the rollers 538 begin to slip on an instrument shaft at a prescribed load. By tuning this drive/spring force, the system can maintain a level of applied force that is deemed or defined to be tolerable or safe for a patient. Although various examples are discussed in the context of the springs 612 biasing the rollers 538 towards a first position in which the rollers are engaged, the springs 612 can be configured to bias the rollers 538 towards a second position in which the rollers 538 are disengaged and/or to bias the rollers 538 to another position. In some instances, the one or more springs 612 are part of the engagement assembly 532.

In examples, the one or more springs 612 comprise mechanical springs, such as torsion springs. However, other types of springs can be implemented, such as coil springs or other types of springs. In the case of mechanical springs, the force of the springs 612 can be adjusted (to provide the safety feature described above) by adjusting the size of the springs 612 and/or the material from which the springs 612 are made. Additionally, various other parameters of the instrument feeder device 530 can be considered. For example, the material of the contact area of the rollers 538 can be adjusted up or to provide different coefficients of friction between an instrument shaft and the rollers 538. Similarly, the coefficient of friction of the instrument shaft can be adjusted. One or more of these parameters can be configured such that the rollers 538 slip relative to the instrument shaft to reduce or prevent the shaft from imparting too much force on the patient's anatomy. In some embodiments, the springs 612 can be omitted, and the instrument feeder device 530 can include virtual springs are controlled via operation of driveshafts or drive outputs to apply force against the instrument shaft. For example, instead of or in addition to including the springs 612, the drive inputs 540 can be operated in a manner to provide functionality similar to that of a mechanical spring, thus providing a virtual spring that can grip against the instrument shaft.

Figure 7:
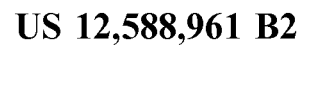
FIG. 7 illustrates an exploded view of an example instrument device manipulator assembly associated with a robotic arm in accordance with one or more embodiments.

In examples, the rollers 538 are coupled to drive shafts 614 to facilitate rotation of the rollers 538. For example, the drive shafts 614 can be coupled to the drive inputs 540 of the instrument feeder device 530 to receive input from a drive output of a robotic arm to control rotation of the rollers 538. The drive shafts 614 can be rotated to provide corresponding rotation at the rollers 538. In one illustration, the drive shaft 614(A) can be coupled to the drive input 540(A) and/or the drive shaft 614(B) can be coupled to the drive input 540(B) (as illustrated in FIG. 7). In examples, each of the rollers 538 can be independently driven. The rollers 538 can be connected to the drive inputs 540 and/or the drive shafts 614 through a direct connection and/or through a gear assembly, a belt drive system, and/or other means/mechanisms. Although two rollers 538 and two drive shafts 614 are illustrated in this example, any number of rollers and/or drive shafts can be implemented. For instance, a single drive shaft can be implemented to drive one or more rollers.

In examples, the rollers 538 operate in a cooperative relationship such that the rollers 538 move closer to each other or farther away from each other in a correlated manner. For example, each of the rollers 538 can be coupled to a carrier/support plate, wherein the two carrier plates are geared or otherwise coupled together, such that rotation of one carrier plate causes an opposite and corresponding rotation of the other carrier plate, as discussed in the example of FIGS. 6D-6G below. In this manner rotation of both carrier plates can be driven by a single open/close drive input, such as the drive input 540(C) (as illustrated in FIG. 7 and elsewhere). As such, in some instances, a single drive input can control the engagement assembly 532 of the instrument feeder device 530.

Figure 6D:
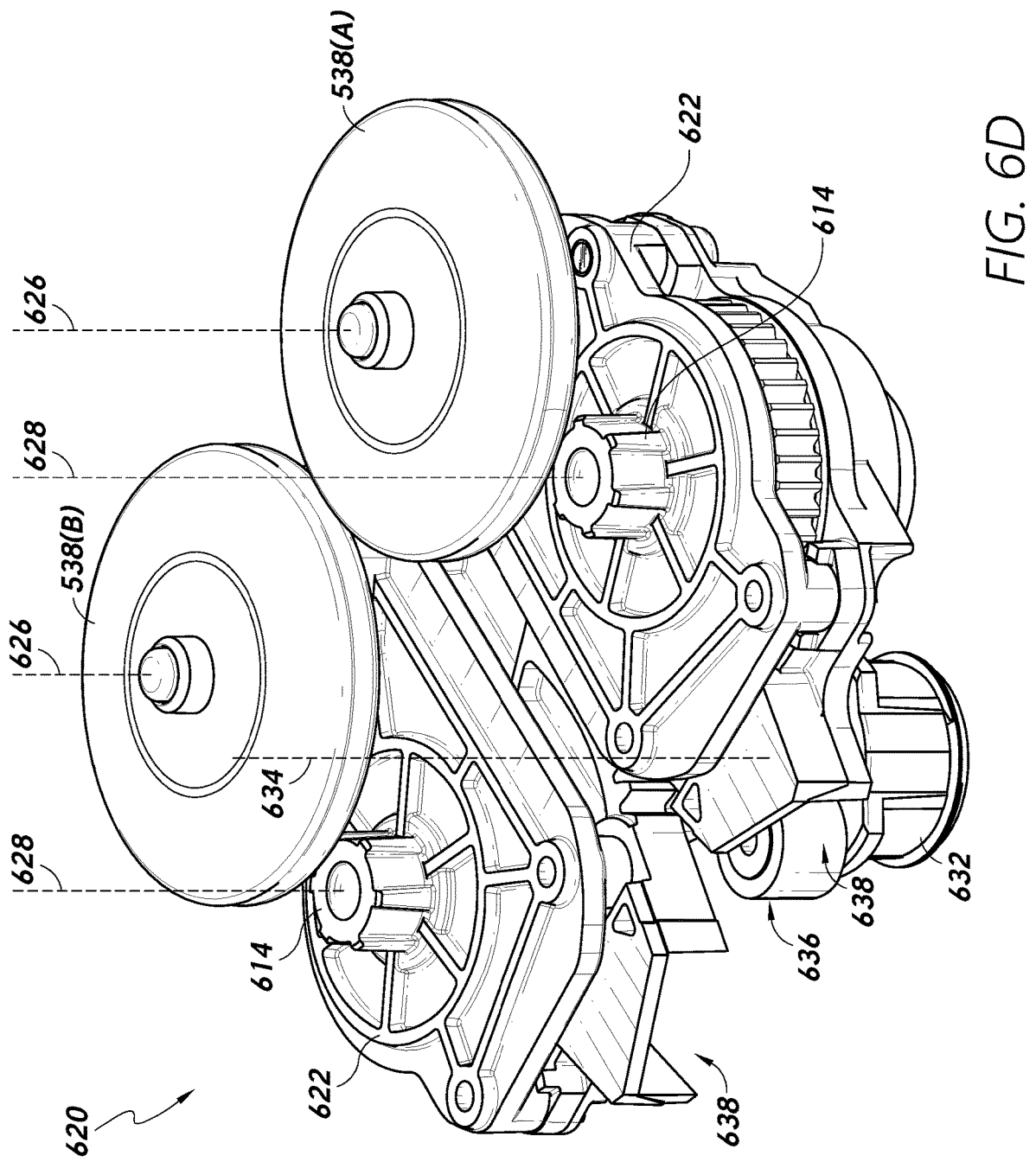
FIG. 6D illustrates a perspective view of an example actuator/roller assembly that can be implemented within the instrument feeder device in accordance with one or more embodiments.

FIG. 6D illustrates a perspective view of an example actuator/roller assembly 620 that can be implemented within the instrument feeder device 530 to facilitate movement of the rollers 538. This shows one of many example implementations. In the illustrated example, the roller assembly 620 includes right and left assemblies. Each of the right and left assemblies can include a carrier plate 622. The term plate can generally refer to a support structure, and the carrier plate 622 need not be considered necessarily flat or planar. Rather, the carrier plate 622 can comprise a variety of shapes and/or geometries configured to support various components of the roller assembly 620. The carrier plate 622 can also be referred to as a linkage or other supporting structure.

In general, the carrier plate 622 supports or is connected to various other features or structures of the roller assembly 620. For example, each carrier plate 622 can support or connect to one of the rollers 538 and one of the roller drive shafts 614. As shown in FIG. 6D, each roller 538 is configured to rotate about a roller axis 626. Each roller drive shaft 614 can be configured to rotate about a drive input axis 628. As illustrated, the roller axis 626 and the drive input axis 628 need not be coaxial. In some examples, the roller axis 626 and the drive input axis 628 are parallel (for example, as illustrated). The carrier plate 622 can also support or be connected to a gear assembly 630, as will be described below with reference to FIGS. 6E and 6F, which connects the roller drive shafts 614 to the rollers 538 such that rotation of the roller drive inputs 540(A), 540(B) can cause rotation of the rollers 538.

Figure 6E:
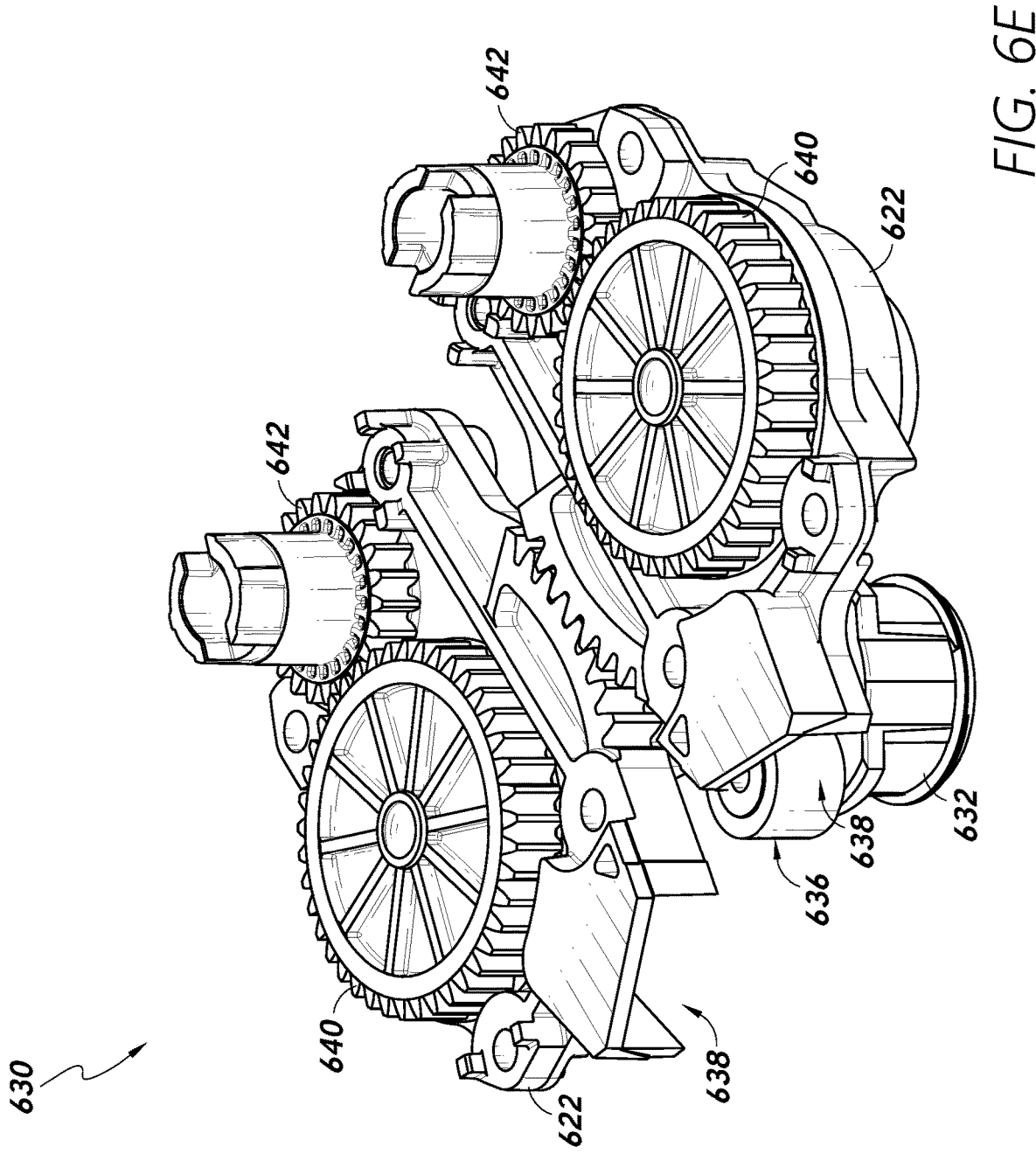
FIG. 6E illustrates a perspective view of the roller assembly with the rollers and a portion of the carrier plates removed to illustrate the example gear assemblies in accordance with one or more embodiments.
Figure 6F:
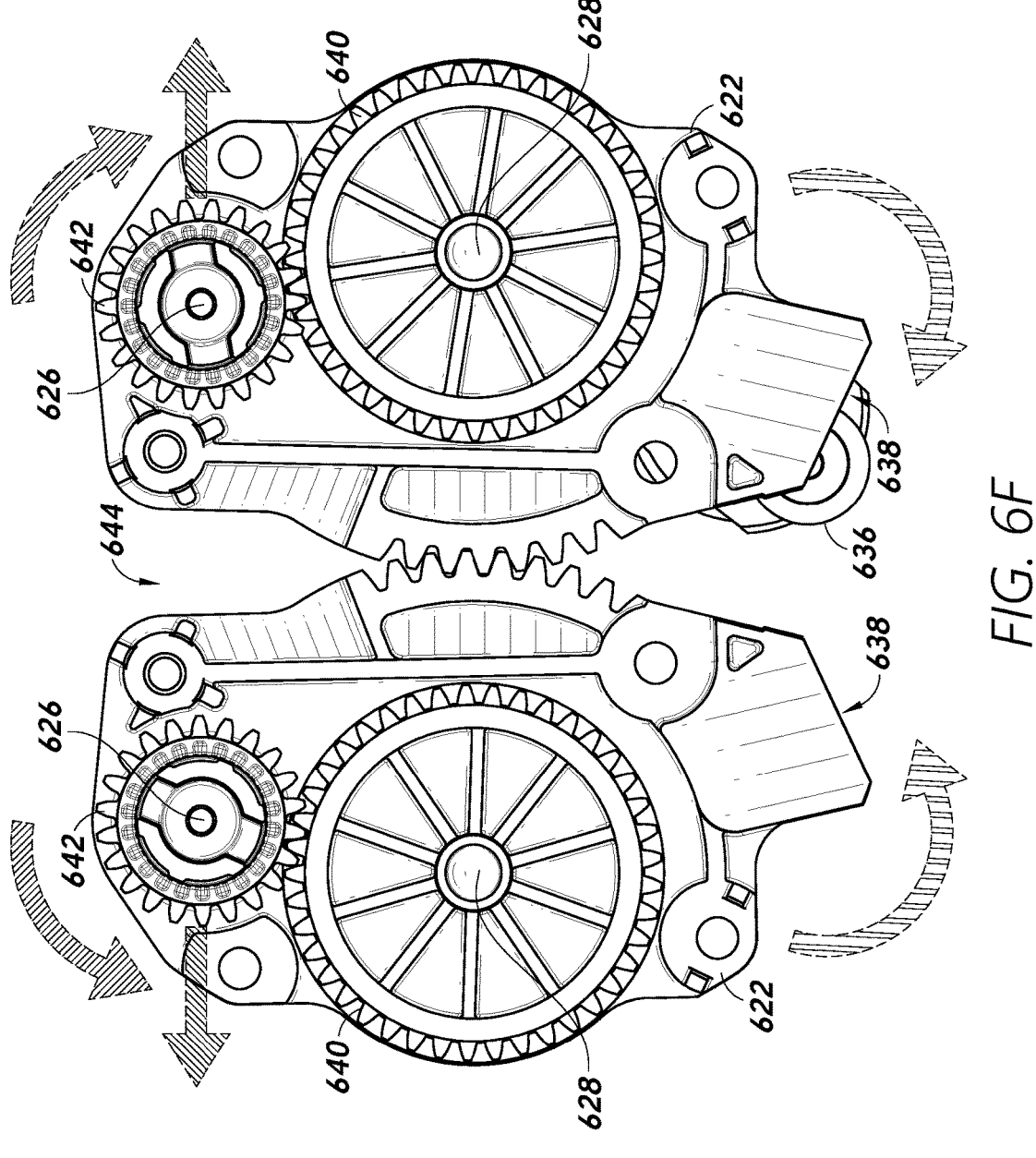
FIG. 6F illustrates a top view of the example gear assemblies in accordance with one or more embodiments.
Figure 6G:
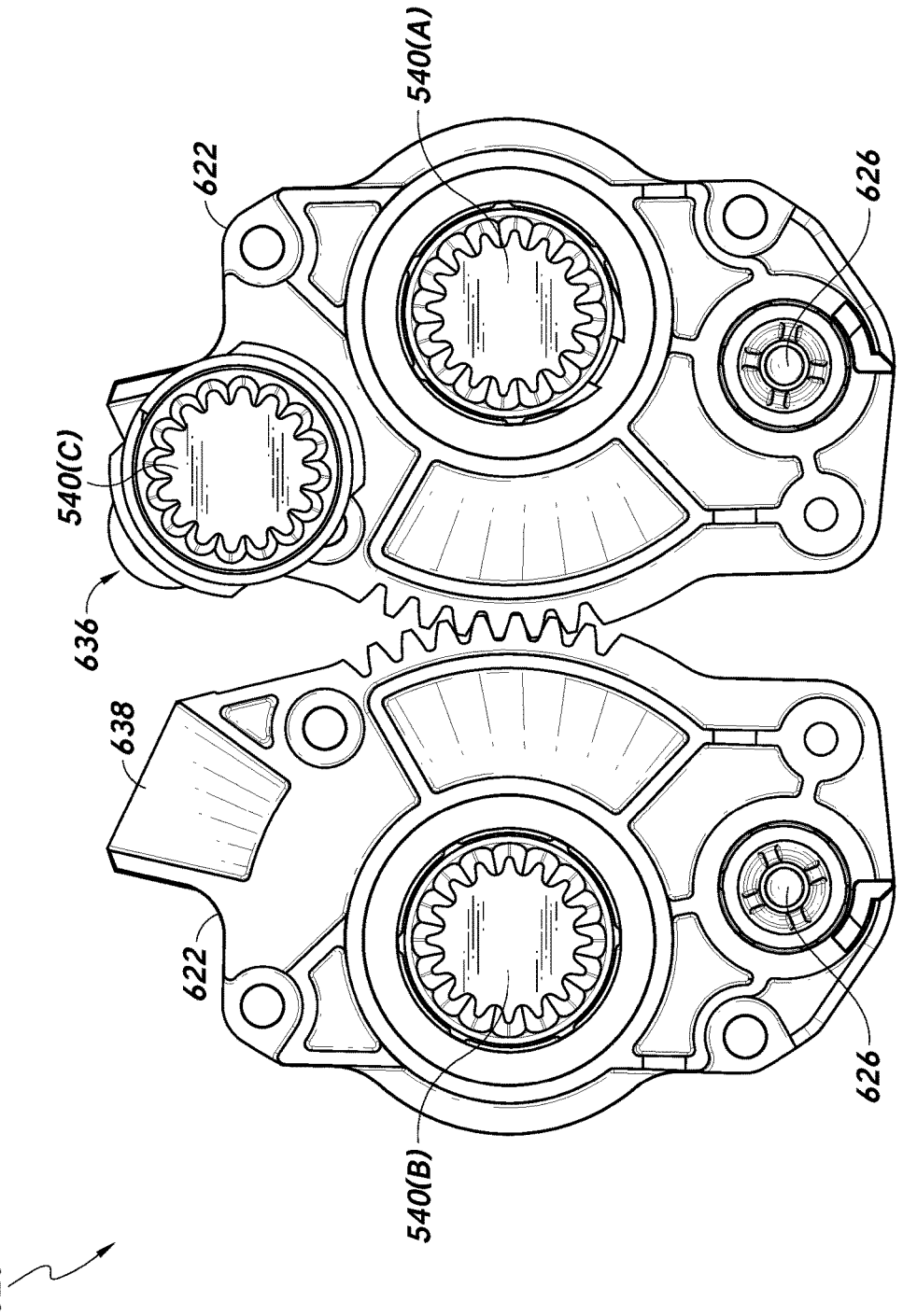
FIG. 6G illustrates a bottom view of the roller assembly in accordance with one or more embodiments.

In the illustrated example, the carrier plates 622 can be configured to rotate about the drive input axes 628. Rotation of the carrier plates 622 about the drive input axes 628 can move the rollers 538 between various positions. As shown in FIG. 6G, the instrument feeder device 530 can include the drive input 540(C) (also referred to as "the open/close drive input 540(C)") that is configured to cause the rollers 538 to move between various positions. The open/close drive input 540(C) can be connected to an open/close drive shaft 632 shown in FIG. 6D. Rotation of the open/close drive input 540(C) can cause rotation of the open/close drive shaft 632. The open/close drive input 540(C) and the open/close drive shaft 632 can rotate about an open/close drive axis 634. The open/close drive shaft 632 can further be connected to an off-axis protrusion 636. Thus, as the open/close drive shaft 632 rotates, the off-axis protrusion 636 also rotates about the open/close drive axis 634. The off-axis protrusion 636, however, may not be symmetric about the open/close axis 634. Thus, the off-axis protrusion 636 can provide an eccentric member that can move in an arc about the open/close axis 634.

As shown in FIG. 6D, the carrier plates 622 can each include a pocket/cavity 638. In the illustrated embodiment, the off-axis protrusion 636 is positioned at least partially within the pocket 638 of one of the carrier plates 622. As the off-axis protrusion 636 rotates about the open/close axis 634, the off-axis protrusion 636 can contact the walls of the pocket 638, which can cause the carrier plate 622 to rotate about the drive input axis 628. The off-axis protrusion 636 can also be rotated to a position in which it does not contact the walls of the pocket 638. In this position, with the off-axis protrusion 636 not contacting the pocket 638, a force applied by the rollers 538 on a shaft of a medical instrument can be determined wholly by the springs 612, which can be tuned to provide a desired force. In this position, the carrier plate 622 can be biased by the springs 612 to rotate to a position in which the rollers 538 are in a particular position (e.g., closed position). Rotating the off-axis protrusion 636 such that it contacts and presses against the sidewalls of the pocket 638 can cause the carrier plate 622 to rotate, overcoming the spring force of the springs 612. In some examples, the off-axis protrusion 636 comprises a roller configured to rotate about an axis that is not coaxial with the open/close drive axis 634. Such a roller may reduce friction between the off-axis protrusion 636 and the pocket 638.

In the example of FIG. 6D, the roller assembly 620 includes one open/close drive shaft 632 and one off-axis protrusion 636. In some instances, such as this example (and as seen in FIGS. 6E-6G), the two carrier plates 622 can be geared together, such that rotation of one carrier plate 622 causes an opposite and corresponding rotation of the other carrier plate 622. In this manner, rotation of both carrier plates 622 can be driven by a single open/close drive input 540(C). This can also allow the rollers 538 to be positioned symmetrically about the channel 534 of the instrument feeder device 530. In the illustrated example, although one off-axis protrusion 636 is included, both carrier plates 622 can include the pocket 638, and one of the pockets 638 can be empty. Inclusion of the empty pocket may facilitate manufacturing as the same or similar molds can be used for each carrier plate 622. Additionally, or alternatively, a second open close off-axis protrusion or other drive member can be used to independently rotate the other carrier plate, in which case the two carrier plates need not be geared together. Further, one of the carrier plates 622 may not include a pocket.

FIGS. 6E and 6F illustrate isometric and top views of the roller assembly 620 with the rollers 538 and a portion of the carrier plates 622 removed to illustrate the example gear assemblies 630 thereof. The gear assemblies 630 can transfer rotational motion between the drive inputs 540(A), 540(B) and the rollers 538. As shown, the gear assemblies 630 may comprise (for each carrier plate 622) a first gear 640 (e.g., a sun gear) and a second gear 642 (e.g., an orbital gear). In the illustrated example, each first gear 640 can be connected to the roller drive shaft 614/roller drive input 540(A), 540(B) such that rotation of the roller drive shaft 614/roller drive input 540(A), 540(B) causes rotation of the first gear 640. The first gear 640 can be mounted on the carrier plate 622 such that the first gear 640 can rotate with respect to the carrier plate 622. Each first gear 640 can rotate about a respective drive input axis 628 (shown in FIG. 6D).

Each first gear 640 can engage with the associated second gear 642 such that rotation of the first gear 640 causes rotation of the second gear 642. The second gear 642 can be mounted on the carrier plate 622 such that the second gear 642 can rotate with respect to the carrier plate 622. The second gear 642 can rotate about the respective roller axis 626 (shown in FIG. 6D). The second gear 642 can also be attached (or otherwise engaged with) the roller 538 such that rotation of the second gear 642 causes rotation of the roller 538. Thus, rotation of the roller drive inputs 540(A), 540(B) can cause rotation of the roller 538 through transmission by the first gear 640 and the second gear 642.

As described above, the carrier plates 622 can rotate about the drive input axes 628 to move the rollers 538 between various positions (e.g., closed and open positions). In the illustrated example, the second gear 642 is mounted on the carrier plate 622 at a location distanced from the drive input axis 628, and thus, rotates (with the carrier plate 622) about the drive input axis 628. As the second/orbital gear 642 rotates with the carrier plate 622 about the drive input axis 628 it also rotates about the first/sun gear 640.

This arrangement of the second/orbital gear 642 rotating about the first/sun gear 640 may be seen in the top view of FIG. 6F. As shown, the off-axis protrusion 636 can be rotated such that it contacts the pocket 638 of the carrier plate 622 to drive rotation of the carrier plate 622 in the direction indicated by the arrows in FIG. 6F. In particular, relative to the orientation shown in the figure, the bottom of the carrier plate 622 can be rotated inward, toward the center of the page, and the top of the carrier plate 622 can be rotated outward, towards the outer edge of the page. Gearing 644 between the plates 622 can cause a corresponding and opposite rotation of one carrier plate 622 as the other plate 622 moves/rotates. Each of the carrier plates 622 can rotate about the corresponding drive input axis 628. As the carrier plates 622 are rotated, the second/orbital gears 642 are driven outward, rotating about the sun gear 640. This arrangement can allow the rollers 538 (not shown in FIG. 6F, but connected to the second/orbital gears 642) to be driven regardless of the rotational position of the carrier plates 622. This can accommodate, for example, shafts of instruments that have different diameters.

FIG. 6G illustrates a bottom view of the roller assembly 620 illustrating the relationship of the roller drive inputs 540(A), 540(B) and open/close drive input 540(C) of the roller assembly 620, according to examples.

FIGS. 6D-6G illustrate one example actuator/roller assembly 620 that can be implemented within the instrument feeder device 530. Although various features are shown with a particular arrangement, the features can be implemented in other manners and/or other features can be implemented to facilitate movement of the rollers 538.

Example features of an instrument feeder assembly are discussed in application Ser. No. 16/994,504, filed Aug. 14, 2020 and entitled "Axial Motion Drive Devices, System, and Methods for a Robotic Medical System," the entire contents of which are incorporated herein by reference.

FIG. 7 illustrates an exploded view of an example instrument device manipulator assembly 702 associated with a robotic arm 112 in accordance with one or more embodiments. The instrument device manipulator assembly 702 includes an end effector 704 associated with a distal end of the robotic arm 112. The instrument manipulator assembly 702 further includes the instrument feeder 530/instrument feeder assembly 504. The instrument feeder 530/instrument feeder assembly 504 can incorporate electro-mechanical means for actuating an instrument 706, such as the scope 502 or other shaft-type instrument. In examples, the instrument manipulator assembly 702 can also include an adapter 708 configured to provide a driver interface between the end effector 704 and the instrument feeder 530/instrument feeder assembly 504. Description herein of upward-facing and downward-facing surfaces, plates, faces, components, and/or other features or structures may be understood with reference to the particular orientation of the instrument device manipulator assembly 702 shown in FIG. 7. That is, although the end effector 704 may generally be configurable to face and/or be oriented in a range of directions and orientations, for convenience, description of such components herein may be in the context of the generally vertical facing orientation of the end effector 704.

As shown, the end effector 704 of the robotic arm 112 can include various components/elements configured to connect to and/or align with components of the adapter 708, instrument feeder assembly 504, access sheath assembly 560, and/or instrument 706. For example, the end effector 704 can include drive outputs 710 (e.g., drive splines, gears, or rotatable disks with engagement features) to control/actuate a medical instrument, a reader 712 to read data from a medical instrument (e.g., radio-frequency identification (RFID) reader to read a serial number from a medical instrument), one or more fasteners 714 to attach to the instrument feeder 530/instrument feeder assembly 504 and/or adapter 708, markers 716 to align with an instrument that is manually attached to a patient (e.g., access sheath 564) and/or to define a front surface of the device manipulator assembly 702. In some embodiments, the end effector 704 and/or the robotic arm 112 includes a button 718 to enable an admittance control mode, wherein the robotic arm 112 can be manually moved.

In this example, the instrument device manipulator assembly 702 includes the adapter component 708 configured to provide a driver interface between the end effector 704 and the instrument feeder 530/instrument feeder assembly 504. The adapter 708 and/or the instrument feeder 530 may be removable or detachable from the robotic arm 112 and may be devoid of any electro-mechanical components, such as motors, in some embodiments. This dichotomy may be driven by the need to sterilize medical instruments used in medical procedures and the inability to adequately sterilize expensive capital equipment due to their intricate mechanical assemblies and sensitive electronics. Accordingly, the instrument feeder 530/instrument feeder assembly 504 and/or adapter 708 may be designed to be detached, removed, and interchanged from the end effector 704 (and thus the system) for individual sterilization or disposal. For example, the instrument feeder assembly 504 can be removed and replaced with a different type of instrument. Alternatively, the end effector 704 need not be changed or sterilized in some cases and may be draped (e.g., using drape 711) for protection. The adapter 708 can include connectors to transfer pneumatic pressure, electrical power, electrical signals, and/or optical signals from the robotic arm 112 and/or end effector 704 to the instrument feeder 530/instrument feeder assembly 504. In examples, the adapter 708 includes a coupler(s)/drive feature(s) 720 configured to couple the drive output 710 of the end effector 704 to the drive input 540 of the instrument feeder assembly 504. Further, in some instances, the adapter 708 can include a fastener(s) 722 configured to couple the adapter 708 to the end effector 704.

In some configurations, the sterile drape 711, such as a plastic sheet or the like, may be disposed between the end effector 704 and the adapter 708 to provide a sterile barrier between the robot arm 112 and the instrument feeder assembly 504. For example, the drape 711 may be coupled to the adapter 708 in such a way as to allow for translation of mechanical torque from the end effector 704 to the adapter 708. The adapter 708 may generally be configured to maintain a seal around the actuating components thereof, such that the adapter 708 provides a sterile barrier itself. The use of the drape 711 coupled to the adapter 708 and/or more other component(s) of the device manipulator assembly 702 may provide a sterile barrier between the robotic arm 112 and the surgical field, thereby allowing for the use of the robotic cart associated with the arm 112 in the sterile surgical field. The end effector 704 may be configured to be coupled to various types of sterile adapters that may be loaded onto and/or removed from the end effector 704 of the robotic arm 112. With the arm 112 draped in plastic, the physician and/or other technician(s) may interact with the arm 112 and/or other components of the robotic cart (e.g., screen) during a procedure. Draping may further protect against equipment biohazard contamination and/or minimize clean-up after procedure.

In this example, the instrument feeder 530 includes a plurality of drive inputs 540. In the illustrated embodiment, the instrument feeder 530 includes three drive inputs 540, although other numbers of drive inputs can be included. The drive inputs 540 can be in fixed positions spaced apart along a lower mating surface 724 of the instrument feeder 530, which facilitates coupling the drive inputs 540 to corresponding drive outputs (e.g., on the sterile adapter 708 and/or the end effector 704). The drive inputs 540 may be in fixed positions spaced apart along a corresponding mating surface designed for modular use and attachment to a variety of other instruments. Although various examples discuss the drive inputs 540 implemented at fixed positions, in some cases the drive inputs 540 can move within the lower surface 724. For example, the drive inputs 540(A) and 540(B) can be repositioned within the lower surface 724 to cause opposing rollers 538 to engage and/or disengage from each other and/or an instrument shaft.

A mechanical assembly within the instrument feeder 530 can allow the drive inputs 540 to be used to drive rotation of the actuator(s) 538 (e.g., drive rotation of opposing rollers) for axial motion of an instrument shaft and/or used to facilitate changes in an engagement state of the engagement assembly 532 with the instrument shaft. For example, the drive inputs 540(A) and 540(B) can receive input to control the actuator(s) 538 to axially drive a shaft disposed in the channel 534. The drive inputs 540(A) and/or 540(B) can receive torque/force applied by a drive output, which causes feed rollers or other actuators to axially drive a shaft-like instrument. Further, the drive input 540(C) (also referred to as "the open/close drive input") can receive input from a drive output to control the engagement assembly 532 to engage/disengage with an instrument shaft, open/close the channel 534 (e.g., using the retention feature(s) 536), or implement another state, as discussed in further detail below. The various states of the engagement assembly 532 can facilitate loading or unloading of an instrument shaft, engagement with the instrument shaft, driving of the instrument shaft, or other functions. In the illustrated example, the three drive inputs 540 are shown; however, any number of drive inputs can be implemented. Each of the drive inputs 540 can be configured to engage with a corresponding drive output on the robotic arm 112 and/or the sterile adapter 708. For example, each drive input 540 can comprise a receptacle configured to mate with a drive output that is configured as a spline. The drive inputs and drive outputs can be configured to engage to transfer motion therebetween. Thus, a drive output can be rotated to cause corresponding rotation of a drive input 540 to control various functionality of the instrument feeder 530.

References herein to an "instrument device manipulator assembly," "instrument manipulator assembly," "manipulator," "manipulator assembly," as well as other variations thereof, can refer to any subset of the components of the assembly 702 shown in FIG. 702, including a robotic arm, an end effector of a robot arm, an adapter configured to be coupled to a robotic end effector, an instrument feeder configured to be coupled to an end effector and/or adapter, an actuator of an instrument feeder (e.g., feed roller(s), shaft channel, retention feature, and/or other component(s)), and/or means/mechanism associated with an instrument feeder. Furthermore, it should be understood that references herein to an "actuator" can refer to any component of the assembly 702 that affects or causes, either directly or indirectly, movement of an instrument engaged with, coupled to, or otherwise actuatable by, an instrument feeder. For example, in accordance with embodiments disclosed here, an "actuator" may comprise any set or subset of the following devices or components: feed roller(s), shaft-actuating wheel(s)/roller(s), feed roller channel(s), instrument feeder drive input(s), adapter drive output(s), adapter drive input(s), and/or end effector drive output(s).

FIGS. 8 through 11 illustrate example states/positions of the engagement assembly 532 of the instrument feeder device 530 in accordance with one or more embodiments. In general, a drive output can engage with the one or more drive inputs 540 (not shown) of the instrument feeder device 530 to actuate one or more components of the engagement assembly 532, causing the engagement assembly 532/instrument feeder device 530 to enter a state/position. In this example, the engagement assembly 532 is implemented with opposing feed rollers 538, a channel 534 and/or a cover 536. However, the feed rollers 538 can be implemented as other types of actuators and/or the cover 536 can be implemented as another type of retention feature. Further, one or more of the illustrated components of the engagement assembly 532 can be eliminated and/or implemented in other manners. For example, the cover 536 may not be implemented in some instances.

Figures 1, 2, 8:
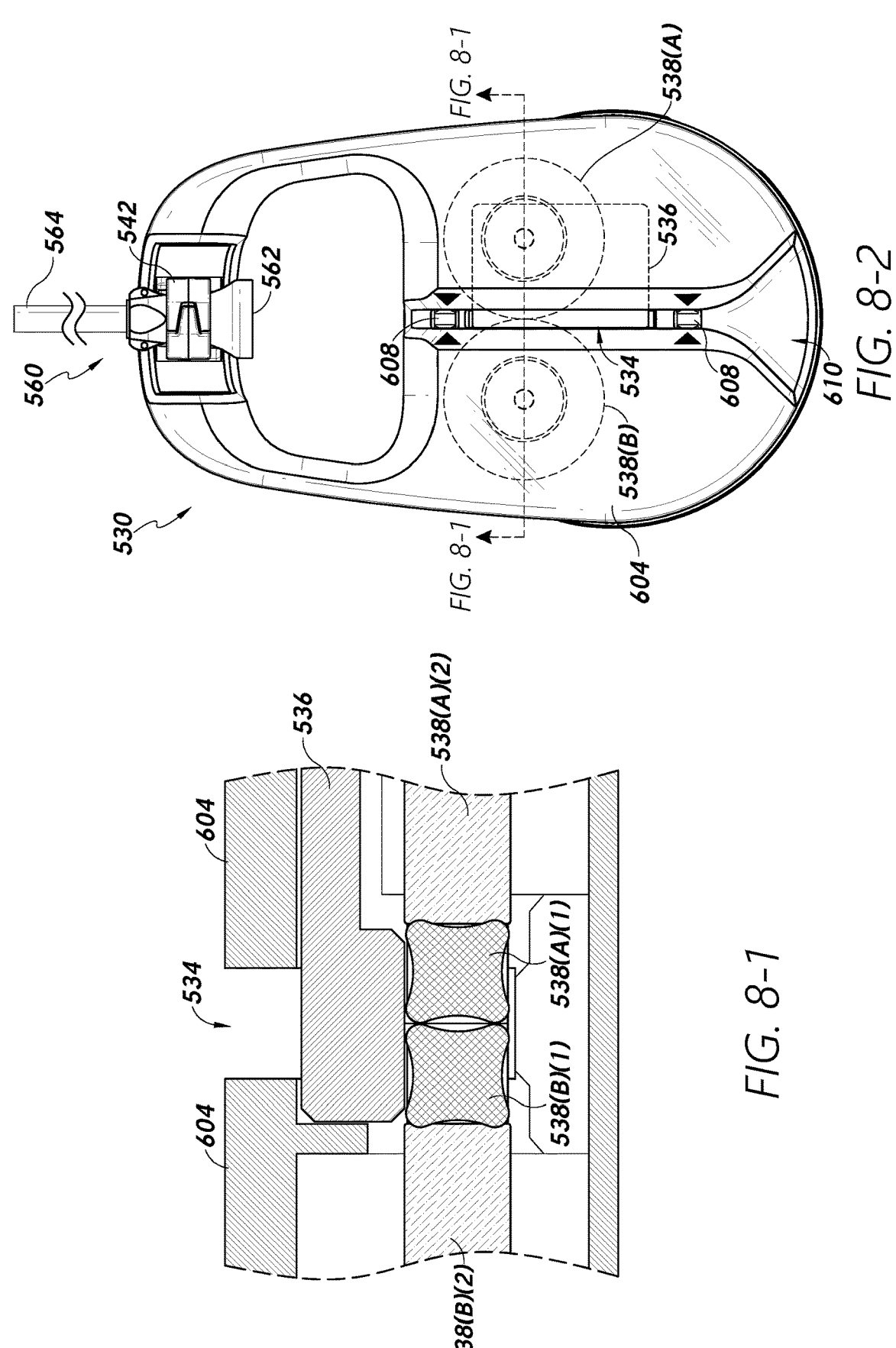

FIGS. 8-1 and 8-2 illustrate a state in which the rollers 538 are engaged and the cover 536 is closed. In examples, the rollers 538 can apply some amount of force to each other and/or hard-stop features (not illustrated) when in the engaged, which may be due to a biasing force of the one or more springs 612 (not illustrated), a force applied by a drive output, and/or another force applied to actuate the rollers 538 towards each other. In examples, the rollers 538 may be contacting each other. However, the rollers 538 may not contact each other, but may be within a threshold distance of each other (which may be facilitated by hard-stop features).

In this example, the cover 536 is closed to prevent objects from entering/leaving the channel 534. As noted above, in some instances, the cover 536 can be coupled to one or more of the rollers 538 such that movement of the rollers 538 causes the cover 536 to open or close. However, the cover 536 can be independently actuated. The cover 536 can have a variety of shapes and/or sizes. In this example, the cover 536 includes dimensions to substantially close/cover the channel 534 when positioned over the channel 534.

In some instances, outer edge portions 538(A)(1)/538(B)(1) of the rollers 538(A)/538(B) can be formed of a different material than inner portions 538(A)(2)/538(B)(2) of the rollers 538. For example, the outer/circumferential portions 538(A)(1)/538(B)(1) can include a deformable material that is configured to grip/contact an instrument shaft to axially drive the elongate shaft and/or avoid damage to the elongate shaft. However, the outer edge portions 538(A)(1)/538(B)(1) and the inner portions 538(A)(2)/538(B)(2) can be formed of the same material.

Figures 1, 2, 9:
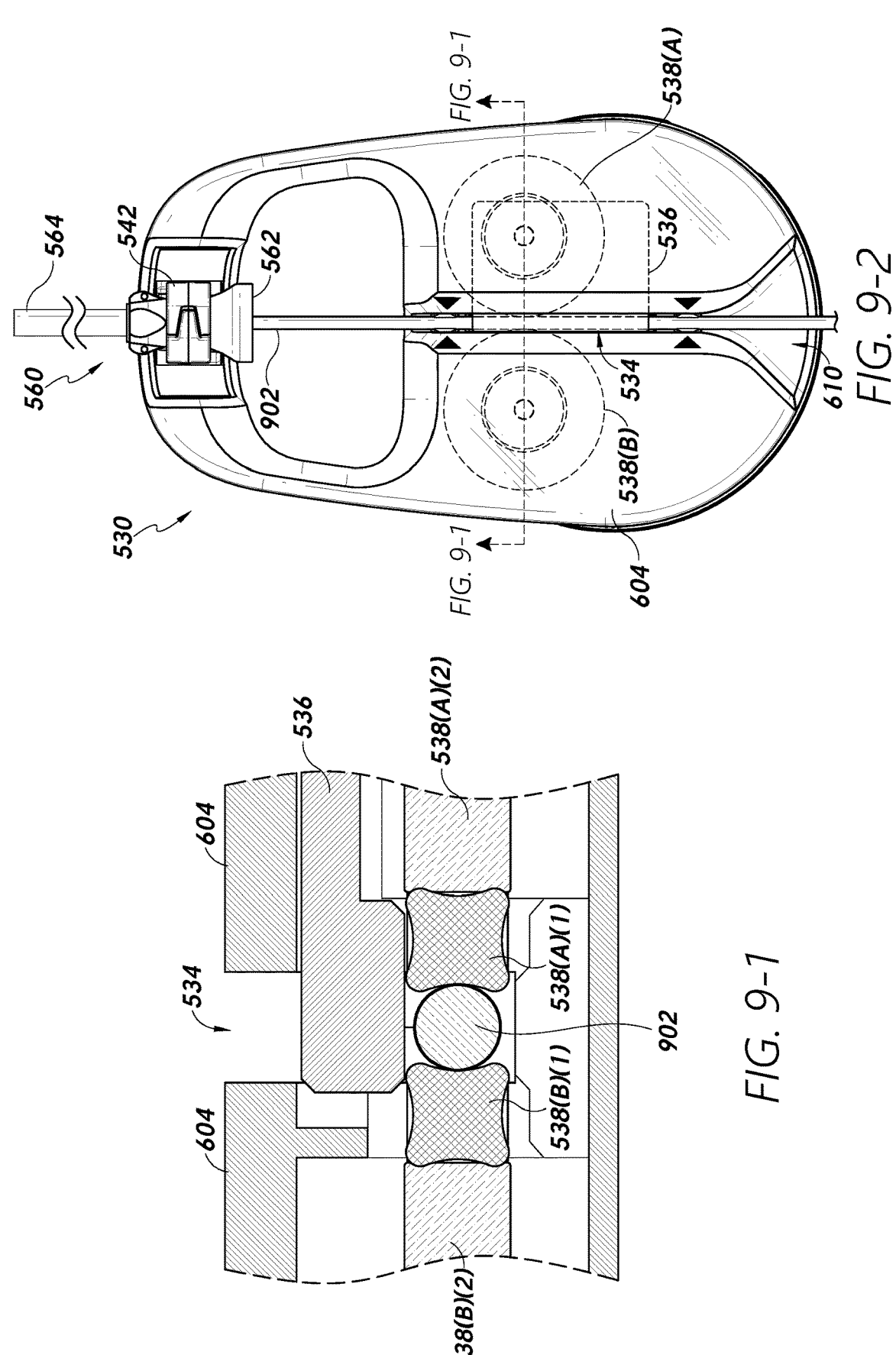

FIGS. 9-1 and 9-2 illustrate a state in which the rollers 538 are engaged with an instrument shaft 902 and the cover 536 is closed. As shown, the rollers 538 can be engaged with or otherwise contact opposite or opposing sides of the elongate shaft 902, which is positioned between the rollers 538 within the channel 534. As illustrated, the elongate shaft 902 is loaded into the channel 534 and inserted into the access sheath assembly 560. The rollers 538 are pressed into or otherwise engaged with the elongate shaft 902. In examples, the rollers 538 can apply some amount of force to engage with the elongate shaft 902, which may be due to a biasing force of the one or more springs 612 (not illustrated), a force applied by a drive output, and/or another force applied to actuate the rollers 538 towards each other.

In this position/state, the rollers 538 can rotate to drive axial motion of the instrument shaft 902 (e.g., insert/retract the shaft 902). For example, rotating the rollers 538 in a first direction can cause insertion of the shaft 902 (e.g., in a distal direction towards the patient), and rotating the rollers 538 in a second opposite direction can cause retraction of the shaft 902 (e.g., in a proximal direction away from the patient). Here, the direction of the rollers 538 can refer to a direction of motion of a portion of the rollers 538. For instance, rotation in the first direction for insertion of the shaft 902 can refer to rotation of the engagement portion of the rollers 538 in a distal direction, and rotation for retraction can refer to rotation of the engagement portion of the rollers 538 in a proximal direction. With respect to the view of the rollers 538 in FIG. 9-2, the left roller 538(B) can rotate counterclockwise while the right roller 538(A) rotates clockwise to rotate the rollers 538 in the distal direction (e.g., to insert the shaft 902), and vice versa to rotate the rollers 538 in the proximal direction (e.g., to retract the shaft 902).

In this example, the cover 536 is at least partially closed to help retain the instrument shaft 902 in the channel 534, such as to prevent the rollers 538 from ejecting the shaft 902 upwards and/or latterly out of the channel 534. In other words, the cover 536 encloses at least a portion of the channel 534 where the instrument shaft 902 is located to prevent the shaft 902 from leaving the channel 534. However, as noted above, the cover 536 can be eliminated in some cases.

Figures 1, 2, 10:
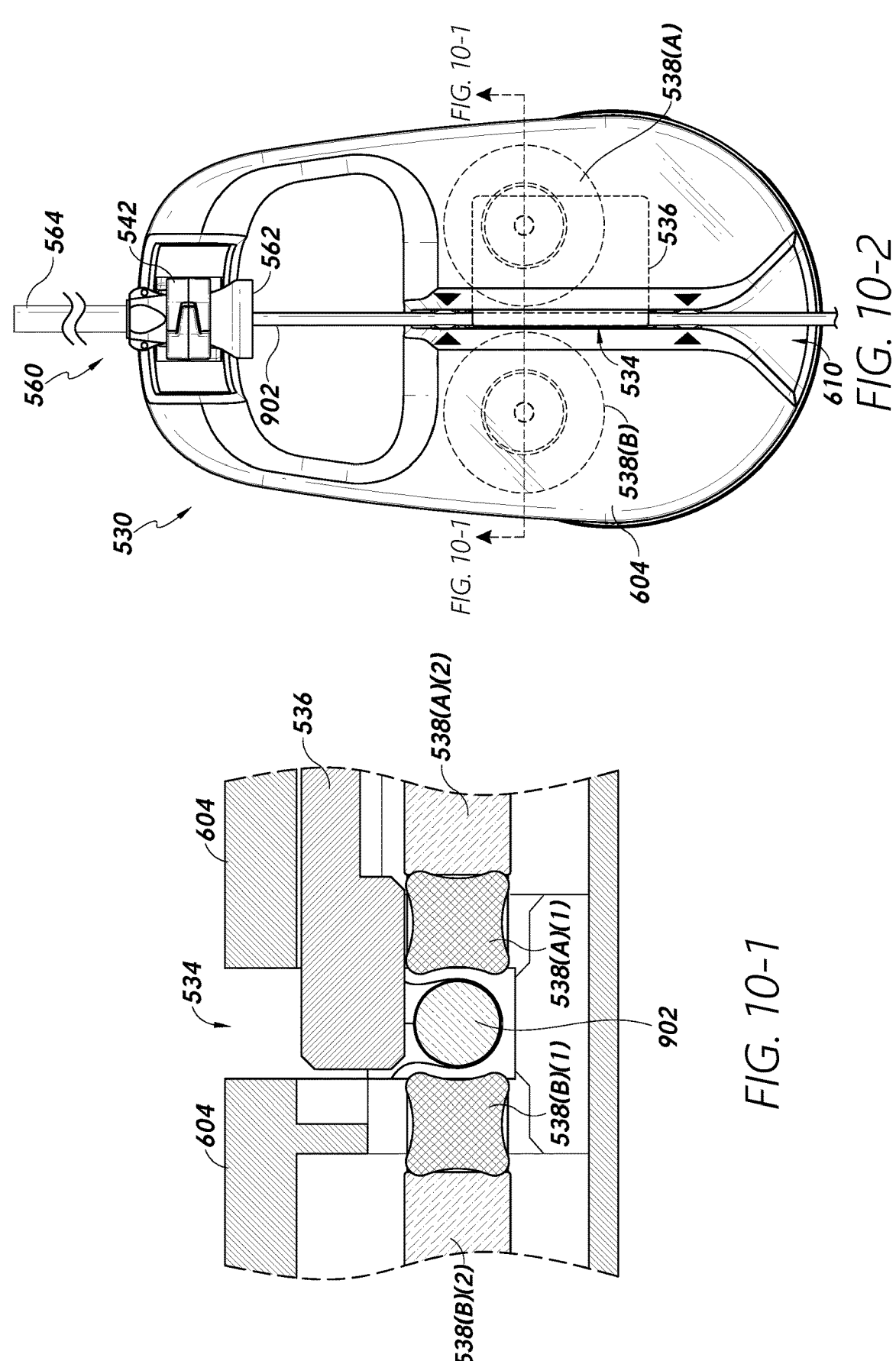

FIGS. 10-1 and 10-2 illustrate a state in which the rollers 538 are disengaged and the cover 536 is closed. Such state/position can be an intermediate state between a closed/engaged state and an open/loading state. As shown, the rollers 538 can be disengaged with the elongate shaft 902 or otherwise moved away from contacting the elongate shaft 902. Further, the cover 536 can be closed over at least a portion of the channel 534 such that the instrument shaft 902 is still retained within the channel 534. In this state/position, the rollers 538 can be disengaged from the instrument shaft 902, allowing the shaft 902 to slide or roll freely in the channel 534.

In examples, this position/state is used for various cases during a procedure when retention of an instrument shaft is desired, but more freedom of movement of the shaft relative to the instrument feeder device 530 is desired. For example, this state/position can be used to allow the instrument shaft 902 to roll about its longitudinal axis, allow a robotic arm coupled to the instrument feeder device 530 to be repositioned (while avoiding insertion/retraction of the shaft 902), allow a robotic arm coupled to a handle/instrument base of the shaft 902 to be repositioned (and allow the shaft 902 to freely slide within the channel 534), and/or allow other functions without engaging with the shaft 902. In some cases, a robotic arm can be moved while operating in an admittance/manual mode. However, a robotic arm can be controlled to move based on a control signal or other input.

In one illustration, a robotic arm that is coupled to the instrument feeder device 530 can be moved during a procedure (or at other times) to adjust a position/placement of an access sheath that is coupled to the robotic arm. The access sheath can be disposed at least partly into a patient and used to insert the medical instrument into the patient. To maintain within the instrument feeder device 530, the instrument feeder device 530 can implement this intermediate state to allow the elongate shaft 610 to move freely within the instrument feeder device 530 while the robotic arm that is coupled to the instrument feeder device is repositioned. In examples, the robotic arm is moved using an admittance control mode; however, the robotic arm can be moved in other manners.

Figures 1, 2, 11:
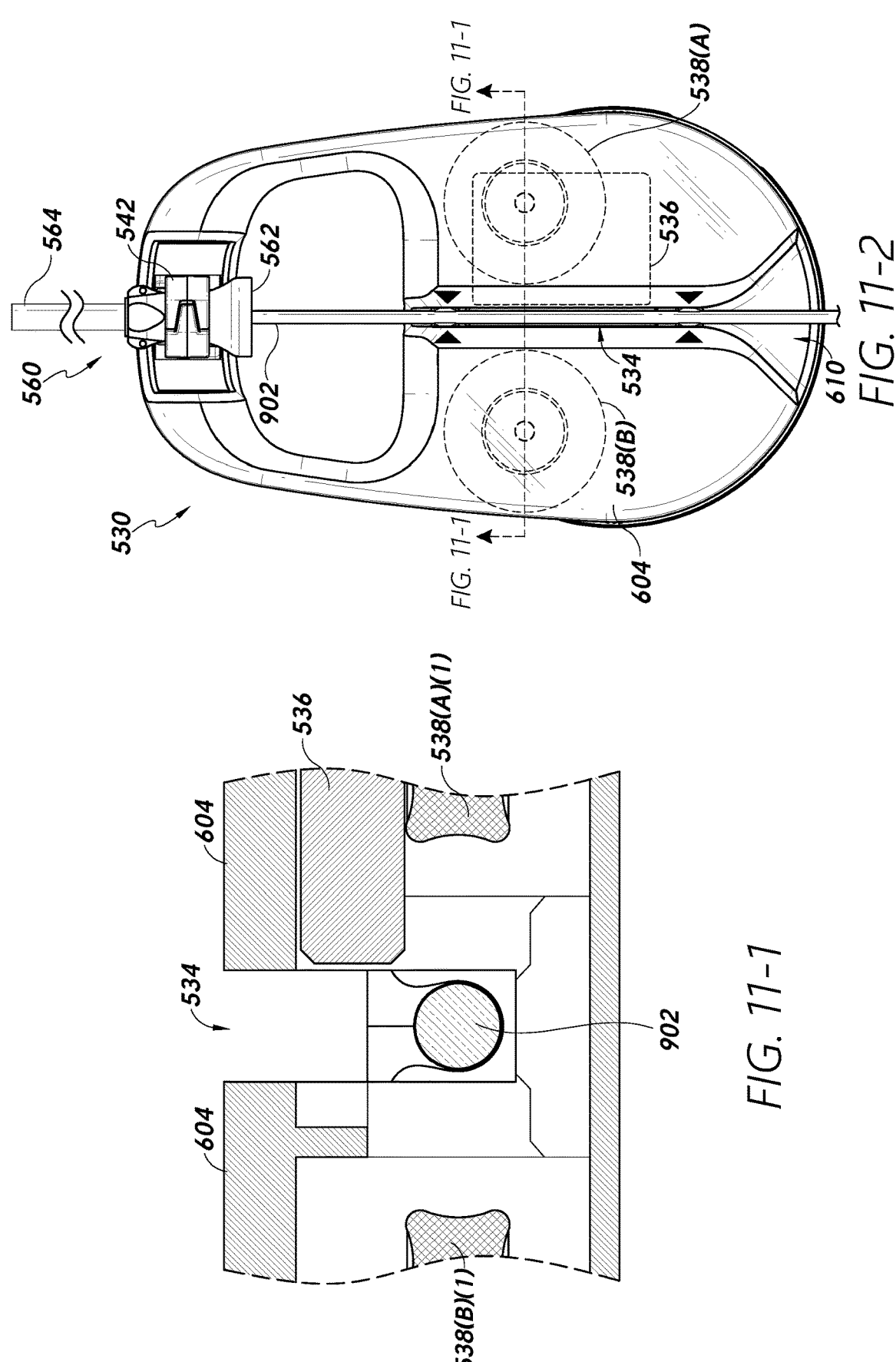

FIGS. 11-1 and 11-2 illustrate a state in which the rollers 538 are disengaged and the cover 536 is open. Such state/position can be referred to as a fully open/disengaged or loading state. As shown, the rollers 538 can be disengaged with the elongate shaft 902 or otherwise moved away from contacting the elongate shaft 902 and the cover 536 is fully open to allow access to the channel 534. Although the rollers 538 are illustrated as being positioned farther apart from each other than in the intermediate state of FIGS. 10-1 and 10-2, the rollers 538 can be positioned in the same position as FIGS. 10-1 and 10-2 and/or at another disengaged position. The cover 536 can be open or otherwise repositioned to provide access to the channel 534 (e.g., from above). In the example shown, the cover 536 is positioned completely under the upper housing 604. However, the cover 536 can be positioned at other locations that may be at least partially within the channel 534, but may otherwise allow the instrument shaft 902 to be loaded or unloaded from the channel 534.

In examples, the open/fully disengaged state can facilitate loading or unloading of the instrument shaft 902 into the instrument feeder device 530, which can simplify use of the device and/or decrease operating times. For example, an open channel can facilitate loading and/or unloading of the instrument shaft 902 before, during, or after a medical procedure. In one illustration, the fully open/disengaged state can allow a user to manually make adjustments to the shaft 902 and/or associated medical instrument, without having to fully retract the shaft 902 from within the patient.

Figure 12:
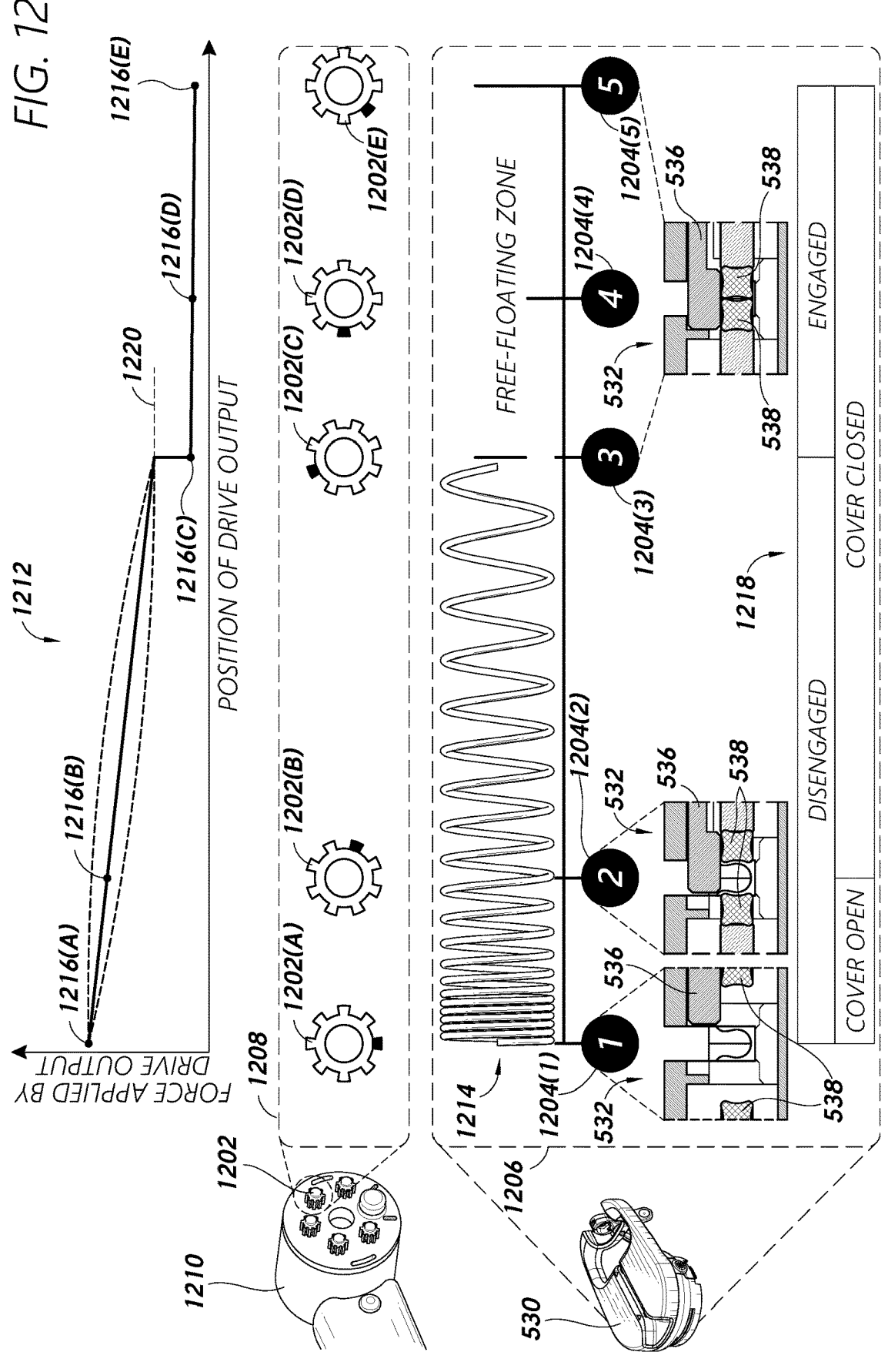
FIG. 12 illustrates example states of an engagement assembly when an instrument shaft is not disposed/loaded within the engagement assembly in accordance with one or more embodiments.
Figure 13:
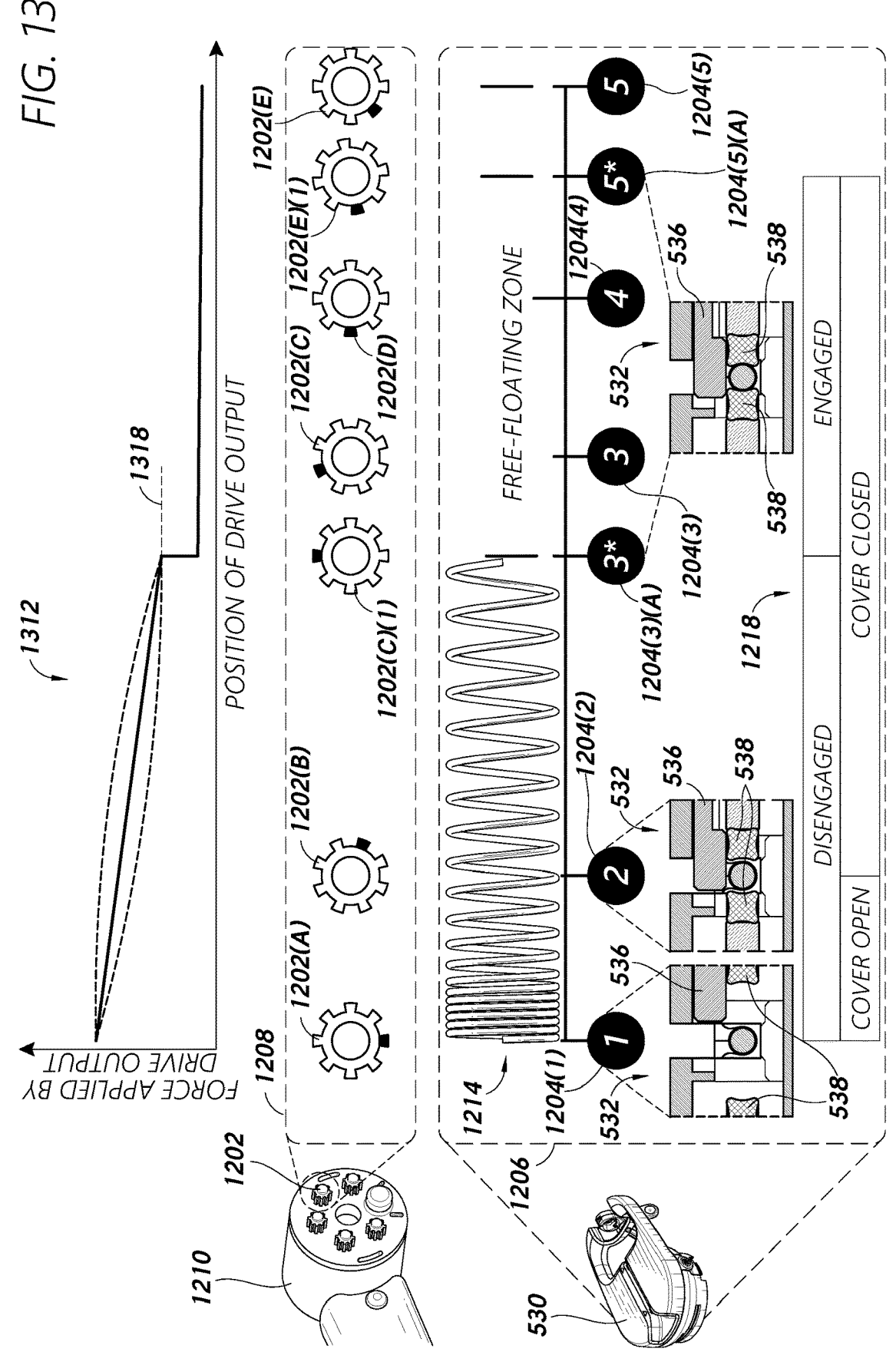
FIG. 13 illustrates example states of an engagement assembly when an instrument shaft is disposed/loaded within the engagement assembly in accordance with one or more embodiments.

FIGS. 12 and 13 illustrate example states of the engagement assembly 532 and various details regarding an example drive output 1202 for the states of the engagement assembly 532 in accordance with one or more embodiments. In particular, FIG. 12 illustrates states 1204 of the engagement assembly 532 (within a block 1206) without an instrument shaft disposed/loaded therein, while FIG. 13 illustrates states 1204 of the engagement assembly 532 with an instrument shaft disposed/loaded therein. These figures illustrate some of many example states of the engagement assembly 532 discussed herein. Although various states are illustrated, any number of states can be implemented, such as to transition between the states shown and/or to implement other states not explicitly shown.

In FIGS. 12 and 13, images within a block 1208 illustrate example positions (e.g., rotational angles) of a drive output 1202 associated with an end effector 1210 of a robotic arm. Here, the end effector 1210 is coupled to the instrument feeder device 530, which is shown as separated from the end effector 1210 for illustrative purposes. In these examples, the drive output 1202 rotates to implement the various states 1204 of the engagement assembly 532. For ease of illustration, the drive output 1202 is shown as a gear (which includes a marking to show the rotational position of the gear); however, the drive output 1202 can be implemented in other manners. The illustrated positions of the drive output 1202 indicate relative positions to each other and may not indicate an amount of actual rotation of the drive output 1202 to facilitate a particular state of the engagement assembly 532. For example, the drive output 1202 can be rotated any number of times to facilitate a particular position.

In some examples, the drive output 1202 is configured to apply different amounts of force to a drive input 540 of the engagement assembly 532 to facilitate the different states 1204. Graphs 1212 and 1312 in FIGS. 12 and 13, respectively, illustrate example forces that can be applied/experienced by the drive output 1202 relative to a position of the drive output 1202. The forces applied can be linear (e.g., solid lines) or non-linear (e.g., dotted lines). The lines in these graphs are provided for illustrated purposes and may not reflect actual force amounts applied by the drive output 1202. Although different forces are applied in this example to control a state of the engagement assembly 532, in other examples the engagement assembly 532 can be controlled in other manners.

In these examples, the engagement assembly 532 can generally be configured to bias towards an engaged/closed state. Such biasing can be facilitated through the one or more springs 612 (not shown) and/or other means/mechanisms, as discussed herein. A representation 1214 of the one or more springs 612 is provided within the block 1206 to indicate an amount of compression and/or force exerted by the one or more springs 612 and/or other components of the instrument feeder device 530. It should be understood that this representation 1214 is merely provided for illustrative purposes and should not be used to limit the features of the instrument feeder device 530 (including the one or more springs 612). In examples, the engagement assembly 532 can be positioned in an engaged state when the instrument feeder device 530 is not attached to a robotic arm, less than a threshold amount of force is applied to the drive input 540, etc. As such, the drive output 1202 can generally be configured to apply force (e.g., torque) to the drive input 540 to actuate the engagement assembly 532 towards an open/disengaged state.

Although some examples discuss the instrument feeder device 530 as configured to bias towards an engaged state, the instrument feeder device 530 can be implemented in other manners. For instance, the engagement assembly 532 can be configured to bias towards a disengaged/open state by using a spring in a different configuration and/or implementing other features. Further, in some instances, the engagement assembly 532 may not be configured to bias towards any state. Here, the engagement assembly 532 may be configured to remain in any state, even when the instrument feeder device 530 is decoupled from robotic arm.

FIG. 12 illustrates example states 1204 of the engagement assembly 532 when an instrument shaft is not disposed/ loaded within the engagement assembly 532. As shown at 1218, the states from 1204(1) up to 1204(3) are generally associated with a disengaged state in which the rollers 538 are disengaged, while the states 1204(3)-1204(5) are generally associated with an engaged state in which the rollers 538 are engaged. An engaged state can refer to the rollers 538 contacting each other, disposed at hard-stop positions (which can be facilitated by hard-stop features on the instrument feeder device 530 that keep the rollers 538 from contacting each other), disposed within a predetermined distance to each other, disposed within a predetermined distance to an axis/region, etc. In contrast, a disengaged state can refer to the rollers 538 not contacting each other, not contacting an instrument shaft, not disposed at hard-stop positions, positioned more than a predetermined distance from each other, positioned more than a predetermined distance to an axis/region, etc. Further, the cover 538 can be implemented to facilitate an open or closed state. For example, the cover 538 can be in an open/partially open state from 1204(1) up to 1204(2) and a closed state from 1204 (2)-1204(5). The blocks 1218 are provided for illustrative purposes and the states of these elements can be different than that depicted. For example, the transitions between the different states (e.g., engaged to disengaged and/or cover open to cover closed) can occur at different points other than those depicted.

In FIG. 12, the states 1204(1)-1204(5) are associated with rotational positions 1202(A)-1202(E) and applied forces 1216(A)-1216(E), respectively. For example, the state 1204 (2) can be implemented when the drive output 1202 is positioned at a rotational position 1202(B) and/or applies an amount of force 1216(B). In some instances, the positions 1202(A) and/or 1202(E) are associated with hard-stop positions that are facilitated by hard-stop features on the instrument feeder device 530. A hard-stop position can be detected based on a change in force applied by the drive output 1202 (e.g., a spike in force applied). In some cases, the positions 1202(A) and/or 1202(E) are used as reference positions.

The example states 1204 are shown with a free-floating zone in which the engagement assembly 532 remains in an engaged state for various rotational positions of the drive output 1202 (e.g., the positions 1202(C)-1202(E)). This can be implemented to provide some amount of play/backlash between the components of the instrument feeder device 530, which can be facilitated by hard-stop features and/or other features in the instrument feeder device 530. However, in other examples, the free-floating zone is not implemented and/or fewer engaged states are implemented.

In the example of FIG. 12, to transition the engagement assembly 532 from an engaged state to a disengaged state, the drive output 1202 can rotate and/or apply a particular amount of force. For instance, as the drive output 1202 rotates from position 1202(D) in a clockwise manner and reaches the rotational position 1202(C), the one or more springs 612 of the instrument feeder device 530 can begin to exert a force back on the drive output 1202, such that more than a threshold amount of force 1220 is required (as shown in the graph 1212) to cause the engagement assembly 532 to transition to a disengaged state. This change in force at position 1202(C) can be detected (e.g., as a force spike). In some cases, the position 1202(C) is used as a reference position. In this example where an instrument shaft is not loaded, the state 1204(3) is generally associated with a transition from an engaged state to a disengaged state.

As shown in FIG. 12, the drive output 1202 can continue to rotate in a clockwise manner and/or apply additional force to cause the engagement assembly 532 to reach the state 1204(2). For example, as the drive output 1202 rotates in a clockwise manner, the distance between the rollers 538 increases and/or the cover 536 begins to move/open. The one or more springs 610 can compress to require the drive output 1202 to increase an amount of force (e.g., torque) applied to reach the state 1204(2). At the state 1204(2), the rollers 538 are disengaged (e.g., separated a particular distance from each other) and the cover 536 remains closed over the channel 534, even though the cover 536 may have begun to open. The state 1204(2) can be referred to as an intermediate state between a closed/engaged state and a fully open/loading state. Further, the drive output 1202 can continue to rotate in a clockwise manner to reach the state 1204(1), wherein the rollers 538 are disengaged (e.g., separated even more from each other) and the cover 536 is fully open.

Although in this example an increasing amount of force (e.g., torque) is needed to transition the engagement assembly 532 from the state 1204(3) to the state 1204(1) (as shown in the graph 1212), such transition can be implemented in other manners, such as by applying a decreasing amount of force, a constant amount of force and just changing a rotational position of the drive output 1202, etc. Further, although this example discusses rotation in a clockwise manner to transition from an engaged state to a disengaged state, the drive output 1202 can rotate in a counterclockwise or another manner.

FIG. 13 illustrates example states 1204 of the engagement assembly 532 when an instrument shaft is disposed/loaded within the engagement assembly 532. Here, the engagement assembly 532 can transition between at least some of the states 1204 at different rotational positions of the drive output 1202. In particular, since an instrument shaft is loaded into the engagement assembly 532, the point where the one or more springs 612 begin to exert force on the drive output 1202 is moved (e.g., to the left in this figure). As shown, the engagement assembly 532 now transitions from an engaged state to a disengaged state when the drive output 1202 is rotated to position 1202(C)(1). The engagement assembly 532 can begin to transition from the engaged state 1204(3)(A) when the drive output 1202 applies more than a threshold amount of force 1318, as shown in the graph 1312. Further, in this example, the free-floating zone has shifted such that the end of the zone is associated with a rotational position 1202(E)(1) for the drive output 1202 and an engaged state 1204(5)(A). This can occur due to a rotational displacement or shift of the components of the engagement assembly 532 that facilitate hard-stop positions, in some cases. For example, the rotational position 1202(E)(1) can be associated a hard-stop feature of the instrument feeder device 530. However, in other examples, the free-floating zone can extend farther to enable the drive output 1202 to reach the previous rotational position 1202(E). Further, the free-floating zone can extend to include other rotational positions for the drive output 1202 and/or be implemented in other manners.

Although various examples are discussed in the context of determining a state of an instrument feeder device based on a force applied by a drive output and/or a position of the drive output, the state of the instrument feeder device can additionally, or alternatively, be determined in based on other information. For example, the instrument feeder device can include one or more sensors for/on a roller, cover, channel, and/or other component that are configured to detect a proximity, pressure, and/or another characteristic. In one illustration, a sensor can be implemented on rollers and/or another component around the rollers to determine a proximity of the rollers to each other and/or an instrument shaft. Further, a drive input of an instrument feeder device can include a sensor/feature to a detect rotational position of the drive input, which can be used to determine a state of the instrument feeder device. Moreover, a sensor can be implemented on a cover to detect when the cover is open, partially open, or closed. Additionally, or alternatively, an elongate shaft of a medical instrument can include a sensor configured to detect pressure/proximity, such as pressure applied by rollers of an engagement assembly. In some cases, the instrument feeder device may not implement a spring(s) to bias the rollers to a particular state (e.g., clamp down on an instrument shaft). Here, the state of the instrument feeder device can be based on a position of a drive output and/or a force applied by the drive output (which can include detecting a fully engaged state based on a spike in force due to contact with an instrument shaft). In some cases where a spring(s) is not implemented, the drive output can apply some amount of force to fully engage/clamp the instrument shaft.

In some examples, an instrument feeder device can be implemented with a first drive input configured to control an engagement of rollers (e.g., a distance between the rollers) and a second drive input configured to control actuation of a cover (e.g., to open or close the cover). As such, separate drive outputs can be implemented to control different states of the engagement assembly, wherein a state of the rollers can be independently controlled from a state of the cover. Further, in some examples, a state of a first component (e.g., rollers or cover) can be controlled manually and detected by a sensor(s), wherein such detected state can cause a second component (e.g., cover or rollers) to be controlled to facilitate a particular state for the engagement assembly.

FIGS. 14-18 illustrate example flow diagrams of process 1400, 1500, 1600, 1700, and 1800 respectively, for performing various techniques discussed herein. The various operations/acts associated with the processes 1400, 1500, 1600, 1700, and 1800 can be performed by control circuitry implemented in any of the devices/systems discussed herein or a combination thereof, such as the control system 150, the robotic system 110, the table 170, a medical instrument, an instrument feeder device, and/or another device. Although various blocks are illustrated as being part of the processes 1400, 1500, 1600, 1700, and/or 1800, any of such blocks can be eliminated. Further, additional blocks can be implemented as part of the processes 1400, 1500, 1600, 1700, and/or 1800. The order in which the blocks are illustrated is provided merely for illustrative purposes, and the blocks can be implemented in any order. In some embodiments, one or more of the blocks of the processes 1400, 1500, 1600, 1700, and/or 1800 are implemented as executable instructions, that when executed by control circuitry, cause the control circuitry to perform the functionality/operations discussed. However, one or more of the blocks of the processes 1400, 1500, 1600, 1700, and/or 1800 can be implemented in other manners, such as by other devices/systems, a user(s), etc.

FIG. 14 illustrates the example process 1400 to determine a state of an engagement assembly of an instrument feeder device in accordance with one or more embodiments.

At block 1402, the process 1400 can include detecting one or more events. For example, control circuitry can detect one or more events associated with an instrument feeder device, medical instrument, robotic system, and/or another device/component of a medical system configured to perform a medical procedure. To illustrate, the control circuitry can detect a coupling of the instrument feeder device to a robotic arm of the robotic system (e.g., based on sensor data from the robotic arm/instrument feeder device), a coupling/decoupling of an instrument base of a medical instrument to a robotic arm (e.g., based on sensor data from the robotic arm/medical instrument base), the passage of a predetermined period of time coupling of an instrument base to a robotic arm, a request/instruction to a roll an elongate shaft (e.g., based on user input, a system determination, etc.), a request/instruction to enable/disable manual movement of a robotic arm (e.g., an admittance control mode is enabled), etc.

As discussed herein, a medical system can include a robotic system having one or more robotic arms configured to couple to a medical instrument, instrument feeder device, and/or another device/component. For example, the robotic system can include a first robotic arm having an end effector configured to couple to an instrument feeder device (that can engage with an elongate shaft of a medical instrument) and a second robotic arm configured to couple to an instrument base of the medical instrument. The first robotic arm can include one or more drive outputs configured to couple to and/or actuate one or more drive inputs of the instrument feeder device. For example, a first drive output can be configured to actuate a first drive input of the instrument feeder device to control engagement of the instrument feeder with the elongate shaft of the medical instrument, while a second drive output can be configured to actuate a second drive input of the instrument feeder device to axially move the elongate shaft.

Further, an instrument feeder device can include an engagement assembly configured to receive and/or engage with an elongate shaft of a medical instrument. The engagement assembly can include an actuator configured to axially move the elongate shaft, a channel configured to receive the elongate shaft, and/or a retention feature configured to selectively open or close the channel. In some examples, the instrument feeder device is configured to bias the actuator to an engaged state or a disengaged state.

At block 1404, the process 1400 can include causing a first drive output to actuate an engagement assembly of an instrument feeder device. For example, control circuitry can cause a first drive output of a robotic arm to actuate, thereby causing actuation of a first drive input associated with an engagement assembly of an instrument feeder device. The first drive input can be configured to control an engagement state of the engagement assembly.

In some examples, the control circuitry causes the first drive output to actuate based on detecting one or more events at block 1402. This can intelligently/automatically control the engagement assembly, such as without user interaction with the engagement assembly. In some instances, the control circuitry can control the engagement assembly to actuate from an engaged state to a fully open/disengaged state upon detecting that the associated instrument feeder device is loaded onto/coupled to a robotic arm, such as during setup for a procedure. This can allow a user to load a shaft of a medical instrument into the engagement assembly.

Further, in some instances, the control circuitry can control the engagement assembly to actuate from a disengaged state (e.g., fully open state) towards/to an engaged state upon detecting that an instrument base of a medical instrument was coupled to a robotic arm and/or after a predetermined period of time has passed from detecting a coupling the instrument base to the robotic arm. For example, a user may first load the instrument shaft into the instrument feeder device coupled to a first robotic arm, and then, couple an instrument base to a second robotic arm. However, the user can couple/load the components of the medical instrument in any order. Here, by transitioning the instrument feeder device to an engaged state after detecting a coupling of the instrument base to the second robotic arm, the control circuitry can engage with the medical instrument to begin driving the medical instrument.

Moreover, in some instances, the control circuitry can control the engagement assembly to actuate from an engaged state to a disengaged/intermediate state upon determining to roll an elongate shaft of a medical instrument and/or determining to enable an admittance control mode for a robotic arm. For example, a user can provide input to roll the shaft or enable an admittance control mode for a robotic arm coupled to the instrument feeder device and/or a robotic arm coupled to the instrument base. The admittance control mode can be used to adjust a position of a robotic arm for various purposes. In response to a roll/admittance control detection, the control circuitry can cause the engagement assembly to transition from an engaged state to an intermediate state where a cover is substantially closed and rollers are disengaged from the shaft. This can allow the engagement assembly to retain the shaft without restricting the movement of the shaft. When the roll is completed and/or the admittance control mode is disabled, the control circuitry can cause the engagement assembly to return to the engaged state.

Furthermore, in some instances, the control circuitry can control the engagement assembly to actuate from an engaged state to a disengaged state upon determining a decoupling of an instrument base from a robotic arm. For instance, a user may decouple the instrument base from the robotic arm upon completion of a procedure and/or to facilitate manual driving of the medical instrument. Here, the control circuitry can detect that the instrument base is removed from the robotic arm and control the engagement assembly to actuate to a fully open state, wherein the shaft can be removed from the engagement assembly.

Although various illustrations are provided, the control circuitry can cause the first drive output to actuate in other scenarios, such as to transition the engagement assembly between any state, transition the engagement assembly towards a state without changing states, transition the engagement assembly to a hard-stop position (e.g., upon coupling the instrument feeder device to a robotic arm), etc. As such, the control circuitry can cause the first drive output to actuate for a variety of purposes.

In examples, the control circuitry can detect that an instrument/device is coupled to/decoupled from a robotic arm based on data from a sensor(s) of an end effector, instrument feeder device, medical instrument base, instrument shaft, etc. Such sensor(s) can include a proximity sensor(s), magnetic sensor(s), etc. For example, an instrument feeder device/instrument base can include a magnet, radio-frequency identification (RFID) tag, Quick Response/bar code, and/or another element, and an end effector of a robotic arm can include a sensor/device configured to detect such element, such as when the instrument feeder device/instrument base is placed in proximity to the end effector.

At block 1406, the process 1400 can include determining an amount of forced applied by the first drive output and/or a position of the first drive output. For example, control circuitry can determine an amount of force applied by the first drive output and/or a position of the first drive output based on readings/data from one or more sensors (e.g., force/torque sensors for the first drive output), one or more signals generated/sent to control the first drive output, etc. In some instances, the amount of force applied by the first drive output represents a net resultant force that accounts for an amount of force (e.g., torque) applied by a motor/mechanism that drives the first drive output and/or an amount of feedback force applied by the drive input of the instrument feeder device (e.g., which can be due to one or more springs that bias the engagement assembly). Further, in some instances, the position of the first drive output can include a rotational position of the first drive output, which can include/indicate any number of rotations/turns of the first drive output.

At block 1408, the process 1400 can include determining a state of the engagement assembly based on the amount of force applied by the first drive output and/or the position of the first drive output. For example, control circuitry can determine whether the amount of force applied by the first drive output is above/below one or more thresholds, within a range of predetermined forces, etc. As such, in some instances the control circuitry can compare the amount of force applied by the first drive output to one or more thresholds. Further, the control circuitry can compare the position of the first drive output to one or more predetermined/reference positions, a range of positions, etc. The state of the engagement assembly can indicate whether the engagement assembly is engaged/disengaged, whether a retention feature of the engagement assembly is open/closed (or partially open/closed), whether an elongate shaft of a medical instrument is received/properly received in the engagement assembly, etc.

In one illustration, the control circuitry can determine that the engagement assembly is associated with an engaged state (e.g., a fully engaged state) when the amount of force applied by the first drive output is less than a first threshold. Example engaged states are illustrated in FIGS. 8-1 through 8-2 and 9-1 through 9-2. Further, the control circuitry can determine that the engagement assembly is associated with a first disengaged state (e.g., intermediate state) when the amount of force applied by the first drive output is more than the first threshold and less than a second threshold. The first disengaged state can be a state in which an actuator of the engagement assembly is disengaged from the elongate shaft and a retention feature of the engagement assembly is substantially closed to retain the elongate shaft, such as the engagement state illustrated in FIGS. 10-1 and 10-2. Moreover, the control circuitry can determine that the engagement assembly is associated with a second disengaged state (e.g., fully open state) when the amount of force applied by the first drive output is more than the second threshold. An example of such disengaged state is illustrated in FIGS. 11-1 and 11-2.

In another illustration, the control circuitry can determine a reference position(s) that is associated with more than a threshold amount of force change (e.g., a spike in force applied by the first drive output). For example, the control circuitry can actuate the first drive output to a hard-stop position and/or actuate in a direction towards a hard-stop position when the instrument feeder device is first coupled to a robotic arm. The control circuitry can detect a spike(s) in force applied by the first drive output during such actuation and designate a position of the first drive output at that spike in force as a reference position (e.g., a transition position between an engaged state and disengaged state, a hard-stop position for the engagement assembly, or another position/state). Thereafter, the control circuitry can determine a state of the engagement assembly based on a proximity of a current position of the first drive output to the reference position (e.g., a proximity of a current rotational position relative to the reference rotational position).

In yet other illustrations, the control circuitry can determine a state of the engagement assembly in other manners based on the force applied by the first drive output and/or the position of the first drive output.

At block 1410, the process 1400 can include causing a second drive output to actuate to axially move the elongate shaft. For example, when an engagement assembly is positioned in an engaged state (e.g., ready to drive), control circuitry can control a second drive output of a robotic arm to cause actuation of a second drive input of the engagement assembly, wherein the second drive input can be configured to control axial motion of an elongate shaft. As such, the second drive output can cause the elongate shaft to move axially (e.g., insert or retract). In examples, the second drive output can be controlled based on a signal from an I/O device to insert/retract the elongate shaft, a system determination to insert/retract the elongate shaft (e.g., without having received user input), etc.

Figure 15:
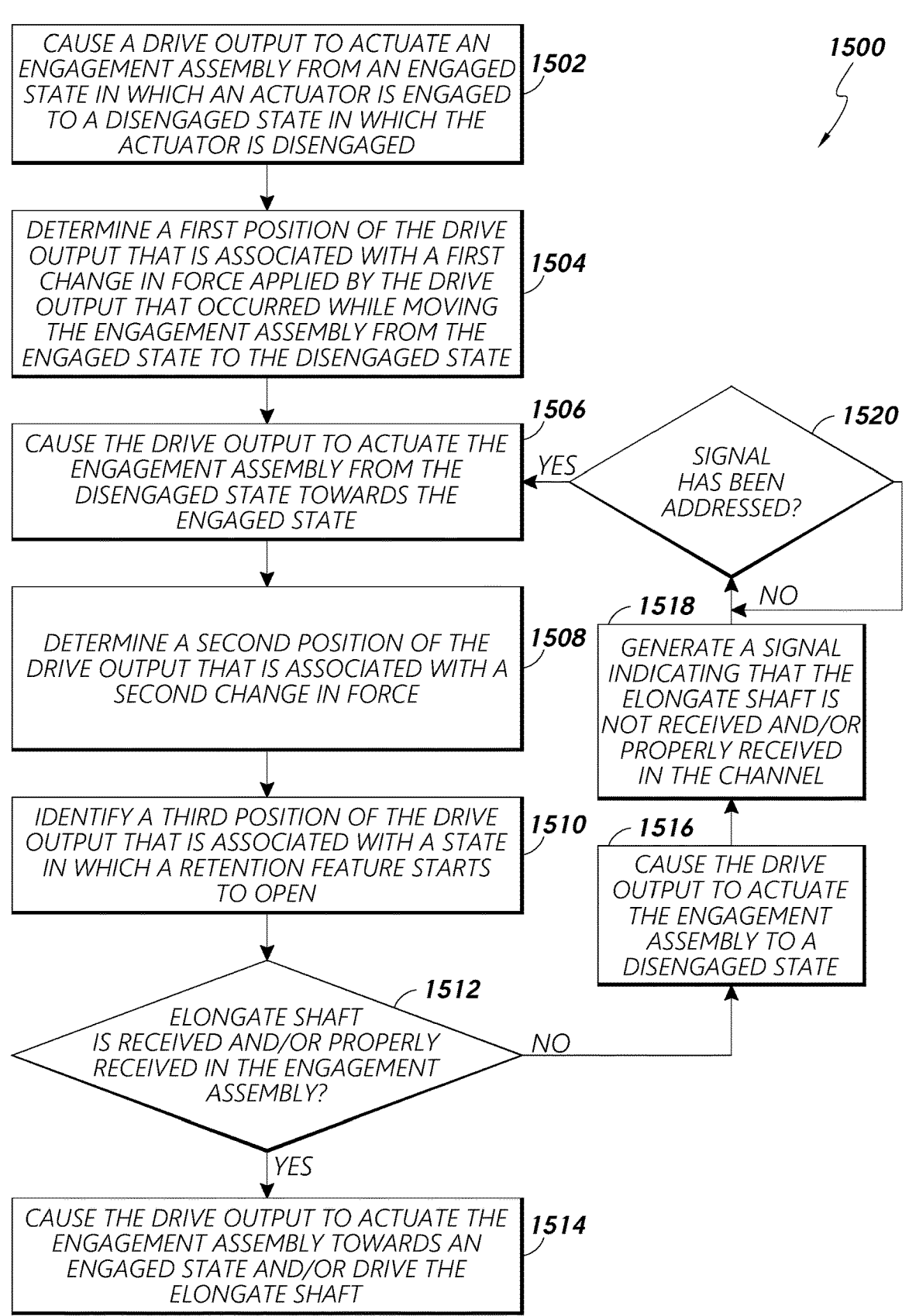
FIG. 15 illustrates an example process to determine whether an elongate shaft of a medical instrument is loaded/properly loaded into an instrument feeder device in accordance with one or more embodiments.

FIG. 15 illustrates the example process 1500 to determine whether an elongate shaft of a medical instrument is loaded/properly loaded into an instrument feeder device in accordance with one or more embodiments.

At block 1502, the process 1500 can include causing a drive output to actuate an engagement assembly from an engaged state in which an actuator is engaged to a disengaged state in which the actuator is disengaged. For example, control circuitry can cause a drive output of a robotic arm to actuate (e.g., rotate) to cause an associated drive input of an engagement assembly of an instrument feeder device coupled to the robotic arm to actuate (e.g., rotate). The actuation of the drive input can cause the engagement assembly to change from an engaged state (which may be a default state for the instrument feeder device) to a disengaged state. In some examples, the engagement assembly can transition to a fully disengaged/open state, such as that illustrated in FIGS. 11-1 and 11-2. The fully disengaged/open state can allow an instrument shaft to be loaded into the engagement assembly.

At block 1504, the process 1500 can include determining a first position of the drive output that is associated with a first change in force (e.g., torque) applied by the drive output that occurred while moving the engagement assembly from the engaged state to the disengaged state. For example, while transitioning the engagement assembly from the engaged state to the disengaged state, control circuitry can monitor an amount of force applied by the drive output. When the drive output experiences/applies more than a threshold amount of change in force to move the drive output by a particular amount (e.g., a threshold increase/decrease in force for a predetermined rotation amount), the control circuitry can identify the position of the drive output at that point (also referred to as "the initial position of force change" or "reference position"). In one illustration, in the context of FIG. 12, the control circuitry can transition the engagement assembly 532 from the engaged state 1204(4) to the disengaged state 1204(1) and detect a change in force that is applied by the drive output 1202 at position 1202(C), wherein such change is greater than a threshold.

At block 1506, the process 1500 can include causing the drive output to actuate the engagement assembly from the disengaged state towards the engaged state. For example, control circuitry can cause the drive output to actuate the engagement assembly from a fully disengaged/open state towards the engaged state. In some examples, this can occur after a predetermined period of time has passed from performing operation 1502/1504, upon detecting that an instrument base of a medical instrument is coupled to a robotic arm (e.g., a second robotic arm), after a predetermined period of time has passed from coupling the instrument base to the robotic arm (which can be based on starting a timer when the coupling occurs), and/or another event is detected. In one illustration, operation 1506 can be performed in an attempt to engage the engagement assembly with the elongate shaft of the medical instrument, such as upon determining/inferring that the elongate shaft has been loaded into the engagement assembly.

At block 1508, the process 1500 can include determining a second position of the drive output that is associated with a second change in force. In one example, the engagement assembly can transition from a fully disengaged/open state to an engaged state (e.g., block 1506). Once engagement is complete, the engagement assembly can move in a direction back towards a disengaged state and control circuitry can monitor an amount of force applied by the drive output. This can include moving by a relatively small amount in the disengagement direction (e.g., less than a particular amount). When the drive output experiences/applies more than a threshold amount of change in force to move the drive output by a particular amount (e.g., a threshold increase/decrease in force for a predetermined rotation amount), the control circuitry can identify the position of the drive output at that point (also referred to as "the secondary position of force change"). The threshold amount of force change can be greater than the threshold mentioned above for block 1504 and/or another threshold. As such, the secondary position of force change can be identified by detecting a change in force (contact force) in a disengagement direction. However, in other examples, the secondary position of force change can be detected in other manners, such as by detecting a change in force (contact force) in the engagement direction (e.g., loss of contact while transitioning to the engaged state). In some instances, once the secondary position of force change is identified, the engagement assembly can enter a free-floating zone.

At block 1510, the process 1500 can include identifying a third position of the drive output that is associated with a state in which a retention feature starts to open. For example, control circuitry can identify a position of the drive output that is associated with an intermediate state in which a cover of an engagement assembly is closed (but starts to open) and rollers are disengaged from the elongate shaft. In some instances, such position can be a predetermined position that is defined/referenced in relation to another position of the drive output, such as a position associated with a fully disengaged/open state, a position associated with an engaged state, a reference position, and/or another position. In one illustration, in the context of FIG. 12, the control circuitry can identify the position 1202(B) (where the cover

536 transitions between a closed and open state) based on knowing that the position 1202(B) is a predetermined rotational degrees from the position 1202(A)/1202(C) and/or another position (e.g., any reference position that can be detected based on a change in force).

At block 1512, the process 1500 can determine whether an elongate shaft of a medical instrument is received and/or properly received in the engagement assembly. For example, control circuitry can determine if the elongate shaft is loaded into a channel of the engagement assembly and/or or if the elongate shaft is properly loaded into the channel. Such determination can be based on a location of the second position (i.e., the secondary position of force change) relative to the first position and the third position (e.g., is the secondary position of force change between the first position and the third position).

In one illustration, in the context of FIG. 12, assume that an instrument shaft is not loaded into the engagement assembly 532. For instance, the engagement assembly 532 can transition (at block 1502) to a fully open/disengaged state to facilitate loading of the instrument shaft into the engagement assembly 532, but the instrument shaft is not loaded. The control circuitry can detect (at block 1504) the position 1202(C) as the initial position of force change. Here, the control circuitry can transition the engagement assembly 532 (at block 1506) from the fully open/disengaged state 1204(1) towards the engaged state 1204(3) and detect (at block 1508) a change in force that is applied by the drive output 1202 at position 1202(C) (i.e., the secondary position of force change). At block 1512, the control circuitry can determine that the instrument shaft is not loaded into the engagement assembly 532 based on the secondary position of force change (1202(C)) being the same as the initial position of force change (1202(C)). Here, the control circuitry determined the same position for both instances of force change. In a similar fashion, the control circuitry can determine that the instrument shaft is not loaded when the secondary position of force change is even closer to the position 1202(E) (e.g., the secondary position of force change is between the position 1202(C) and the position 1202(E)).

In another illustration, in the context of FIG. 13, assume that an instrument shaft is properly loaded into the engagement assembly 532. For instance, the engagement assembly 532 can transition (at block 1502) to a fully open/disengaged state, and the instrument shaft is loaded by a user. The control circuitry can determine (at block 1504) the position 1202(C) as the initial position of force change when transitioning to the fully open/disengaged state. Further, the control circuitry can transition the engagement assembly 532 (at block 1506) from the fully open/disengaged state 1204(1) towards the engaged state 1204(3) and can detect (at block 1508) a change in force that is applied by the drive output 1202 at the position 1202(C)(1) (i.e., the secondary position of force change). The control circuitry can identify (at block 1510) the position 1202(B) as the third position (i.e., the intermediate position). At block 1512, the control circuitry can determine that the instrument shaft is properly loaded into the engagement assembly 532 based on the secondary position of force change (1202(C)(1)) being between (with respect to a rotation) the initial position of force change (1202(C)) and the intermediate position (1202(B)).

In a further illustration, assume that an instrument shaft is improperly loaded into the engagement assembly 532, such as by positioning the instrument shaft partially with the channel 534 in a manner that prevents the cover 536 from fully closing. For instance, the engagement assembly 532 can transition (at block 1502) to a fully open/disengaged state, and the instrument shaft is positioned at a top portion of the channel 534. The control circuitry can determine (at block 1504) the position 1202(C) as the initial position of force change. Further, the control circuitry can transition the engagement assembly 532 (at block 1506) from the fully open/disengaged state 1204(1) towards the engaged state 1204(3) and detect (at block 1508) a change in force that is applied by the drive output 1202 at a position (i.e., the secondary position of force change) before position 1202 (B), which can occur due to the improper loading of the instrument shaft. The control circuitry can identify (at block 1510) the position 1202(B) as the third position (i.e., intermediate position). At block 1512, the control circuitry can determine that the instrument shaft is improperly loaded into the engagement assembly 532 based on the secondary position of force change being located before the intermediate position (1202(B)).

In a yet further illustrations, an instrument shaft can be determined to be improperly loaded when the second position of force change is after/past the initial position of force change.

In any event, if it is determined at 1512 that the elongate shaft is received/properly received in the engagement assembly, the process 1500 can proceed to block 1514 (i.e., the YES branch). Alternatively, if it is determined that the elongate shaft is not received/properly received in the engagement assembly, the process 1500 can proceed to block 1516 (i.e., the NO branch).

At block 1514, the process 1500 can include causing the drive output to actuate the engagement assembly towards/to an engaged state and/or driving the elongate shaft. For example, control circuitry can cause the drive output to actuate the engagement assembly to an engaged state, wherein the control circuitry can drive the elongate shaft/ medical instrument with the elongate shaft properly loaded in the engagement assembly. In one illustration, in the context of FIG. 13, the control circuitry can cause the engagement assembly 532 to transition to the state 1204(4), and then, drive/control the medical instrument (e.g., receive input from a user to insert/retract and control the elongate shaft to insert/retract).

At block 1516, the process 1500 can include causing the drive output to actuate the engagement assembly to a disengaged state. For example, control circuitry can cause the drive output to actuate the engagement assembly to a fully open/disengaged state to facilitate loading/reloading of an elongate shaft of a medical instrument. In one illustration, in the context of FIG. 12, the control circuitry can cause the engagement assembly 532 to transition to the state 1204(1).

At block 1518, the process 1500 can include generating a signal indicating that the elongate shaft is not received/ properly received in the channel. For example, control circuitry can generate a signal (e.g., fault/error signal) indicating that the elongate shaft is not loaded/properly loaded in the engagement assembly and/or send the signal to another component/device to facilitate additional processing. In some instances, the signal can cause a notification to be provided via a user interface, wherein such notification can inform a user to load/reload an elongate shaft of a medical instrument.

At block 1520, the process 1500 can include determining if the signal has been addressed. For example, control circuitry can determine (i) if user input has been received indicating that an elongate shaft has now been loaded/ properly loaded, (ii) if a period of time has passed from providing a fault/error notification, (iii) if data from a sensor (e.g., light barrier sensor, force sensor, etc.) on the instrument feeder device/engagement assembly indicates that the elongate shaft is loaded/properly loaded, (iv) if (based on data from a shape sensor in the elongate shaft, for example) the elongate shaft is positioned properly relative to the instrument feeder device/engagement assembly, and/or another determination.

If it is determined that the signal has been addressed, the process 1500 can return to block 1506 (i.e., the YES branch). Alternatively, if it is determined that the signal has not been addressed, the process 1500 can return to block 1520 (i.e., the NO branch) and perform the operation 1520 again (after a period of time has passed, for instance).

Figures 1, 16:
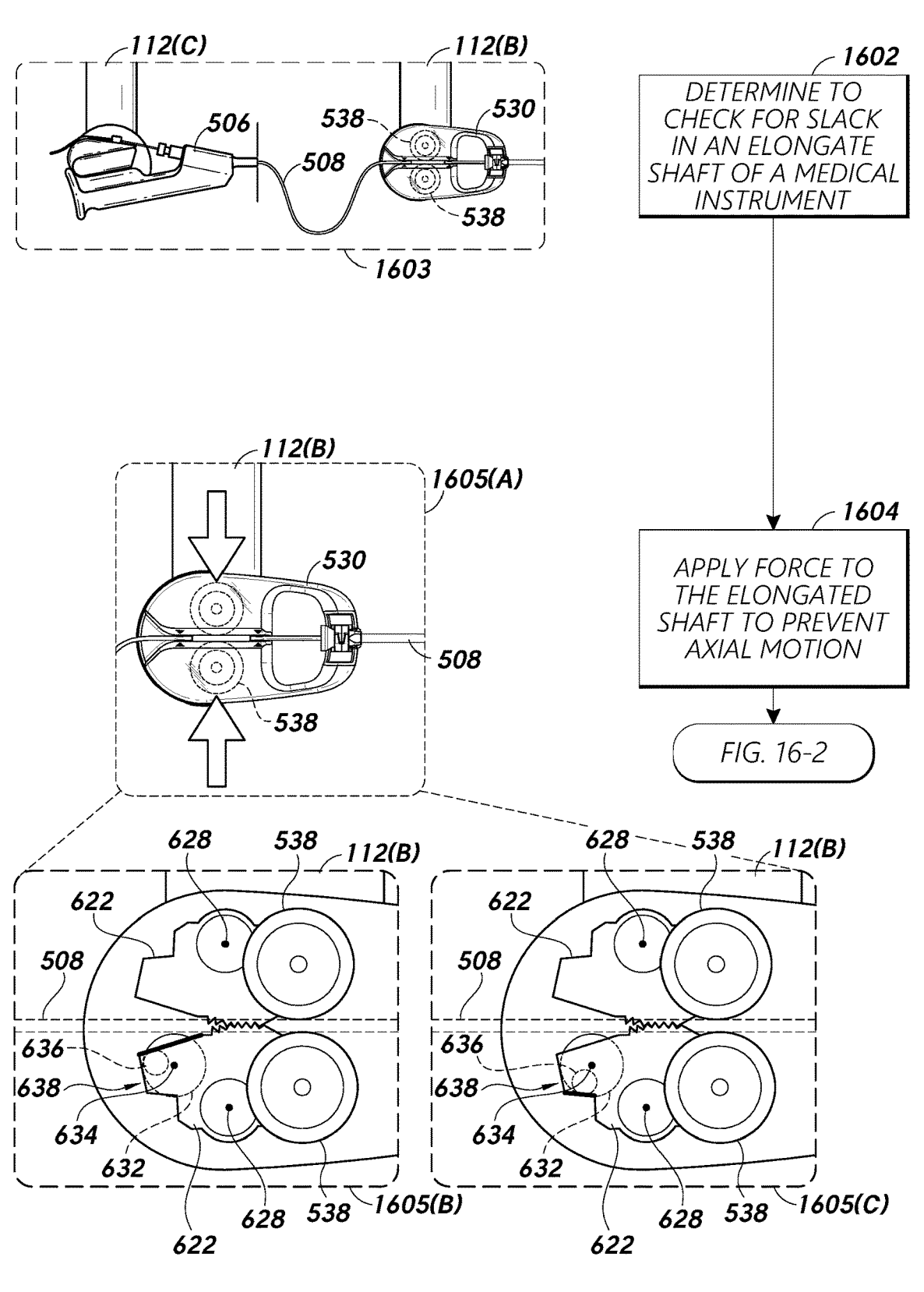
Figures 1, 2, 3, 16:
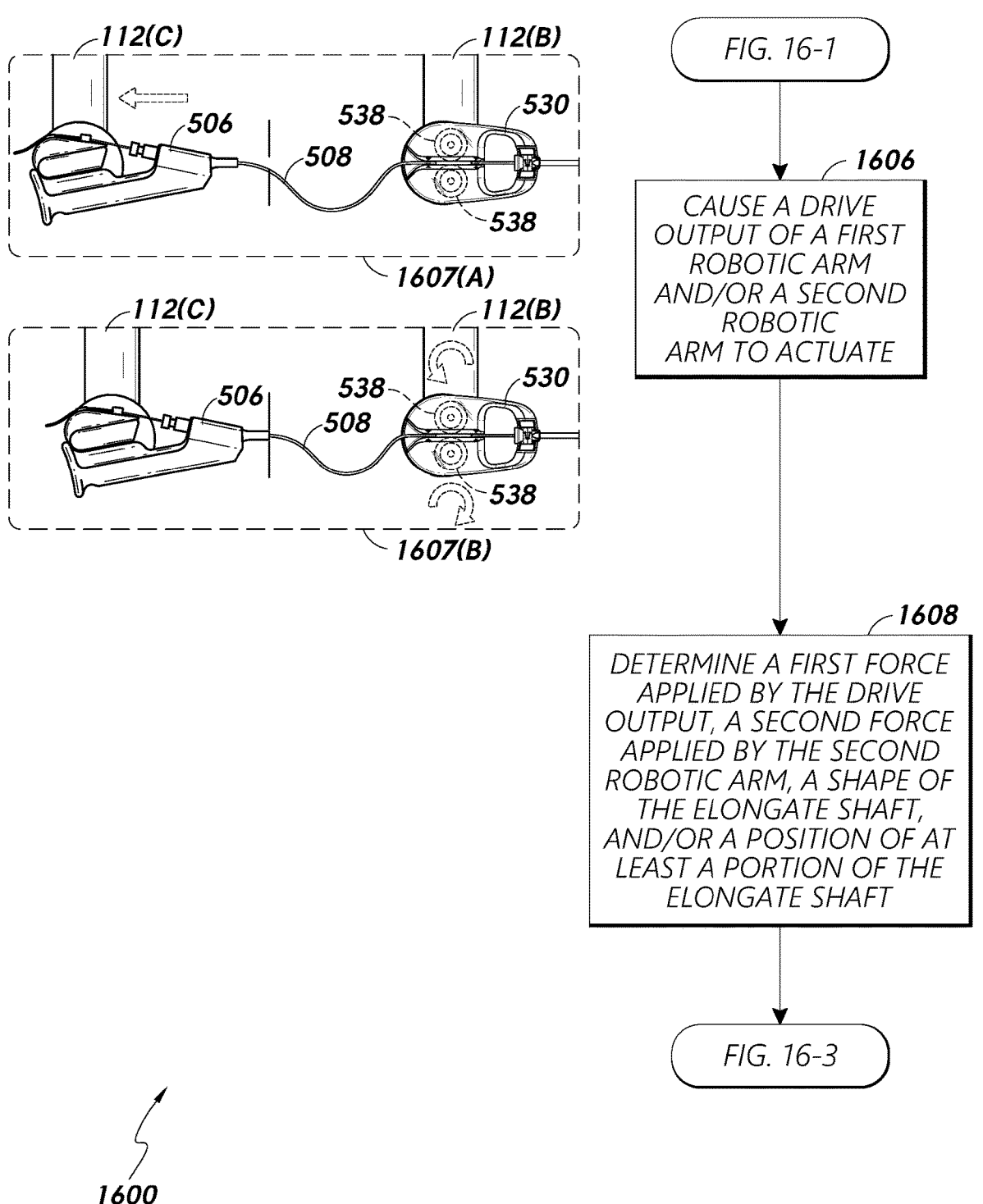
Figures 3, 16:
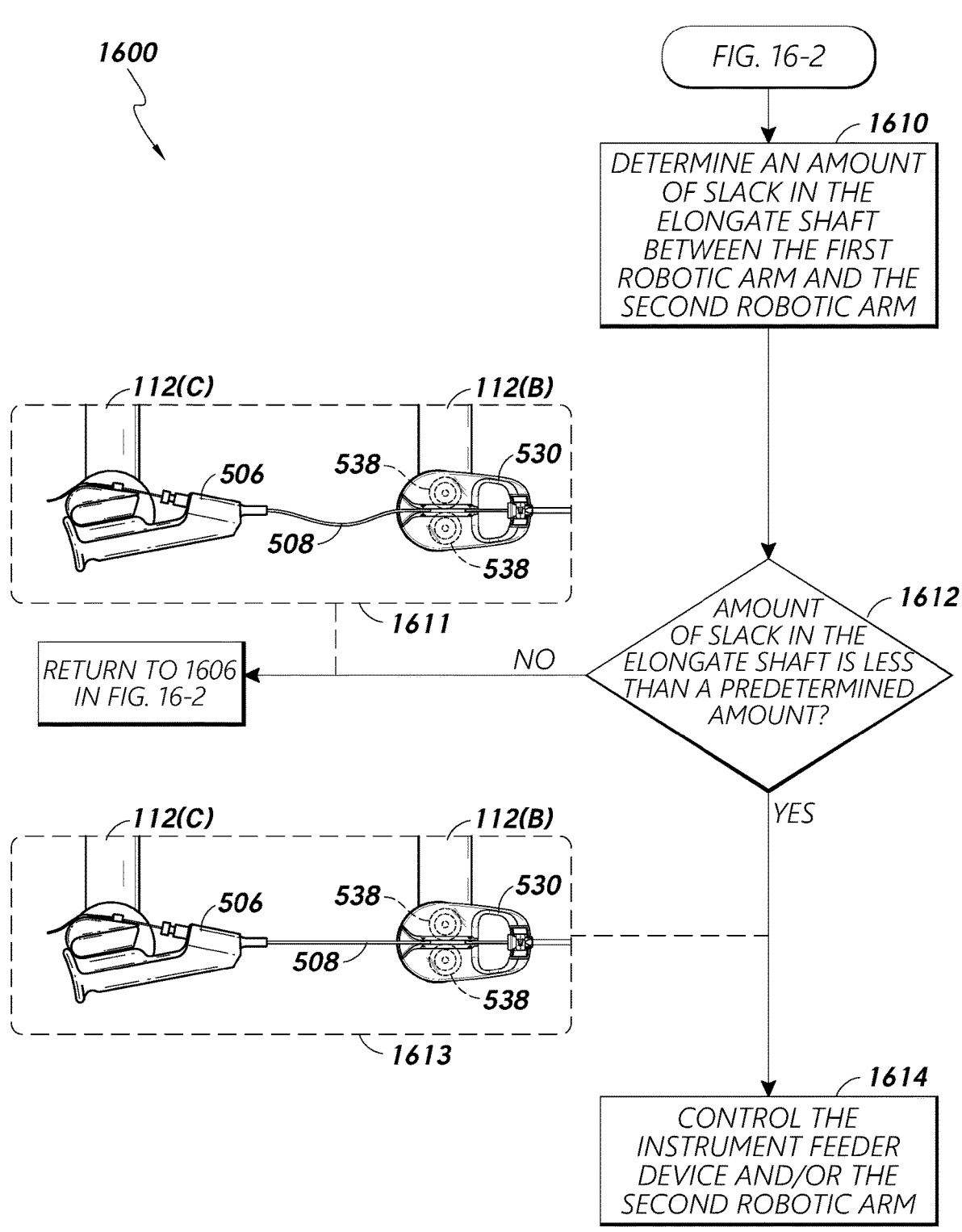

FIGS. 16-1 and 16-2 illustrate the example process 1600 to determine and/or remove slack in an elongate shaft of a medical instrument in accordance with one or more embodiments.

In FIG. 16-1, at block 1602, the process 1600 can include determining to check for slack in an elongate shaft of a medical instrument. For example, the medical instrument can include the elongate shaft and an instrument handle, wherein the elongate shaft can couple to/engage with an instrument feeder device coupled to a first robotic arm/component and the instrument handle can be coupled to a second robotic arm/component. In some instances, control circuitry can determine to evaluate an amount of slack in the elongate shaft between the instrument handle and the instrument feeder device. Such evaluation can be initiated when a determination is made to insert (or retract, in some cases) the elongate shaft, to roll the instrument shaft, to enable an admittance control mode for a robotic arm, that a procedure is complete, that a period of time has passed from a last check for slack in the elongate shaft, that the medical instrument has recently been coupled to a robotic arm(s) (e.g., an instrument handle/elongate shaft were loaded to start driving the medical instrument), that a procedure is about to begin, etc. In some cases, the determination is based on receiving user input, system processing (e.g., the system determining that an event has occurred), etc.

In one illustration, a check for slack in the elongate shaft can be initiated when user input is received to insert the elongate shaft or it is otherwise determined to insert the elongate shaft. To insert the elongate shaft of the medical instrument, the robotic arms can operate in a cooperative manner. For instance, a first robotic arm can be coupled to the instrument feeder device, while a second robotic arm can be coupled to the instrument handle. The instrument feeder device can cause axial motion of the elongate shaft in an insertion direction, while the second robotic arm moves closer to the first robotic arm in a manner correlated to the speed of the axial motion of the shaft. If there is slack in the elongate shaft (e.g., a service loop) when the shaft is inserted, a curvature of the slack may increase, which can potentially damage the elongate shaft (e.g., by bending the shaft more than a threshold amount) and/or cause a delay in the procedure to reload/replace the medical instrument. As such, a check for slack in the elongate shaft can be initiated to prevent such undesirable issues.

In another illustration, a check for slack in the elongate shaft can be initiated when a roll the instrument shaft is instructed, an admittance control mode is enabled/requested for a robotic arm, and/or another event occurs that is associated with implementing an intermediate/disengaged state for the instrument feeder device. For example, during a procedure/setup of the procedure, a physician can provide user input to enable an admittance control mode to manual move a robotic arm coupled to the instrument feeder device and/or provide user input to roll the instrument shaft. In response to such user input, the control circuitry can generate/receive a signal to insert the shaft/enable the admittance control mode. As noted above, the admittance control mode can allow the physician to manually adjust the robotic arm and/or an access sheath coupled to the robotic arm. To facilitate movement of the robotic arm/access sheath and/or a roll of the elongate shaft, the instrument feeder device may be transitioned to an intermediate state in which the instrument feeder device is disengaged from the elongate shaft and the elongate shaft is retained within the instrument feeder device in a manner that allows movement of the instrument shaft, such as the state illustrated in FIGS. 10-1 and 10-2. If there is slack in the elongate shaft (e.g., a service loop) when the instrument feeder device disengages from the elongate shaft (e.g., rollers separate from the shaft), the elongate shaft may move in an insertion direction as the energy/service loop is released, which can cause undesirable insertion of the elongate shaft. This can cause harm to a patient (e.g., due to a tip of the elongate shaft contacting tissue of a patient with a relatively high force). As such, a check for slack in the elongate shaft can be initiated to prevent such undesirable issues.

In yet another illustration, a check for slack can be initiated when a determination is made that a procedure has been completed. For example, upon completing a procedure, a physician may desire to decouple the medical instrument from one or more robotic arms (e.g., remove the elongate shaft from the instrument feeder device). This can involve transitioning an instrument feeder device to a fully open/disengaged state. As similarly discussed above, if there is slack in the elongate shaft when the instrument feeder device disengages from the elongate shaft, the elongate shaft may move in an insertion direction. As such, a check for slack can be initiated to prevent such issue.

In further illustrations, a check for slack can be initiated periodically, when a robotic arm is idle (e.g., has not been moved for a period of time), the medical instrument is coupled to a robotic arm, and/or upon the occurrence of a variety of other types of events/determinations.

In the example shown in block 1603 in FIG. 16-1, the medical instrument can include the elongate shaft 508 coupled to/engaged with the instrument feeder device 530 (which is coupled to the first robotic arm 112(B)) and the instrument handle 506 coupled to the second robotic arm 112(C). The elongate shaft 508 is shown with some amount of slack for illustrative purposes.

At block 1604, the process 1600 can include applying force to the elongate shaft of the medical instrument to prevent axial motion of the elongate shaft. For example, the control circuitry can control one or more drive outputs of the first robotic arm (that is coupled to the instrument feeder device) to actuate to cause the instrument feeder device to apply force to the elongate shaft to prevent axial movement of a portion of the elongate shaft that is positioned within the instrument feeder device (e.g., to pinch the elongate shaft). This force may be applied to prevent retraction (or insertion, in some cases) of the elongate shaft 508 from a patient while other aspects of the process 1600 or other processes are performed, as discussed below.

In the example shown in blocks 1605(A)-1605(C) of FIG. 16-1, the rollers 538 can be controlled to apply force to the elongate shaft 508, such as to pinch the elongate shaft 508 between the rollers 538 with a particular amount of force (e.g., more than a spring force that biases the rollers 538 towards each other). For instance, as described above, the instrument feeder device 530 can include carrier plates 622 that are rotated based on a position of the off-axis protrusion 636 within the pocket 638. Rotation/movement of the carrier plates 622 can cause the rollers 538 to move closer or farther away from each other, to thereby position the rollers 538 and/or adjust an amount of force that is applied to the elongate shaft 508.

To illustrate, the open/close drive shaft 632 can be rotated clockwise with respect to the image of FIG. 16-1 (by a drive input, not illustrated) to cause the off-axis protrusion 636 (that is coupled to the open/close drive shaft 632) to contact a first surface/edge within the pocket 638, illustrated with a darker line in block 1605(B). Force can be applied to the first surface by the off-axis protrusion 636 to cause the carrier plates 622 to rotate around the axes 628, thereby causing the rollers 538 to move in a direction away from each other (e.g., disengage/open state). In contrast, the open/close shaft 632 can be rotated counterclockwise to cause the off-axis protrusion 636 to move towards and contact a second surface, illustrated with a darker line in block 1605(C). The off-axis protrusion 636 can apply force to the second surface to cause the carrier plates 622 to rotate in the opposite direction and cause the rollers 538 to apply addition force to the elongate shaft 508. In some instances, such as that illustrated, the off-axis protrusion 636 can move freely between the first surface and the second surface of the pocket 638 (e.g., not apply any force to either surface). Here, a spring force can cause the rollers 538 to apply force to the elongate shaft 508.

In the example of FIG. 16-1, the elongate shaft 508 may be positioned between the rollers 538 to facilitate driving of the elongate shaft 508. At block 1604, the rollers 538 can be controlled to apply force to the elongate shaft 508, as shown in block 1605(C). This can prevent the elongate shaft 508 from slipping between the rollers 538 when other acts are performed, such as the robotic arm 112(C) being moved away from the robotic arm 112(B), as discussed in further detail below. For example, this may prevent retraction of the elongate shaft 508 from the patient that is not commanded/instructed. This process of applying force to the elongate shaft 508 can be referred to as an "active pinch."

At block 1606 in FIG. 16-2, the process 1600 can include causing a drive output(s) of a first robotic arm to actuate and/or a second robotic arm to actuate. For example, the instrument feeder device can include one or more drive inputs that are configured to control axial motion of the elongate shaft, such as to insert or retract the shaft, wherein the one or more drive inputs can be configured to couple to one or more drive outputs of the first robotic arm. In examples, the control circuitry can cause the one or more drive outputs of the first robotic arm to actuate (e.g., rotate) to cause axial motion of the elongate shaft. Alternatively, or additionally, the control circuitry can cause the second robotic arm that is coupled to the instrument handle to move in a direction away from the first robotic arm. The control circuitry can cause the one or more drive outputs and/or the second robotic arm to actuate by a particular amount, in some cases. In examples, the second robotic arm is moved away from the first robotic arm (or vice versa) and/or the instrument feeder device moves the elongate shaft in an insertion direction to the extent that slack (if any) is removed/reduced and/or tension is applied to the elongate shaft. Such tension can be detected by the control circuitry, as discussed below.

In the example shown in block 1607(A) of FIG. 16-2, the robotic arm 112(C) is moved in a direction away from the robotic arm 112(B) (e.g., in a retraction direction). This can occur while the robotic arm 112(B) remains relatively stationary and/or without actuating the drive outputs of the robotic arm 112(B) that are coupled to the instrument feeder device 530 to facilitate rotation of the rollers 538. In some instances, the robotic arm 112(C) is moved in a direction away from the robotic arm 112(B) while the rollers 538 actively pinch/apply force to the elongate shaft 508. In other words, the block 1604 can be performed in instances where the robotic arm 112(C) is moved away from the robotic arm 112(C). This may prevent undesired retraction of the elongate shaft 508 from the patient (e.g., retraction that is not commanded/instructed).

Further, in the example shown in block 1607(B) of FIG. 16-2, the rollers 538 are actuated to move the elongate shaft 508 in an insertion direction. This can occur while the robotic arm 112(C) remains relatively stationary (e.g., without causing the robotic arm 112(C) to move).

At block 1608, the process 1600 can include determining a first force applied by/to (or detected by) the drive output, a second force applied by the second robotic arm, a shape of the elongate shaft, and/or a position of at least a portion of the elongate shaft. For example, the control circuitry can detect a first force (e.g., torque) applied by a drive output(s) of the first robotic arm to an instrument feeder device to control axially motion of the elongate shaft. In the example of block 1607(B), the control circuitry can determine/detect a force applied by/to the drive outputs of the robotic arm 112(B) when the rollers 538 are idle or moving (e.g., a force to maintain or change a rotational position of the rollers 538). Additionally, or alternatively, the control circuitry can detect a second force applied by/to the second robotic arm when the second robotic arm is idle or moving (e.g., to control a position of the second robotic arm). This force can account for an initial reference force applied by the second robotic arm when there is no tension on the elongate shaft, as discussed in further detail below. In the example of block 1607(A), the control circuitry can determine a force applied by the robotic arm 112(C) to maintain (or move) a position of the robotic arm 112(C). Further, the control circuitry can receive/generate shape sensing data indicating a shape of the elongate shaft (which can include data indicating tensile stress, such as from stress sensing fibers), position sensor data indicating a position of at least a portion of the elongate shaft (e.g., a position of a tip of the elongate shaft or another portion of the elongate shaft that is associated with a sensor), position data indicating a position of the first/second robotic arms, and/or other data.

In FIG. 16-3, at block 1610, the process 1600 can include determining an amount of slack in the elongate shaft between the first robotic arm and the second robotic arm. For example, the control circuitry can determine an amount of slack in the elongate shaft based on an amount of the first force applied by/to (or detected by) the drive output to control axial motion of the elongate shaft, an amount of the second force applied by the second robotic arm, a shape indicated by the shape sensing data, and/or a position indicated by the position data for the elongate shaft/robotic arms. In some instances, the control circuitry can determine that the elongate shaft is relatively straight when the first force (drive output force) is more than a first threshold amount, the second force (robotic arm force) is more than a second threshold amount (which can be the same or different than the first threshold), the shape sensing data indicates that the elongate shaft is relative straight, and/or the position data for the elongate shaft/robotic arms indicates that the elongate shaft is relative straight.

In one illustration, the control circuitry can use position data for the elongate shaft to determine the position of the tip of the elongate shaft. The control circuitry can also determine the position of the robotic arms (such as a distance between the robotic arms) and/or identify dimensions of the elongate shaft (e.g., a known/predetermined length of the shaft). Based on such information, the control circuitry can calculate the length of the elongate shaft that is between the robotic arms. If the length of the elongate shaft that is between the robotic arms is greater than the distance between the robotic arms, the control circuitry can determine that there is slack in the elongate shaft. In examples, the control circuitry can use the information discussed above to calculate the amount of slack between the robotic arms.

At block 1612, the process 1600 can include determining if the amount of slack in the elongate shaft is less than a predetermined amount. For example, the control circuitry can determine if the amount of slack in the elongate shaft between the first and second robotic arms is relatively small (e.g., there is zero/no slack in the shaft, the amount of slack is less than a threshold amount, etc.)

If it is determined that the amount of slack in the elongate shaft is not less than the predetermined amount, the process 1600 can return to block 1606 in FIG. 16-2 (i.e., the NO branch) to cause the drive output of the first robotic arm and/or the second robotic arm to actuate again, such as by a particular amount. This can be repeated any number of times to remove any slack in the elongate shaft and/or apply tension to the elongate shaft. In the example shown in block 1611 of FIG. 16-3, the elongate shaft 508 includes some amount of slack. As such, the block 1611 is associated with returning to block 1606.

If it is determined that the amount of slack in the elongate shaft is less than the predetermined amount (e.g., the elongate shaft is substantially free of slack), the process 1600 can proceed to block 1614 (i.e., the YES branch). In the example shown in block 1613 of FIG. 16-3, the elongate shaft 508 is slack free. As such, the block 1613 is associated with proceeding to the block 1614.

At block 1614, the process 1600 can include controlling the instrument feeder device and/or the second robotic arm. For example, the control circuitry can control the instrument feeder device to axially move the elongate shaft and/or the second robotic arm to move in a cooperative manner to insert the elongate shaft, such as for any remaining insertion amount that is instructed and has not yet been completed. In particular, the instrument feeder device can cause axial motion of the elongate shaft in an insertion direction (e.g., using rollers), while the second robotic arm moves closer to the first robotic arm in a manner correlated to the speed of the axial motion of the elongate shaft (e.g., a rotational speed of the rollers). Such movement can continue until the elongate shaft is inserted to the amount determined/instructed. Alternatively, or additionally, the control circuitry can cause the instrument feeder device to disengage from the elongate shaft, which can facilitate a roll of the elongate shaft (by implementing an intermediate state for the instrument feeder device), movement of a robotic arm in an admittance control mode (by implementing an intermediate state for the instrument feeder device), and/or removal of the elongate shaft (by implementing a fully open/disengaged state), etc.

In some instances, the control circuitry can cause tension (e.g., over tension) in the elongate shaft to loosen, such as before performing the operation of block 1614. For example, the control circuitry can cause the drive output of the first robotic arm to axially move the elongate shaft in a retraction direction by a relatively small amount and/or the second robotic arm to actuate in a direction towards the first robotic arm by a relatively small amount. Such movement can loosen tension on the elongate shaft, which may have been applied while performing the process 1600.

FIG. 17 illustrates the example process 1700 to determine and/or remove slack in an elongate shaft of a medical instrument in the context of inserting the elongate shaft in accordance with one or more embodiments. In some instances, the process 1700 can be initiated when it is determined to insert the elongate shaft, such as upon receiving user input to insert the shaft, a system determination, etc.

At block 1702, the process 1700 can include determining an initial force of a first robotic arm coupled to an instrument base of a medical instrument. For example, control circuitry can determine an initial/reference force applied by the first robotic arm that is coupled to the instrument base when there is no tension on the elongate shaft. Such force can be determined before the elongate shaft is inserted.

At block 1704, the process 1700 can include determining whether or not to insert an elongate shaft of the medical instrument. For example, the control circuitry can determine whether a user input/input signal is received requesting that the elongate shaft be inserted, a determination is made to insert the elongate shaft, etc.

If a determination is made to insert the elongate shaft, the process 1700 can proceed to block 1706 (i.e., the YES branch). Alternatively, if a determination is made to not insert the elongate shaft, the process 1700 can return to block 1704 (i.e., the NO branch). As such, the control circuitry can wait for an insertion instruction to be received/determined.

At block 1706, the process 1700 can include determining a drive output force associated with a drive output and/or a robotic arm force associated with a robotic arm. For example, the control circuitry can determine a drive force (e.g., torque) applied by a drive output(s) that is coupled to an instrument feeder device to facilitate insertion/retraction of the shaft. Further, the control circuitry can determine a robotic arm force applied by a robotic arm that is coupled to an instrument base. In some instances, the robotic arm force can account for a current force applied/implemented to control a position of the robotic arm (also referred to as "the external force, net instrument force, or resultant force") and/or the initial/reference force applied by the robotic arm (determined at block 1702). For example, the robotic arm force can be calculated by subtracting the initial/reference force from the external force (i.e., robotic arm force=external force−reference force). The robotic arm force can refer to the external force (e.g., sensed by the robotic arm) with the gravity force excluded. However, the robotic arm force can be calculated in other manners.

At block 1708, the process 1700 can include determining whether the drive output force is greater than a first threshold and/or the robotic arm force is greater than a second threshold. The second threshold can be the same as or different than the first threshold. For example, the control circuitry can determine whether the drive output force determined at block 1706 and/or the robotic arm force determined at block 1706 are greater than their respective thresholds, which can indicate that there is tension on the elongate shaft between the first and second robotic arms. Although two thresholds are used in this example, the techniques can be implemented with a single threshold, wherein the drive output force and the robotic arm force can be combined and compared to the single threshold.

If is determined that the drive output force is greater than the first threshold and/or the robotic arm force is greater than the second threshold, the process 1700 can proceed to block 1712 (i.e., the YES branch). Alternatively, if it is determined that the drive output force is not greater than the first threshold and/or the robotic arm force is not greater than the second threshold, the process 1700 can proceed to block 1710 (i.e., the NO branch).

At block 1710, the process 1700 can include controlling the instrument feeder device to insert the elongate shaft without actuating the first robotic arm that is coupled to the instrument base. For example, the control circuitry can control a drive output to cause the instrument feeder device to insert the elongate shaft, while preventing the first robotic arm that is coupled to the instrument base from actuating more than a threshold amount (e.g., enabling the first robotic arm to move less than a threshold amount). That is, the control circuitry may not actively cause the first robotic arm to move, but allow the first robotic arm to move a relatively small amount (e.g., less than a threshold amount) if some amount of force is exerted on the first robotic arm due to tension applied to the elongate shaft, for example. In any event, the control circuitry can cause the elongate shaft to be inserted by a particular amount, which can be an incremental amount that is within an insertion limit defined by user input/processing. The operation 1710 can be repeated any number of times until the tension on the elongate shaft reaches more than a threshold (as determined at block 1708) and/or until an insertion limit is reached. As such, the elongate shaft may not generally be inserted more than an amount requested by user input and/or a system.

At block 1712, the process 1700 can include controlling the instrument feeder device and the first robotic arm that is coupled to the instrument base. For example, the control circuitry can control the instrument feeder device to axially move the elongate shaft in an insertion direction and the first robotic arm (that is coupled to the instrument base) to move in an insertion direction to insert/continue inserting the elongate shaft, such as for any remaining insertion amount that is instructed and has not yet been completed. The instrument feeder device and the first robotic arm can actuate in a cooperative manner to insert the elongate shaft.

In some instances, the control circuitry can cause tension (e.g., over tension) in the elongate shaft to loosen, such as before performing the operation of block 1712. For example, the control circuitry can cause the drive output of the second robotic arm to control the instrument feeder device to axially move the elongate shaft in a retraction direction by a relatively small amount and/or the first robotic arm that is coupled to the instrument handle to actuate in a direction towards the second robotic arm by a relatively small amount. Such movement can loosen tension on the elongate shaft, which may have been applied while performing the process 1700. In examples, the tension can be loosened during insertion, such as by causing the instrument feeder device to insert the elongate shaft at a first rate and causing the first robotic arm that is coupled to the instrument handle to move towards the second robotic arm at a second rate that is faster than the first rate.

In examples, the process 1700 can be performed to remove any slack in the elongate shaft of the medical instrument. Thereafter, when an insertion/retraction command is received, the control circuitry can control the instrument feeder device and the robotic arm that is coupled to the instrument base to move in a cooperative manner to insert/retract the elongate shaft.

Figures 1, 18:
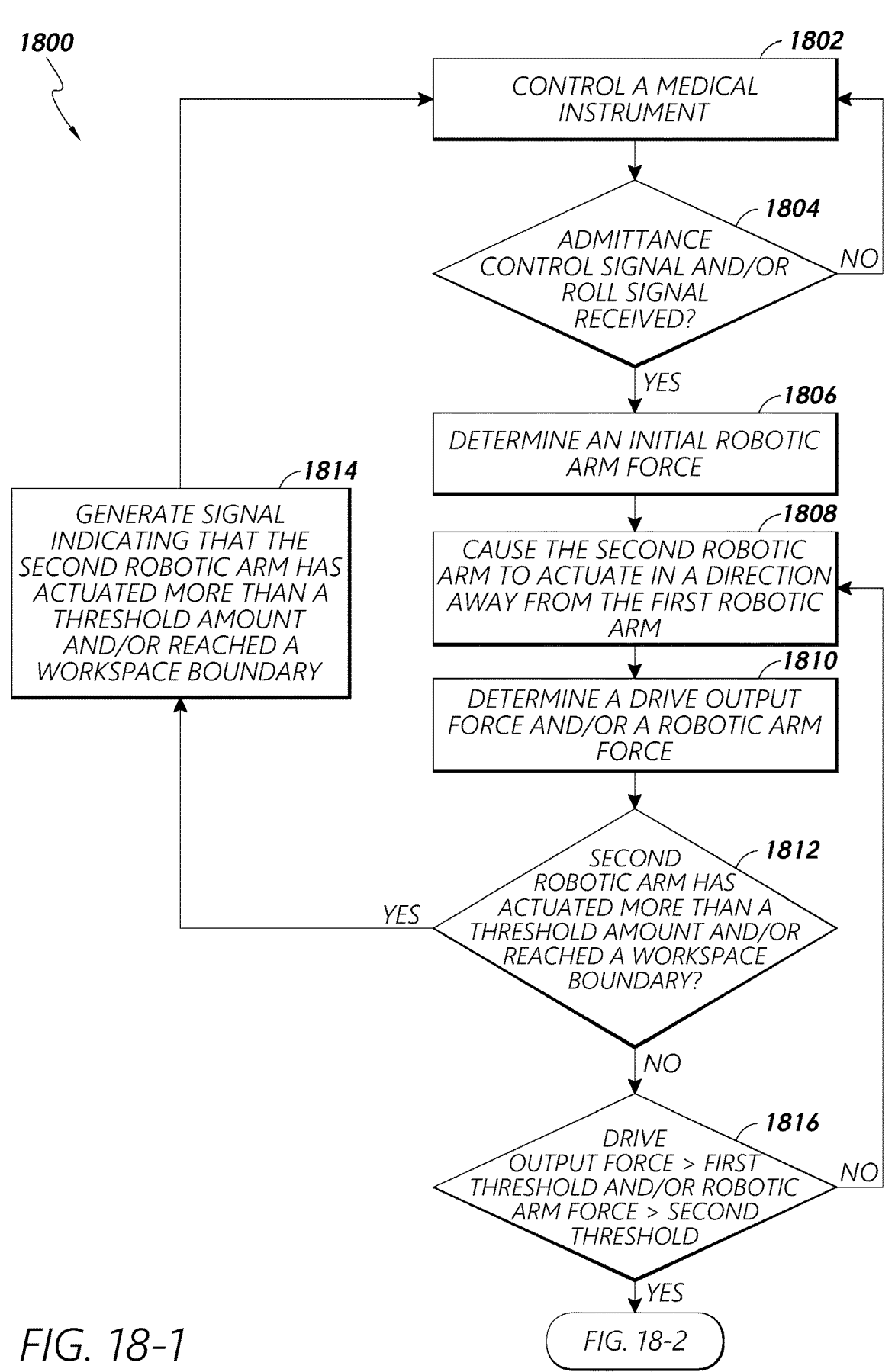

FIGS. 18-1 and 18-2 illustrate the example process 1800 to determine and/or remove slack in an elongate shaft of a medical instrument in the context of enabling an admittance control mode and/or rolling the elongate shaft in accordance with one or more embodiments. In some instances, the process 1800 can be initiated when it is determined to disengage an instrument feeder device from the elongate shaft (e.g., transition to an intermediate state, a fully open/disengaged state, etc.), such as upon receiving input to enable an admittance control mode for a robotic arm, receiving input to roll the elongate shaft, etc. However, the process 1800 can be initiated at other times and/or for other situations where the elongate shaft may include slack.

In FIG. 18-1, at block 1802, the process 1800 can include controlling a medical instrument. For example, a medical instrument can include an elongate shaft that is coupled to a first robotic arm (via an instrument feeder device) and/or a handle/base that is coupled to a second robotic arm. Control circuitry can control the first robotic arm, the second robotic arm, and/or another component during normal driving of the medical instrument, such as to manipulate the elongate shaft and/or handle of the medical instrument.

At block 1804, the process 1800 can include determining whether an admittance control signal and/or a roll signal is received. For example, control circuitry can receive a signal to enable an admittance control mode for a robotic arm (e.g., coupled to an instrument feeder device) and/or a signal to roll the elongate shaft of the medical instrument. Based on such signal, the control circuitry can determine to transition the instrument feeder device to a disengaged state (e.g., an intermediate state, a fully open/disengaged state, etc.).

If an admittance control signal and/or a roll signal is received, the process can proceed to block 1806 (i.e., the YES branch). Alternatively, if an admittance control signal and/or a roll signal is not received, the process 1800 can return to block 1802 (i.e., the NO branch) and proceed with normal control/driving of the medical instrument.

At block 1806, the process 1800 can include determining an initial/reference robotic arm force. For example, control circuitry can determine an initial/reference force applied by the second robotic arm that is coupled to the instrument base when there is no tension on the elongate shaft. Such force can be determined before the admittance control mode is enabled and/or the roll occurs.

At block 1808, the process 1800 can include causing the second robotic arm to actuate in a direction away from the first robotic arm. For example, the control circuitry can cause the second robotic arm that is coupled to the instrument handle to move in a retraction direction away from the first robotic arm that is coupled to the instrument feeder device. In some cases, the control circuitry can cause the second robotic arm to actuate by a particular amount. In examples, the second robotic arm can be moved without actuating the drive output of the first robotic arm that is configured to control axially motion of the elongate shaft (e.g., without actively actuating the drive output, since some actuation may naturally occur as the second robotic arm moves). As such, in some cases, the control circuitry can allow the drive output to actuate/rotate less than a threshold amount, while the second robotic arm is moved away from the first robotic arm.

At block 1810, the process 1800 can include determining a drive output force associated with the drive output and/or a robotic arm force associated with a robotic arm. For example, the control circuitry can determine a drive force (e.g., torque) applied by a drive output(s) that is coupled to the instrument feeder device to facilitate insertion/retraction of the shaft. Further, the control circuitry can determine a robotic arm force applied by a robotic arm that is coupled to the instrument base (e.g., the second robotic arm). In some instances, the robotic arm force can account for a current force applied/implemented to control a position of the robotic arm (also referred to as "the external force, net instrument force, or resultant force") and/or the initial/reference force applied by the robotic arm (determined at block 1806). For example, the robotic arm force can be calculated by subtracting the initial/reference force from the external force (i.e., robotic arm force=external force−reference force). However, the robotic arm force can be calculated in other manners.

At block 1812, the process 1800 can include determining whether the second robotic arm (that is coupled to the instrument handle) has actuated more than a threshold amount and/or has reached a workspace boundary. For example, the control circuitry can monitor/detect a distance that the second robotic arm (that is coupled to the instrument handle) has moved from the first robotic arm (that is coupled to the instrument feeder device) and/or detect the position of the second robotic arm, which can be used to determine whether the second robotic arm has reached a distance limit and/or reached a workspace boundary. The distance limit and/or the workspace boundary may be set/defined to avoid collisions with an object/patient in an environment. For example, the workspace boundary can be a virtual boundary.

If it is determined that the second robotic arm has actuated more than the threshold amount and/or has reached the workspace boundary, the process 1800 can proceed to block 1814 (i.e., the YES branch). Alternatively, if it is determined that the second robotic arm is not actuated more than the threshold and/or has not reached the workspace boundary, the process 1800 can proceed to block 1816 (i.e., the NO branch).

At block 1814, the process 1800 can include generating a signal indicating that the second robotic arm actuated more than a threshold amount and/or reached a workspace boundary. For example, the control circuitry can generate/send the signal based upon a determination at block 1812 that the second robotic arm actuated more than the threshold amount and/or reached the workspace boundary. The signal can cause a notification to be provided to instruct a user to reload the medical instrument and/or adjust the second robotic arm, such as by removing and reattaching the instrument handle to the second robotic arm, moving the second robotic arm to manually remove slack, etc. In some instances, the signal can be generated/sent in cases where there is too much slack in the elongate shaft, such as more than a threshold amount that could be removed by the system.

Although blocks 1812 and 1814 are illustrated in the example of FIG. 18-1, in some instances such blocks (and/or other blocks of the process 1800) may the eliminated.

At block 1816, the process 1800 can include determining whether the drive output force is greater than a first threshold and/or the robotic arm force is greater than a second threshold. The second threshold can be the same as or different than the first threshold. For example, the control circuitry can determine whether the drive output force determined at block 1810 and/or the robotic arm force determined at block 1810 are greater than their respective thresholds, which can indicate that there is tension on the elongate shaft between the first and second robotic arms. As such, at block 1816, the control circuitry can determine if there is less than a predetermined amount of slack in the elongate shaft (e.g., no/zero slack).

Although two thresholds are used in this example, the techniques can be implemented with a single threshold, wherein the drive output force and the robotic arm force can be combined and compared to the single threshold.

If is determined that the drive output force is greater than the first threshold and/or the robotic arm force is greater than the second threshold, the process 1800 can proceed to block 1818 in FIG. 18-2 (i.e., the YES branch). Alternatively, if it is determined that the drive output force is not greater than the first threshold and/or the robotic arm force is not greater than the second threshold, the process 1800 can return to block 1808 (e.g., the NO branch). The control circuitry can loop through blocks 1808, 1810, and 1812 any number of times to remove slack in the elongate shaft, if needed.

In FIG. 18-2, at block 1818, the process 1800 can include loosening the tension on the elongate shaft. For example, the control circuitry can cause the second robotic arm that is coupled to the instrument handle to move closer to the first robotic arm in an insertion direction and/or cause the instrument feeder device to move the elongate shaft in a retraction direction. In some instances, moving the second robotic arm in a direction away from the first robotic arm at block 1808 can cause the elongate shaft to be over tensioned. As such, the operation of block 1818 can be performed to loosen such tension (e.g., slightly).

At block 1820, the process 1800 can include determining whether the second robotic arm has moved a first predetermined distance and/or the elongate shaft has retracted a second predetermined distance. For example, the control circuitry can determine whether the second robotic arm moved (at block 1818) in an insertion direction by at least a first predetermined amount (e.g., moved closer to the first robotic arm by a particular amount) and/or whether the elongate shaft has been moved by the instrument feeder device (at block 1818) by at least a second predetermined distance. The second predetermined distance can be the same as or different than the first predetermined distance. Additionally, or alternatively, at block 1820, the control circuitry can determine if an amount of force applied by/to a drive out that is used to control the instrument feeder device/engagement assembly/rollers and/or an amount of force implemented/applied by the first/second robotic arm has changed by a threshold amount or is less than a threshold (e.g., indicating that the tension has loosened).

If it is determined that the second robotic arm has moved the first predetermined distance and/or the elongate shaft has retracted the second predetermined distance, the process 1800 can proceed to block 1822 (i.e., the YES branch). Alternatively, if it is determined that the second robotic arm has not moved the first predetermined distance and/or the elongate shaft has not retracted the second predetermined distance, the process 1800 can return to block 1818 (i.e., the NO branch). The operation at block 1818 can be performed any number of times to incrementally loosen the tension on the elongate shaft (e.g., actuate the second robotic arm and/or axially move the elongate shaft by a particular amount each time at block 1818) until one or more criteria are satisfied.

Although blocks 1818 and 1820 are illustrated in the example process 1800, in some instances such blocks can be eliminated. In one illustration, the block 1818 is performed a single instance (e.g., the block 1820 is eliminated).

At block 1822, the process 1800 can include controlling the instrument feeder device to disengage with the elongate shaft and/or enable the elongate shaft to roll. For example, the control circuitry can cause the instrument feeder device to transition to a disengaged state (e.g., an intermediate state in which the elongate shaft is retained, a fully open/disengaged state, or another disengaged state). In one illustration, the instrument feeder device can transition to an intermediate state where rollers/actuators are disengaged from the elongate shaft and a cover/retention feature is closed. This can allow an admittance control mode to be enabled (e.g., for manual adjustment of the first robotic arm that is coupled to the instrument feeder device) and/or the elongate shaft to be rolled (e.g., move freely within a channel while being retained in the instrument feeder device).

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure herein should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A system comprising:
an instrument feeder device configured to couple to a drive output and including an engagement assembly configured to engage with an elongate shaft of a medical instrument; and
control circuitry configured to:
cause the drive output to actuate the engagement assembly so that the engagement assembly moves from an engaged state to a disengaged state or from the disengaged state to the engaged state;
determine an amount of force applied by the drive output for actuating the engagement assembly;
determine a position of the drive output based on the amount of force applied by the drive output; and
determine a state of the engagement assembly based on the position of the drive output.

2. The system of claim 1, wherein the control circuitry is configured to determine the state of the engagement assembly based on at least one of a comparison of the amount of force applied by the drive output to one or more thresholds or a comparison of the position of the drive output to one or more reference positions.

3. The system of claim 1, wherein the engagement assembly includes an actuator configured to axially move the elongate shaft and a channel configured to receive the elongate shaft.

4. The system of claim 3, wherein the state of the engagement assembly indicates at least one of whether or not the actuator is engaged with the elongate shaft or whether or not the elongate shaft is properly positioned within the channel.

5. The system of claim 3, wherein the actuator is engaged in the engaged state, the actuator is disengaged in the disengaged state, and the position of the drive output is a first position associated with a first change in the amount of force applied by the drive output that occurred while moving the engagement assembly from the engaged state to the disengaged state, the first change in the amount of force being greater than a first threshold.

6. The system of claim 5, wherein the control circuitry is configured to:

cause the drive output to actuate the engagement assembly from the disengaged state to the engaged state; and determine a second position of the drive output that is associated with a second change in the amount of force applied by the drive output, the second change in the amount of force being greater than the first threshold or a second threshold.

7. The system of claim 6, wherein the control circuitry is configured to:

identify a third position of the drive output that is associated with an intermediate state in which the actuator is disengaged from the elongate shaft;

based at least in part on the second position relative to the first position and the third position, determine whether or not the elongate shaft is properly received in the channel; and based at least in part on the determination of whether or not the elongate shaft is properly received in the channel, control the instrument feeder device.

8. The system of claim 1, wherein the control circuitry is configured to:

detect that at least one of (i) the instrument feeder device was coupled to a robotic system associated with the drive output, (ii) the medical instrument was coupled to the robotic system, (iii) a roll of the elongate shaft is instructed, or (iv) manual movement of a robotic arm of the robotic system is enabled; and based at least in part on the detection, cause the drive output to actuate the engagement assembly.

9. The system of claim 3, wherein the instrument feeder device is configured to bias the actuator to the engaged state or the disengaged state.

10. The system of claim 3, wherein the position of the drive output is a first position associated with a first change in the amount of force applied by the drive output that occurred while moving the engagement assembly from the engaged state to the disengaged state, and wherein the control circuitry is configured to:

cause the drive output to actuate the engagement assembly from the disengaged state towards the engaged state;

determine a second position of the drive output that is associated with a second change in the amount of force;

based at least in part on the second position relative to the first position, determine that the elongate shaft is at least one of not received in the engagement assembly or not properly received in the engagement assembly; and based at least in part on the determination that the elongate shaft is at least one of not received in the engagement assembly or not properly received in the engagement assembly, cause the drive output to actuate the engagement assembly to the disengaged state.

11. The system of claim 3, wherein the engagement assembly further includes a retention feature configured to selectively open or close a channel, wherein the position of the drive output is a first position associated with a first change in the amount of force applied by the drive output that occurred while moving the engagement assembly from the engaged state to the disengaged state, and wherein the control circuitry is configured to:

cause the drive output to actuate the engagement assembly from the disengaged state towards the engaged state;

determine a second position of the drive output that is associated with a second change in the amount of force;

identify a third position of the drive output that is associated with an intermediate state in which the retention feature is closed and the actuator is disengaged from the elongate shaft;

based at least in part on the second position relative to the first position and the third position, determine that the elongate shaft is at least one of not received in the engagement assembly or not properly received in the engagement assembly; and based at least in part on the determination that the elongate shaft is at least one of not received in the engagement assembly or not properly received in the engagement assembly, cause the drive output to actuate the engagement assembly to the disengaged state.

12. A method comprising:

controlling a drive output to cause actuation of an engagement assembly of an instrument feeder device so that the engagement assembly moves from an engaged state to a disengaged state or from the disengaged state to the engaged state, the instrument feeder device configured to couple to a medical instrument;

determining an amount of force applied by the drive output for actuating the engagement assembly;

determining a position of the drive output based on the amount of force applied by the drive output; and determining an engagement state of the engagement assembly based on the position of the drive output.

13. The method of claim 12, wherein the engagement state of the engagement assembly is determined based on at least one of a comparison of the amount of force applied by the drive output to one or more thresholds or a comparison of the position of the drive output to one or more reference positions.

14. The method of claim 12, wherein the instrument feeder device includes an actuator configured to axially move an elongate shaft of the medical instrument and a channel configured to receive the elongate shaft.

15. The method of claim 14, wherein the engagement state of the engagement assembly indicates at least one of whether or not the actuator is engaged with the elongate shaft or whether or not the elongate shaft is properly positioned within the channel.

16. The method of claim 14, wherein the position of the drive output is a first position associated with a first change in the amount of force applied by the drive output that occurred while moving the engagement assembly from the engaged state to the disengaged state in which the actuator is disengaged, the method further comprising:

controlling the drive output to actuate the engagement assembly from the disengaged state towards the engaged state in which the actuator is engaged;

determining a second position of the drive output that is associated with a second change in the amount of force; and based at least in part on the second position relative to the first position, determining whether or not the elongate shaft is properly received in the channel.

17. A robotic system comprising:
a robotic arm;
an end effector associated with a distal end of the robotic arm, the end effector including a first drive output configured to actuate a first drive input of an instrument feeder to control an engagement state of an engagement assembly of the instrument feeder with an elongate shaft of an instrument, the actuation of the first drive input moving the engagement assembly from an engaged state to a disengaged state or from the disengaged state to the engaged state; and
control circuitry communicatively coupled to the robotic arm and configured to;
determine an amount of force applied by the first drive output for actuating the first drive input;
determine a position of the first drive output based on the amount of force applied by the first drive output; and
determine the engagement state of the engagement assembly based on the position of the first drive output.

18. The robotic system of claim 17, wherein the end effector further includes a second drive output configured to actuate a second drive input of the instrument feeder to cause axial motion of the elongate shaft.

19. The robotic system of claim 17, wherein:
the instrument feeder includes an actuator configured to axially move the elongate shaft, a channel configured to receive the elongate shaft, and a retention feature configured to selectively open or close the channel; and
the engagement state of the engagement assembly indicates at least one of whether or not the actuator is engaged with the elongate shaft, whether or not the retention feature is closed, or whether or not the elongate shaft is properly positioned within the channel.

20. The robotic system of claim 19, wherein the control circuitry is configured to:
cause the engagement assembly to transition to the disengaged state in which the actuator is disengaged;
cause the instrument feeder to move towards the engaged state;
determine a first position of the first drive output that is associated with a first change in the amount of force applied by the first drive output that occurred while moving the instrument feeder towards the engaged state;
identify a second position of the first drive output that is associated with at least one of (i) a second change in the amount of force applied by the first drive output, or (ii) a state in which the actuator is disengaged from the elongate shaft and the retention feature is closed; and
based at least in part on the first position relative to the second position, determine whether or not the elongate shaft is properly received in the channel.

* * * * *